(12) United States Patent
Barrow et al.

(10) Patent No.: US 6,610,701 B2
(45) Date of Patent: Aug. 26, 2003

(54) THROMBIN INHIBITORS

(75) Inventors: James C. Barrow, Harleysville, PA (US); Craig Coburn, Royersford, PA (US); Harold G. Selnick, Ambler, PA (US); Phung L. Ngo, Upper Darby, PA (US)

(73) Assignee: Merck & Co., Inc., Rahway, NJ (US)

( * ) Notice: Subject to any disclaimer, the term of this patent is extended or adjusted under 35 U.S.C. 154(b) by 12 days.

(21) Appl. No.: 10/071,422

(22) Filed: Feb. 8, 2002

(65) Prior Publication Data

US 2002/0193398 A1 Dec. 19, 2002

Related U.S. Application Data

(60) Provisional application No. 60/267,960, filed on Feb. 9, 2001.

(51) Int. Cl.[7] ............... A61K 31/4375; A61K 31/444; A61K 31/4725; C07D 401/12; C07D 401/14; A61P 7/02

(52) U.S. Cl. .............. 514/300; 514/307; 514/314; 514/332; 514/333; 514/352; 514/334; 514/621; 514/357; 514/337; 514/618; 514/619; 546/113; 546/122; 546/146; 546/172; 546/175; 546/256; 546/265; 546/309; 546/312; 546/334; 564/162; 564/168

(58) Field of Search ................ 546/113, 122, 546/146, 172, 256, 265, 309; 514/300, 307, 314, 332, 333, 352, 337

(56) References Cited

U.S. PATENT DOCUMENTS

| | | | |
|---|---|---|---|
| 5,084,466 A | 1/1992 | Alig et al. | |
| 5,518,735 A | 5/1996 | Sturzebecher et al. | |
| 5,872,138 A | 2/1999 | Naylor-Olsen et al. | |
| 6,387,911 B1 * | 5/2002 | Burgey .................. | 514/255.05 |
| 2002/0025947 A1 * | 2/2002 | South et al. ................ | 514/179 |
| 2002/0061872 A1 * | 5/2002 | Pan et al. .............. | 514/211.01 |

FOREIGN PATENT DOCUMENTS

| EP | 0 195 212 | 11/1993 |
|---|---|---|
| EP | 0 363 284 | 5/1997 |

OTHER PUBLICATIONS

Mack, et al., "Design, Synthesis and Biological Activity of Novel Rigid Aminido–Phenylalanine Derivatives as Inhibitors of Thrombin", *J. Enzyme Inhibition*, vol. 9, pp. 73–86 (1995).

Brown, et al., "Design of Orally Active, Non–Peptidic Inhibitors of Human Leukocyte Elastase", *J. Med. Chem.*, vol. 37, pp. 1259–1261 (1994).

Edwards, et al., "Design, Synthesis, and Kinetic Evaluation of a Unique Class of Elastase Inhibitors, the Peptidyl a–Ketobenzoxazoles, and the X–ray Crystal Structure of the Covalent Complex between Porcine Pancreatic Elastase and Ac–Ala–Pro–Val–2–Benzoxazole", *J. Am. Chem. Soc.*, vol. 114, pp. 1854–1863 (1992).

Rewinkel, et al., "Strategies and Progress Towards the Ideal Orally Active Thrombin Inhibitor", *Current Pharmaceutical Design*, vol. 5, pp. 1043–1075 (1999).

Tucker, et al., "The Development of Novel Noncovalent Thrombin Inhibitors", *Advances in Amino Acid Mimetics and Peptidomimetics*, vol. 2, pp. 53–87 (1999).

Hauptmann, et al., "Synthetic Inhibitors of Thrombin and Factor Xa: From Bench to Bedside", *Thrombosis Research*, vol. 93, pp. 203–241 (1999).

Sanderson, et al., "Thrombin Inhibitor Design", *Current Medicinal Chemistry*, vol. 5, pp. 289–304 (1998).

Fevig et al., "Anticoagulants: Thrombin and Factor Xa Inhibitors", *Annual Reports in Medicinal Chemistry–34*, Chapter 9, pp. 81–100 (1999).

* cited by examiner

*Primary Examiner*—Evelyn Mei Huang
(74) *Attorney, Agent, or Firm*—Richard S. Parr; Valerie J. Camara

(57) ABSTRACT

Compounds of the invention are useful in inhibiting thrombin and treating blood coagulation and cardiovascular disorders and have the following structure:

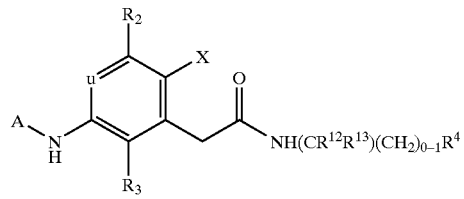

wherein
$R^3$ is hydrogen or halogen, and u is N or CH.

19 Claims, No Drawings

THROMBIN INHIBITORS

This application claims benefit of 60/267,960, filed Feb. 9, 2001.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.,* (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., *J. Med. Chem.,* Vol. 37, pages 1259–1261 (1994) describes orally active, non-peptidic inhibitors of human leukocyte elastase which contain trifluoromethylketone and pyridinone moieties.

H. Mack et al., *J. Enzyme Inhibition,* Vol. 9, pages 73–86 (1995) describes rigid amidino-phenylalanine thrombin inhibitors which contain a pyridinone moiety as a central core structure.

The present invention includes benzyl or pyridyl based compounds which are useful as thrombin inhibitors.

SUMMARY OF THE INVENTION

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention are useful for inhibiting thrombin and treating blood coagulation and cardiovascular disorders. The invention includes compounds having the structure

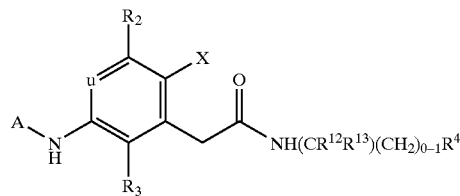

wherein
u is N or CH;
A is —$CH_2C(Y)_2R^1$ or —$S(O)_2CH_2R^1$;
$R^1$ is
1) a 6-membered non-heterocyclic unsaturated ring system, unsubstituted, monosubstituted or disubstituted, same or different, with $R^8$,
2) a 6-membered heterocyclic saturated ring system wherein 1 or 2 ring atoms are independently selected from the group of heteroatoms consisting of N, O and S, wherein the ring is unsubstituted, monosubstituted or disubstituted, same or different, with $R^8$, or
3)

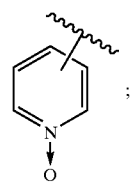

;

$R^2$ is hydrogen or F;
$R^3$ is hydrogen or halogen;
X is hydrogen, halogen, $C_{1-4}$ alkyl, CN or $CF_3$;
Y is hydrogen, $C_{1-4}$ alkyl, or F;
$R^4$ is
1) a 6-membered non-heterocyclic unsaturated ring system, unsubstituted, monosubstituted, or disubstituted, same or different, with $R^9$,
2) a 5- or 6-membered monocyclic heteroatom-containing unsaturated ring system wherein 1 or 2 ring atoms is selected from N, wherein the ring is unsubstituted or monosubstituted with $R^9$,
3) a 9- or 10-membered bicyclic heteroatom-containing unsaturated ring system wherein 1 or 2 ring atoms is selected from N, wherein the ring is unsubstituted or monosubstituted with $R^9$,
4) —$CH_2C(O)NHC(NH)NH_2$;
$R^8$ and $R^9$ are independently
1) halogen,
2) $C_{1-8}$ alkyl,
3) $C_{1-4}$ alkylene $C_{3-7}$ cycloalkyl
4) $(CH_2)_{1-2}NH_2$,
5) a 5-membered heterocylcic unsaturated ring having 3 or 4 N atoms, wherein the ring is unsubstituted, monosubstituted, or disubstituted, same or different, with $C_{1-8}$ alkyl, $C_{3-7}$ cycloalkyl, $C_{1-4}$ alkylene $C_{3-7}$ cycloalkyl, $NH_2$, or $(CH_2)_{0-4}X^2(CH_2)_{0-3}CH_3$, wherein $X^2$ is a bond, S, S(O), $S(O)_2$, O, or NH,
6) —$OCH_2C(O)NHR^{10}$, or
7) —$(CH_2)_{1-2}NHC(O)OR^{11}$;
$R^{10}$ is $C_{1-4}$ alkyl or $C_{3-7}$ cycloalkyl;

$R^{11}$ is $C_{1-4}$ alkyl; and $R^{12}$ and $R^{13}$, same or different, are selected from the group consisting of hydrogen and $C_{1-4}$ alkyl, or a pharmaceutically acceptable salt thereof.

In a class of compounds of the invention, Y is hydrogen, $CH_3$, or F, and $R^3$ is hydrogen, Cl, or F.

In a subclass of this class of compounds, X is hydrogen, F, Cl, Br, $C_{1-4}$ alkyl, CN or $CF_3$.

In a group of this subclass of compounds, $R^1$ is

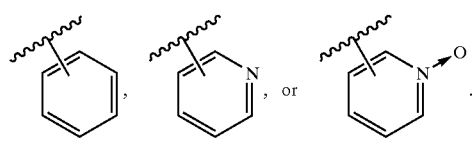

In a subgroup of this group, $R^4$ is $C_2C(O)NHC(NH)NH_2$,

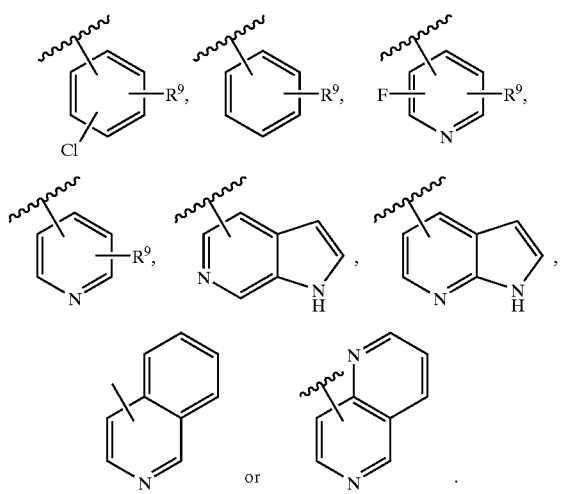

In a family of this subgroup, $R^9$ is selected from the group consisting of Cl, F, —$CH_3$, —$OCH_2C(O)NHCH_2CH_3$, —$(CH_2)_{1-2}NHC(O)OC(CH_3)_3$, —$(CH_2)_{1-2}NH_2$,

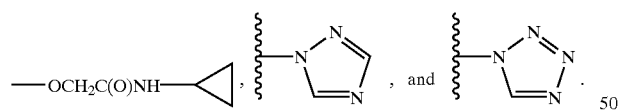

In a subfamily of this family,

A is

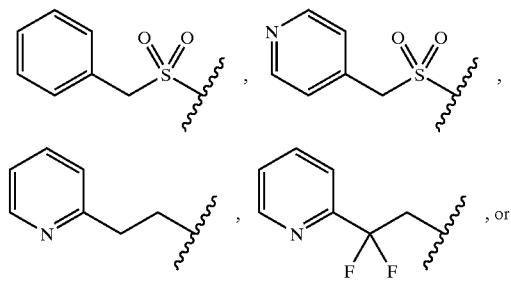

-continued

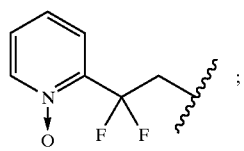

u is N or CH;

$R^2$ is hydrogen or F;

$R^3$ is Cl or F;

X is hydrogen, Cl or F;

$R^{12}$ is hydrogen;

$R^{13}$ is hydrogen or $CH_3$;

$R^4$ is

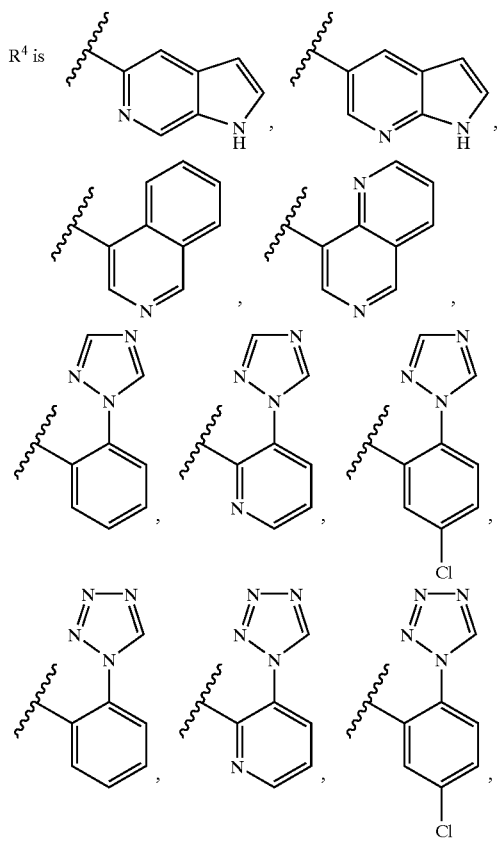

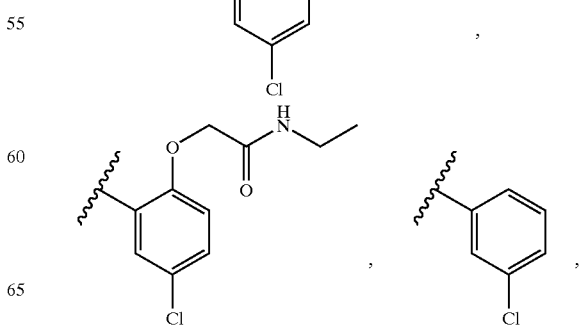

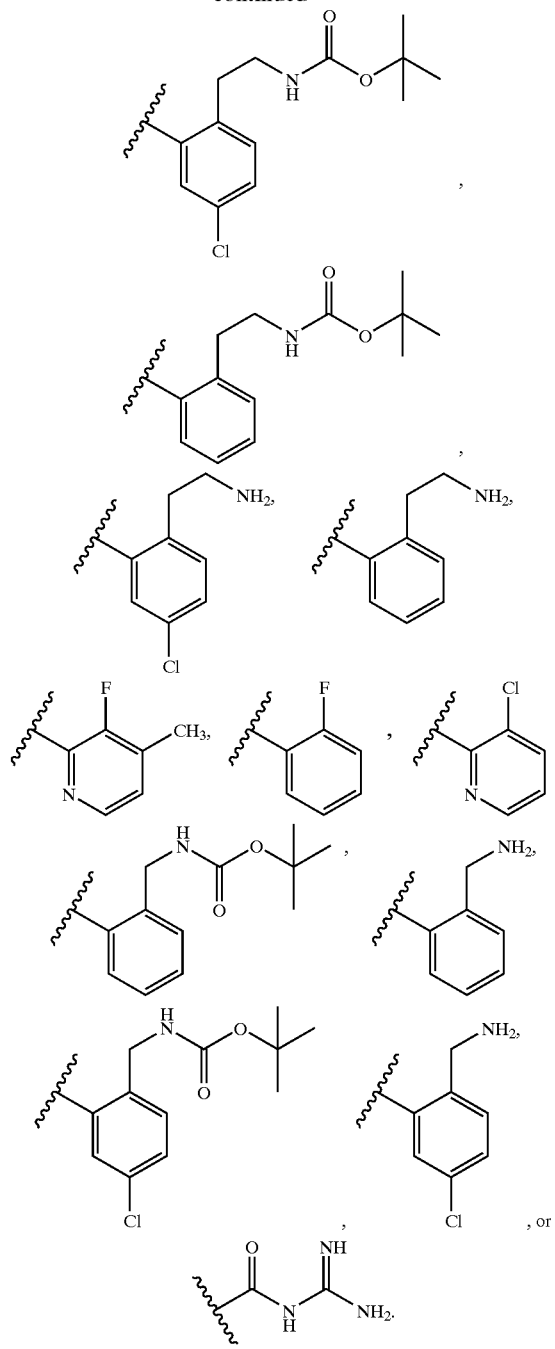
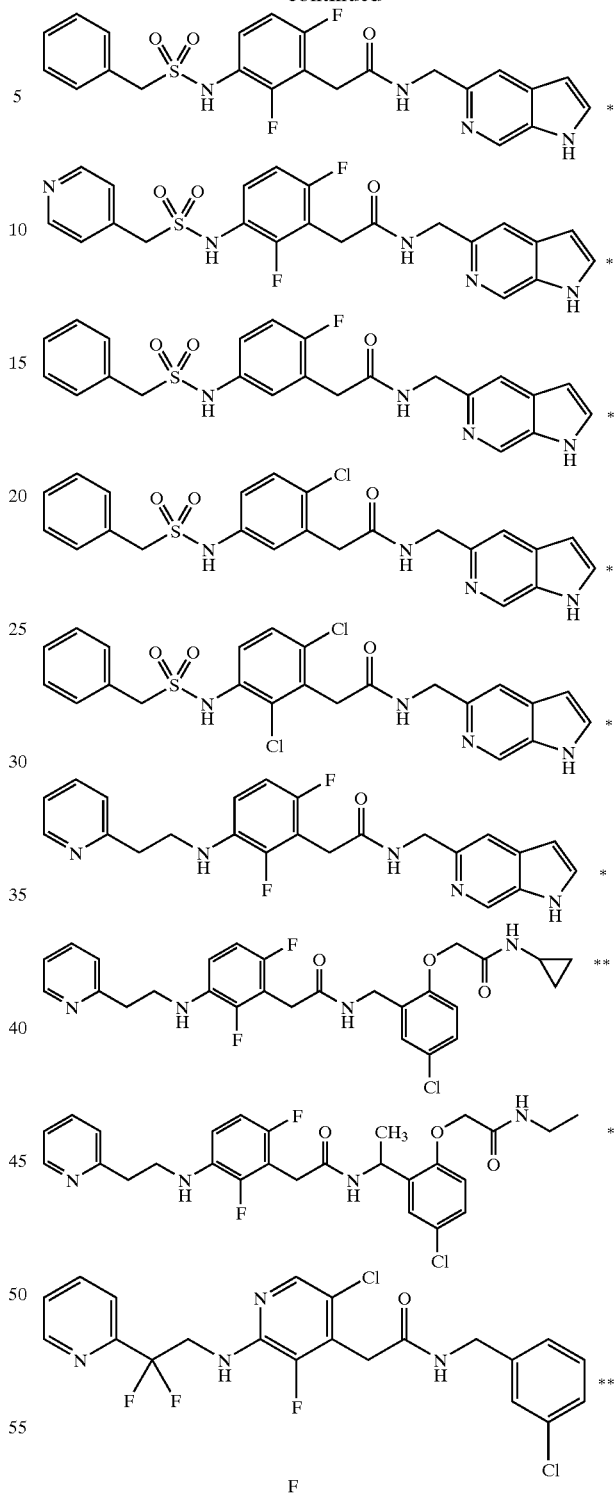
Examples of this family are listed below. Inhibitory activity, as measured by the in vitro assay described in the specification, where indicated, is represented by "*", indicating Ki greater than or equal to 20 nM, or "**", indicating Ki less than 20 nM.
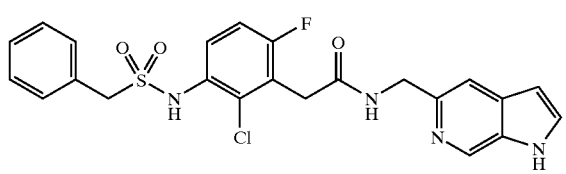

-continued

-continued
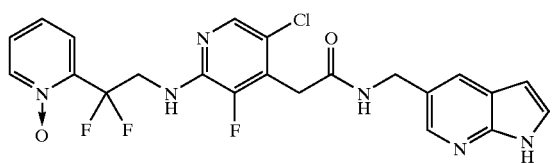**
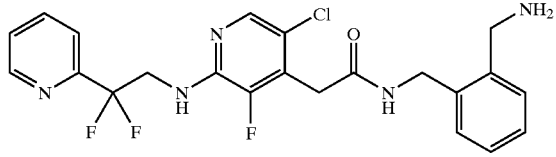*
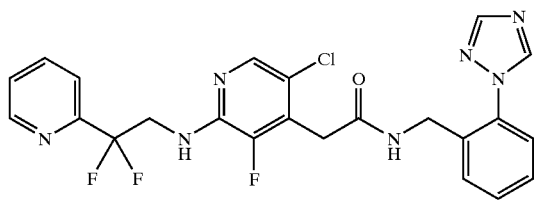**
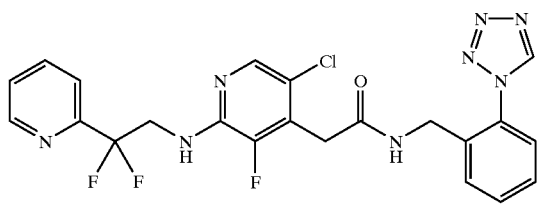**
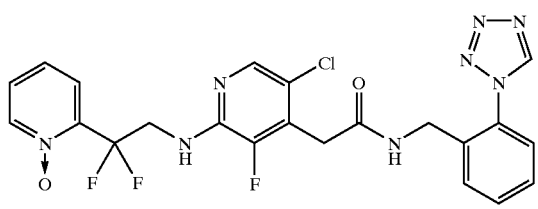**
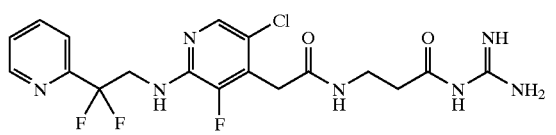**
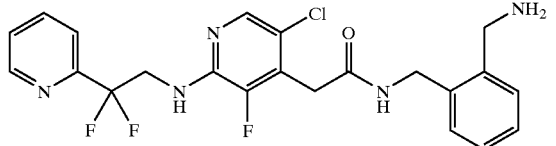**
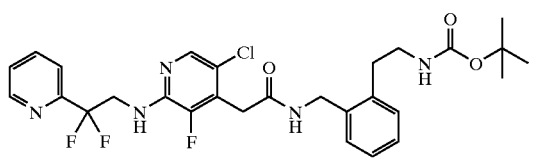**
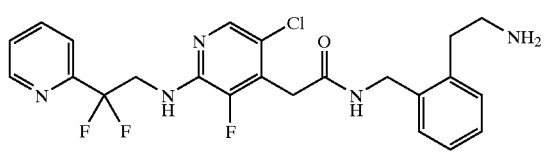**
-continued
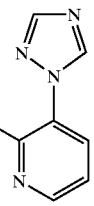**
Additional examples include
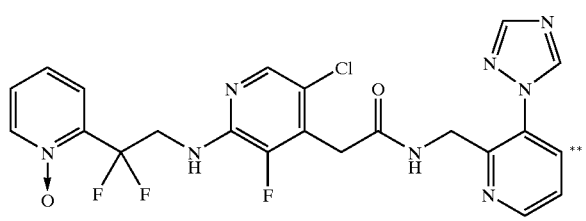**
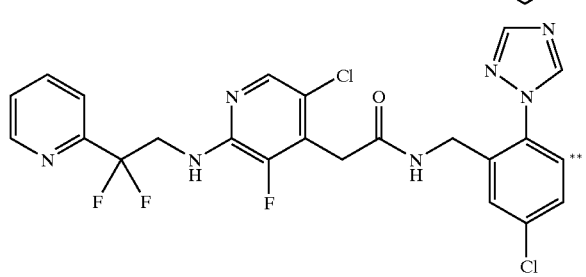**
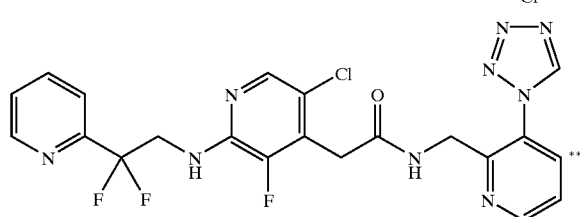**
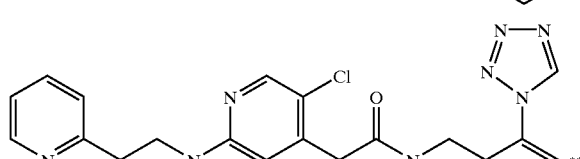**
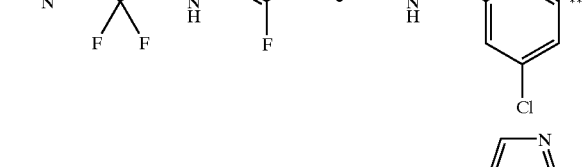**
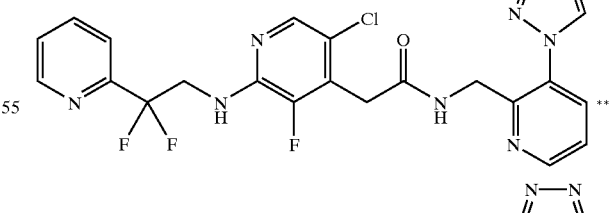**
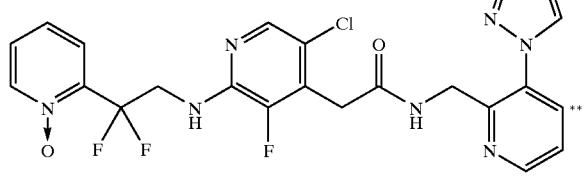**

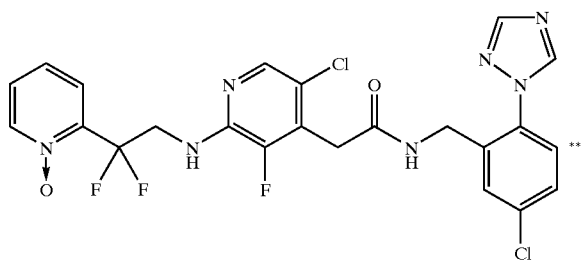
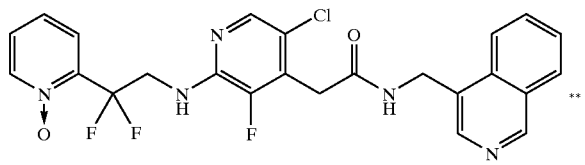
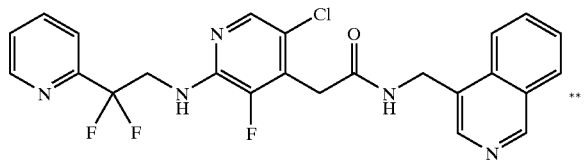
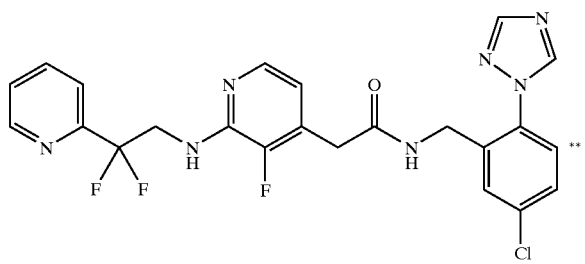
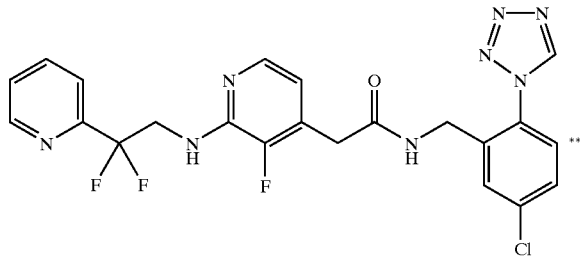
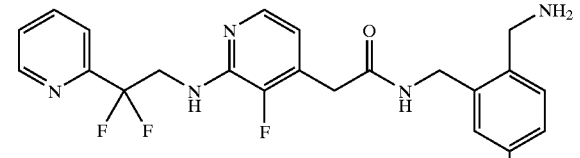
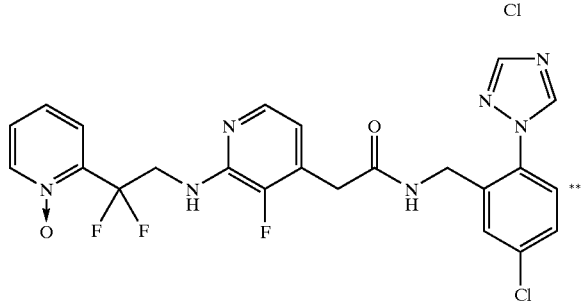

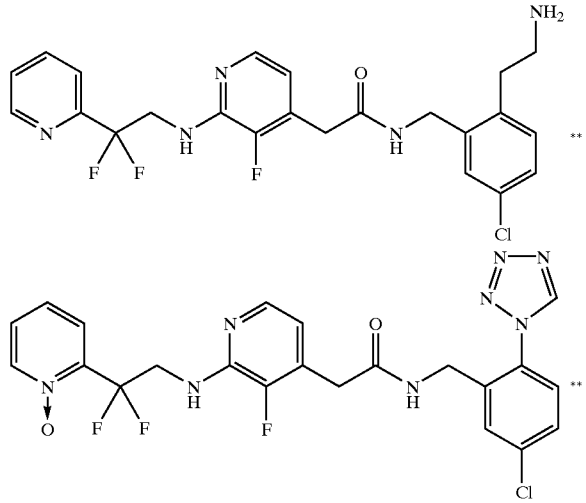
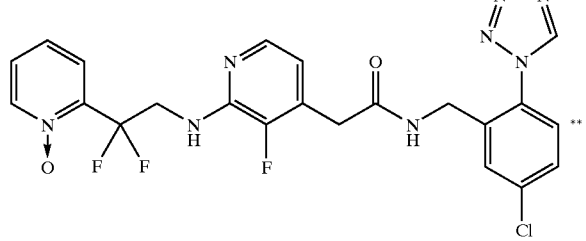

The compounds of the present invention may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

Some abbreviations that may appear in this application are as follows.

| ABBREVIATIONS | |
|---|---|
| Boc₂O | di-t-butyl dicarbonate |
| BuLi | butyl lithium |
| CaCO₃ | calcium carbonate |
| CH₂Cl₂ | dichloromethane |
| DAST | diethylaminosulfurtrifluoride |
| DBU | 1,8-diazobicyclo[5.4.0]undec-7-ene |
| DCM | dichloromethane |
| DMAP | dimethylaminopyridine |
| DMF | dimethylformamide |
| DPPA | diphenylphosphoryl azide |
| EDC | 1-ethyl-3-(3-dimethylaminopropyl) carbodiimide hydrochloride |
| EtOAc | ethyl acetate |
| EtOH | ethanol |
| Et₃N | triethylamine |
| HCl | hydrochloric acid |
| H₂SO₄ | sulfuric acid |
| HOAc | acetic acid |
| HOAt | 1-hydroxy-7-aza-benzotriazole hydrate |
| HOBT | 1-hydroxybenzotriazole hydrate |
| H₂SO₄ | sulfuric acid |
| LAH | lithium aluminum hydride |
| LDA | lithium diisopropylamide |
| LiCl | lithium chloride |
| LiOH | lithium hydroxide |
| MCPBA | m-chloroperoxybenzoic acid |
| MeI | iodomethane |
| MeOH | methanol |
| MgSO₄ | magnesium sulfate |
| N₃PO(Ph)₂ | diphenylphosphoryl azide |
| NaBH₄ | sodium borohydride |

| ABBREVIATIONS | |
|---|---|
| NaHCO$_3$ | sodium hydrogen carbonate |
| NaN$_3$ | sodium azide |
| NaOH | sodiumhydroxide |
| NaSMe | sodium thiomethoxide |
| Na$_2$SO$_4$ | sodium sulfate |
| nBuLi | n-butyllithium |
| NH$_4$OH | ammonium hydroxide |
| NMM | N-methylmorpholine |
| PPh$_3$ | triphenylphosphine |
| Pd-C | palladium on activated carbon catalyst |
| Pd(PPh$_3$)$_4$ | tetrakis triphenylphosphine palladium |
| (Ph$_3$P)$_2$PdCl$_2$ | bis(triphenylphosphine)palladium dichloride |
| SeO$_2$ | selenium oxide |
| THF | tetrahydrofuran |
| TMSCN | trimethylsilyl cyanide |
| Zn(CN)$_2$ | zinc cyanide |

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "C$_{3-7}$cycloalkyl" is intended to include cyclopropyl, cyclobutyl, cyclopentyl, cyclohexyl and cycloheptyl, and the like.

The term "C$_{7-12}$ bicyclic alkyl" is intended to include bicyclo[2.2.1]heptyl (norbornyl), bicyclo[2.2.2]octyl, 1,1,3-trimethyl-bicyclo[2.2.1]heptyl (bornyl), and the like.

The term "aryl" as used herein except where noted, represents a stable 6- to 10-membered mono- or bicyclic ring system such as phenyl, or naphthyl. The aryl ring can be unsubstituted or substituted with one or more of C$_{1-4}$ lower alkyl; hydroxy; alkoxy; halogen; amino. The term "heteroaryl" refers to a 5- to 7-membered unsaturated ring containing 1 or 2 heteroatoms selected from O, N, or S.

The term "heterocycle" or "heterocyclic ring", as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

The term "pyridyl-N-oxide" refers to a moiety having the structure

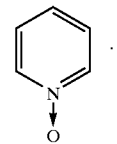

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems.

The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinylpyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The invention also includes a method for treating an inflammatory disease in a patient which comprises treating the patient with a composition comprising a compound of the present invention. Such diseases include but are not limited to nephritis, systemic lupus erythematosus, rheumatoid arthritis, glomerulonephritis, and sacoidosis.

The invention is also a method for treating an inflammatory disease in a patient that comprises treating the patient with a combination comprising a compound of the invention and an NSAID, e.g., a COX-2 inhibitor. Such diseases include but are not limited to nephritis, systemic lupus, erythematosus, rheumatoid arthritis, glomerulonephritis, vasculitis and sacoidosis.

The present invention is a method for relieving pain, fever and inflammation of a variety of conditions including nephritis, systemic lupus erythematosus, rheumatoid arthritis, glomerulonephritis, sacoidosis, rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures in a patient by administering to the patient a therapeutically effective amount of a compound of the invention. Thrombin inhibitors may also be useful for the treatment of dementia including pre-senile and senile dementia, and in particular, dementia associated with Alzheimer Disease.

In inflammatory diseases wherein fibrin formation is prominent, the fibrin may be a determinant of the pathology. Fibrin serves as a matrix onto which inflammatory cells can migrate and adhere. (see Sherman et al., 1977 *J. Exp. Med.* 145:76–85; Altieri et al., 1986 *J. Clin. Invest.* 78:968–976; Wright et al., 1983 *Proc. Natl. Acad. Sci.* 85:7734–7738; Altieri et al., 1993 *J. Biol. Chem.* 268;1847–1853). Fibrin also enhances expression of the inflammatory cytokine IL-1beta and decreases expression of IL-1 receptor antagonist by human peripheral blood mononuclear cells (see Perez 1995 *J. Immunol.* 154:1879–1887). The anticoagulants warfarin and heparin attenuate delayed-type hypersensitivity reactions and experimental nephritis in animals. (see Jasain et al., Immunopathogenesis of Rheumatoid Arthritis Eds. G. S. Panayi et al., Surrey, UK, Reedbooks, Ltd. and Halpern et al., 1965 *Nature* 205:257–259). Enzymatic defibrination with ancrod diminishes the degree of experimental nephritis (Naish et al., 1972 *Clin. Sci.* 42:643–646), systemic lupus erythematosus (Cole et al., 1990 *Kidney Int.* 37:29–35, and rheumatoid arthritis (see Busso et al., 1998 *J. Clin. Invest.* 102:41–50) in animals, and glomerulonephritis in man (see Kim et al., 1988 *Q. J. Med.* 69:879–905). Additionally, intra articular injection of fibrin induces arthritis in rabbits immunized with fibrin Dumonde et al., 1961 *British Journal of Experimental Pathology* XLIII:373–383), and antigen-induced arthritis in mice is exacerbated in urokinase-deficient mice wherein fibrinolysis synovial fibrin is compromised (see Busso et al., 1998 *J. Clin. Invest.* 102:41–50).

In diseases where fibrin deposition is prominent such as, but not limited to, rheumatoid arthritis, systemic lupus erythematosus, glomerulonephritis, vasculitis and sacoidosis, lowering the steady state concentration of fibrin by administration of a compound of the invention will, according to the instant invention, diminish the pathological inflammatory responses associated with these diseases.

Similarly, compounds of the invention will be useful as a partial or complete substitute for conventional NSAIDs in preparations wherein they are presently co-administered with other agents or ingredients. Thus in further aspects, the invention encompasses pharmaceutical compositions for treating inflammatory diseases as defined above comprising a non-toxic therapeutically effective amount of a compound of the invention as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating inflammatory diseases comprising administration to a patient in need of such treatment a non-toxic therapeutically effect amount of a compound of the invention, optionally co-administered with one or more of such ingredients as listed immediately above.

The instant invention also involves a novel combination therapy comprising the administration of a therapeutically effective amount of an NSAID such as a COX-2 inhibitor in combination with a therapeutically effective amount, as described above, of a compound of the invention to a mammal, and more particularly, to a human. The combination therapy is used to treat inflammatory diseases.

The instant pharmaceutical combinations comprising a compound of the invention in combination with an NSAID such as a COX-2 inhibitor include administration of a single pharmaceutical dosage formulation which contains both a compound of the invention and the NSAID, as well as administration of each active agent in its own separate pharmaceutical dosage formulation. Where separate dosage formulations are used, the compound of the invention and the NSAID can be administered at essentially the same time, i.e., concurrently, or at separately staggered times, i.e, sequentially. The "instant pharmaceutical combination" is understood to include all these regimens. Administration in these various ways are suitable for the present invention as long as the beneficial pharmaceutical effect of the compound of the invention and the NSAID are realized by the patient at substantially the same time. Such beneficial effect is preferably achieved when the target blood level concentrations of each active drug are maintained at substantially the same time. It is preferred that the compound of the invention and the NSAID be co-administered concurrently on a once-a-day dosing schedule; however, varying dosing schedules, such as the compound of the invention once per day and the NSAID once, twice or more times per day, or the NSAID once per day and the compound of the invention once, twice or more times per day, is also encompassed herein. A single oral dosage formulation comprised of both the compound of the invention and the NSAID is preferred. A single dosage formulation will provide convenience for the patient.

The instant invention also provides pharmaceutical compositions comprised of a therapeutically effective amount of an NSAID, or a pharmaceutically acceptable salt thereof, in combination with a therapeutically effective amount of a compound of the invention, or a pharmaceutically acceptable salt thereof, and a pharmaceutically acceptable carrier. One embodiment of the instant compositions is a single composition adapted for oral administration comprised of a therapeutically effective amount of a COX-2 inhibitor in combination with a therapeutically effective amount of a compound of the invention and a pharmaceutically acceptable carrier. The combination can also be administered in separate dosage forms, each having one of the active agents. If administered in separate dosage forms, the separate dosage forms are administered such that the beneficial effect of each active agent is realized by the patient at substantially the same time.

Common NSAIDs include salicylates such as aspirin, sodium salicylate, choline salicylate, salicylsalicylic acid, diflunisal, and salsalate; indoleacetic acids such as indomethacin and sulindac; pyrazoles such as phenylbutazone, oxyphenbutazone; pyrrolealkanoic acids such as tolmetin; phenylacetic acids such as ibuprofen, feroprofen, flurbiprofen, and ketoprofen; fenamates such as mefanamic acid, and meclofenamate; oxicams such as piroxicam; and naphthaleneacetic acids such as naproxen. Cyclo-oxygenase inhibitors such as COX-1 and COX-2 inhibitors are also NSAIDs.

Employing the human whole blood COX-1 assay and the human whole blood COX-2 assay described in C. Brideau et al, *Inflamm. Res.* 45: 68–74 (1996), herein incorporated by reference, preferably, the compounds have a cyclooxygenase-2 $IC_{50}$ of less than about 2 $\mu$M in the human whole blood COX-2 assay, yet have a cyclooxygenase-1 $IC_{50}$ of greater than about 5 $\mu$M in the human whole blood COX-1 assay. Also preferably, the compounds have a selectivity ratio of cyclooxygenase-2 inhibition over cyclooxygenase-1 inhibition of at least 10, and more preferably of at least 40. The resulting selectivity may indicate an ability to reduce the incidence of common NSAID-induced side effects.

The inhibitor of cyclooxygenase-2 may be administered at a dosage level up to conventional dosage levels for NSAIDs. Suitable dosage levels will depend upon the antiinflammatory effect of the chosen inhibitor of cyclooxygenase-2, but typically suitable levels will be about 0.001 to 50 mg/kg per day, preferably 0.005 to 30mg/kg per day, and especially 0.05 to 10mg/kg per day. The compound may be administered on a regimen of up to 6 times per day, preferably 1 to 4 times per day, and especially once per day, e.g. 12.5 mg per day or 25 mg per day.

The dosage regimen utilizing a compound of the invention in combination with the NSAID is selected in accordance with a variety of factors including type, species, age, weight, sex and medical condition of the patient; the severity of the condition to be treated; the route of administration; the renal and hepatic function of the patient; and the particular compound or salt or ester thereof employed. Since two different active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective dosage amounts needed to prevent, counter, or arrest the progress of the condition.

Administration of the drug combination to the patient includes both self-administration and administration to the patient by another person.

Additional active agents may be used in combination with the compound of the invention in a single dosage formulation, or may be administered to the patient in a separate dosage formulation, which allows for concurrent or sequential administration. Examples of additional active agents which may be employed include HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; LDL (low density lipoprotein) receptor inducers; vitamin $B_6$ (also known as pyridoxine) and the pharmaceutically acceptable salts thereof such as the HCl salt; vitamin $B_{12}$ (also known as cyanocobalamin); β-adrenergic receptor blockers; folic acid or a pharmaceutically acceptable salt or ester thereof such as the sodium salt and the methylglucamine salt; and antioxidant vitamins such as vitamin C and E and beta carotene.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin and simvastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The following examples and methods are illustrative of the invention as contemplated by the inventors and should not be construed as being limits on the scope or spirit of the instant invention. Unless otherwise stated, all NMR determinations were made using 400 MHz field strength.

General Scheme 1a

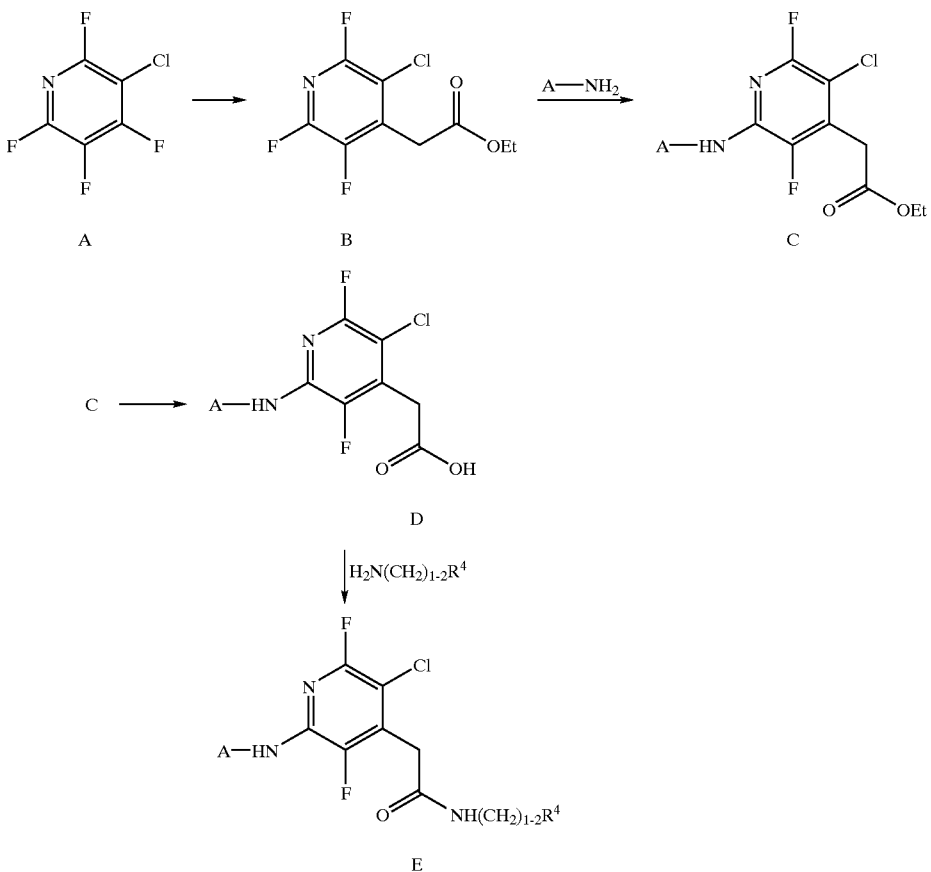

The compounds of the present invention can be prepared from 2,4,5,6,tetrafluoro-3-chloropyridine A according to Scheme 1a by displacement of the 4-fluoro with a malonate anion followed by displacement of the 6-fluoro with an amine to give intermediates with general structure C. This can be hydrolyzed and amide bond formation under standard carbodiimide conditions with a variety of amines ($H_2N(CH_2)_{1-2}R^4$) to obtain 2,5 difluoropyridine derivatives E.

General Scheme 1b

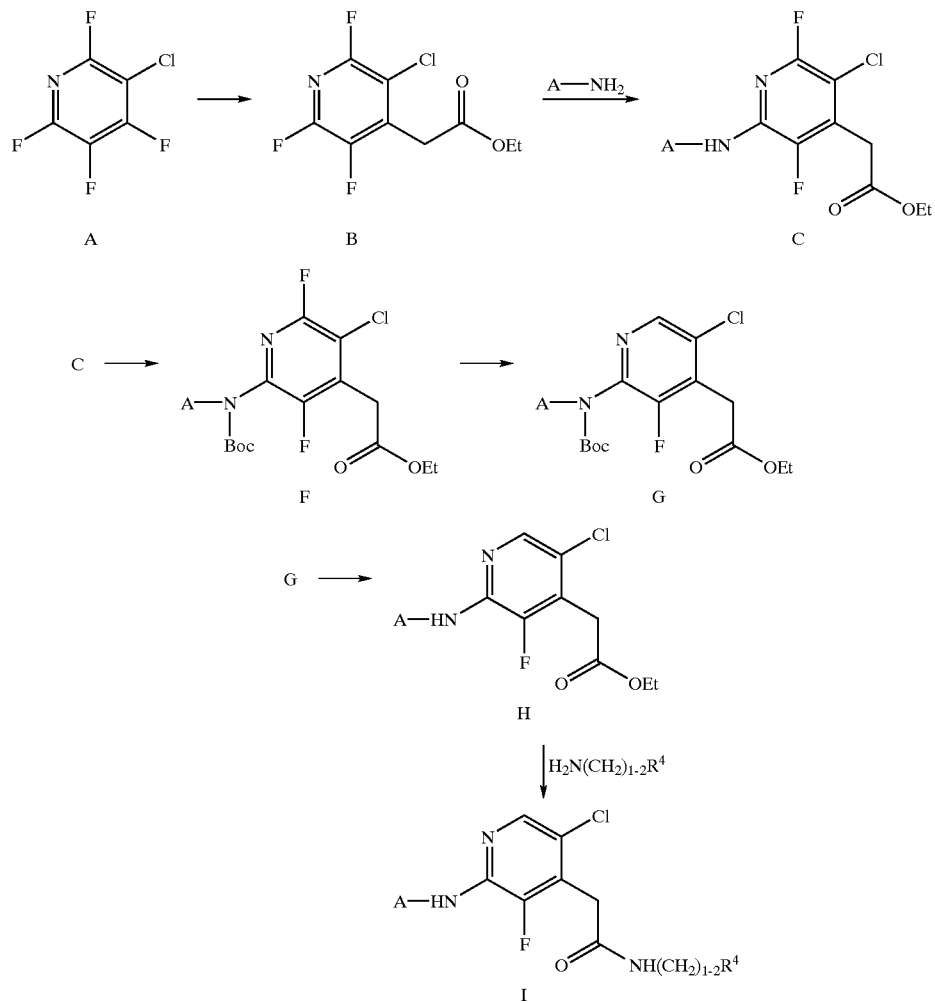

Alternatively, according to Scheme 1b, the 2-fluoro can be removed by Boc-protecting C to give F, then treatment with NaSMe followed by Raney Ni reduction to provide intermediate G. If desired, further manipulations to the sidechain A can be done at this stage (e.g. N-oxidation of pendant pyridyl), then the Boc group is removed to give H. Hydrolysis of the ester and amide bond formation under standard carbodiimide conditions with a variety of amines ($H_2N(CH_2)_{1-2}R^4$) affords the desired derivatives I.

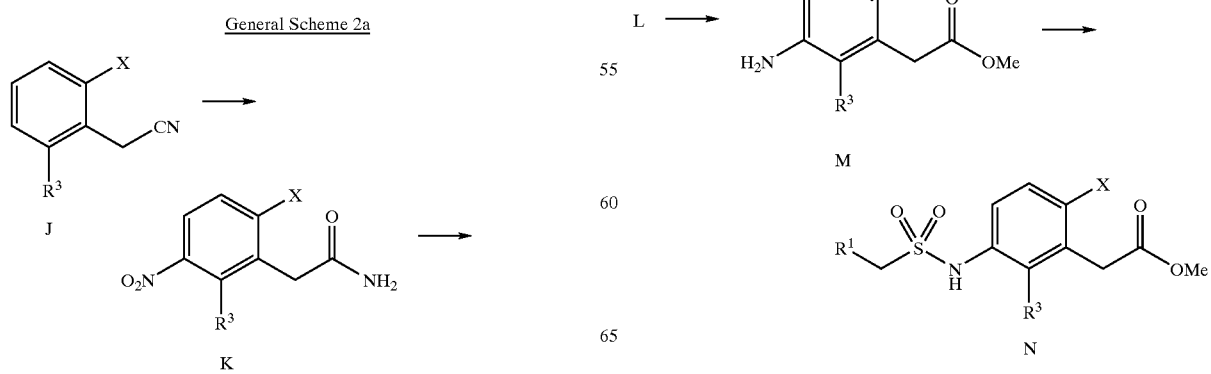

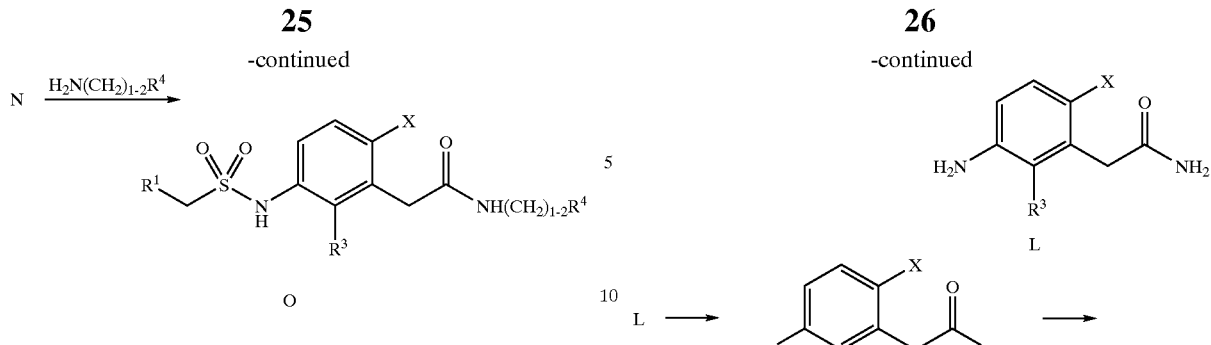

For phenyl-containing central ring compounds, an appropriately halogenated phenylacetonitrile derivative J can be nitrated (with concomitant hydrolysis of the nitrile) to give K followed by reduction of the nitro group to the amine L. Sulfonylation with an appropriately substituted sulfonyl chloride, hydrolysis of the primary amide to the corresponding carboxylic acid, and amide bond formation under standard carbodimide conditions with a variety of amines $(H_2N(CH_2)_{1-2}R^4)$ provides derivatives with the structure O.

General Scheme 2b

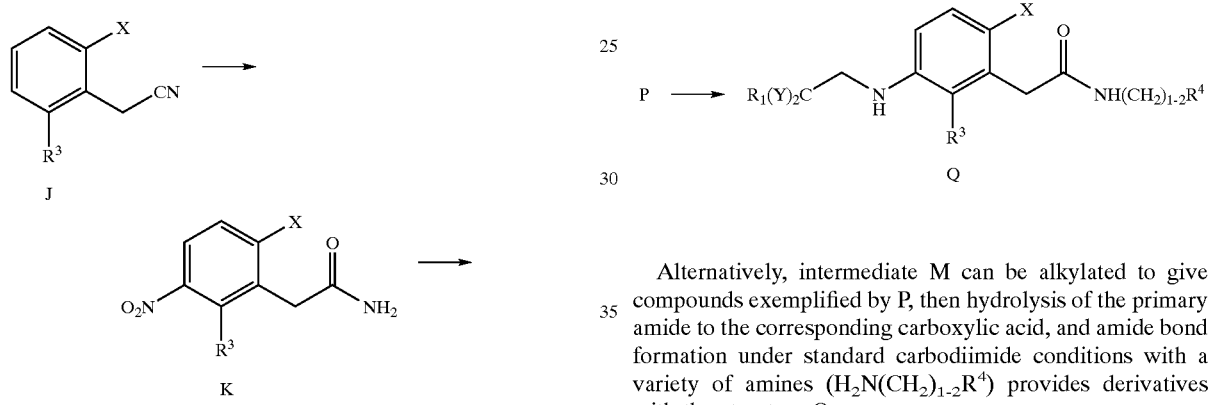

Alternatively, intermediate M can be alkylated to give compounds exemplified by P, then hydrolysis of the primary amide to the corresponding carboxylic acid, and amide bond formation under standard carbodiimide conditions with a variety of amines $(H_2N(CH_2)_{1-2}R^4)$ provides derivatives with the structure Q.

Specific scheme

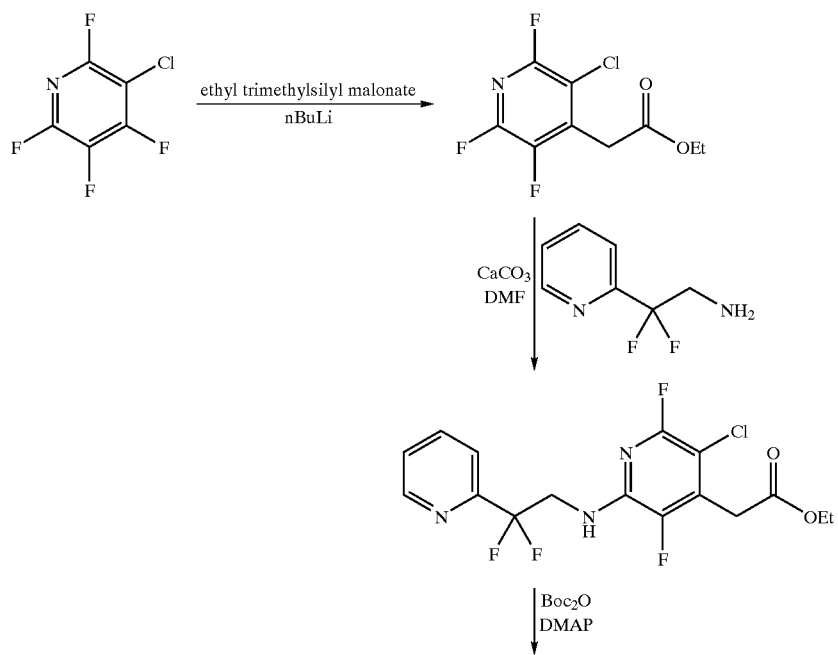

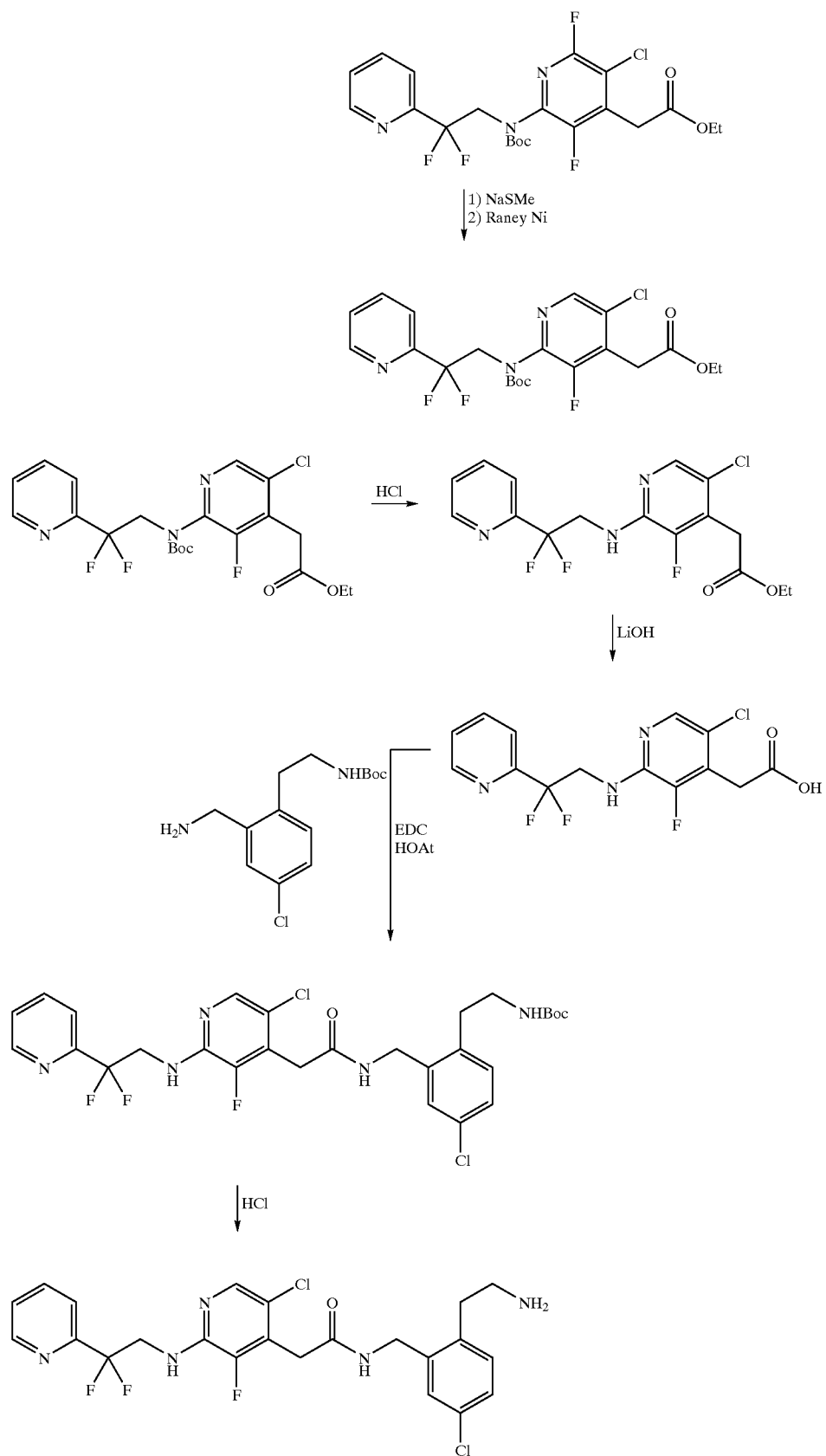

Intermediate compounds useful for preparing compounds of the invention are described in Examples I-1 through I-27.

EXAMPLE I-1

3-Fluoro-2-pyridylmethyl-3-(2,2-difluoro-2-(2-pyridyl)ethylamino)-6-methylpyrazin-2-one-1-acetamide

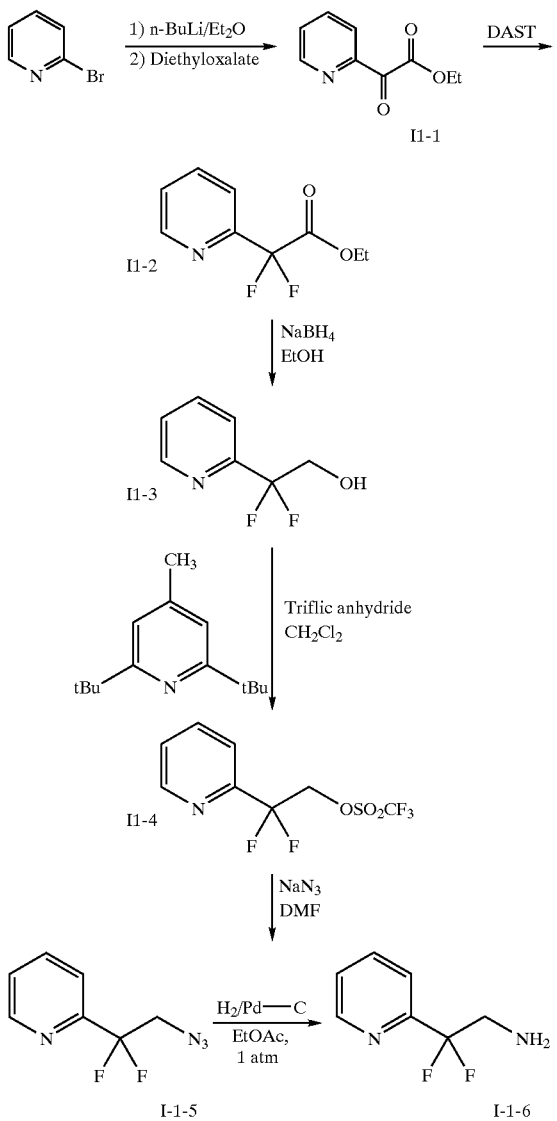

The synthesis of the 2,2-difluoro-2-(2-pyridyl)ethylamine I-1-6 involves generation of 2-lithiopyridine from 2-bromopyridine in ether, followed by reaction with diethyl oxalate to give the 2-pyridylketoester I-1-1. Treatment with excess diethylaminosulfurtrifluoride provides ethyl difluoro-2-pyridylacetate I-1-2 which is reduced without purification using sodium borohydride. The resulting 2,2-difluoro-2-pyridylethanol I-1-3 is purified by chromatography and converted to the corresponding triflate I-1-4 using triflic anhydride and 2,6-di-t-butyl-4-methylpyridine as the base. The crude triflate is then treated with sodium azide in DMF to give 2,2-difluoro-2-pyridylethyl azide I-1-5 which is also purified by silica gel chromatography. Reduction of the azide by catalytic hydrogenation provides the 2,2-difluoro-2-pyridylethylamine I-1-6.

Ethyl 2-pyridinoylformate (I-1-1)

To a stirred solution of 20 mL (210 mmol) of 2-bromopyridine in 500 mL of dry ether at −78° C. under Ar was added 85 mL of a 2.5 M solution of n-butyllithium in hexane in a slow stream. After stirring in the cold for 30 min, the solution was transferred over a 5 min period via two cannula into a 0° C. stirred solution of 100 mL (736 mmol) of diethyl oxalate in 1.0 L of dry ether under Ar. After stirring for 2 h in the cold, the reaction mixture was washed with 600 mL of sat. NaHCO$_3$, water, and brine. The solution was dried over MgSO$_4$ and the solvents concentrated at reduced pressure to give a red oil that was purified by SiO$_2$ chromatography (10×15 cm) using 1:4 to 35:65 EtOAc-hexanes. The product-containing fractions were concentrated at reduced pressure to afford I-1-1 as a reddish oil: $^1$H NMR (CDCl$_3$) δ1.42 (t, 3H), 4.45–4.55 (m, 2H), 7.55–7.6 (m, 1H), 7.9–7.95 (m, 1H), 8.11 (d, 1H), 8.78 (d, 1H).

Ethyl difluoro-2-pyridylacetate (I-1-2)

A stirred solution of 22 g (123 mmol) of ethyl 2-pyridinoylformate I-1-1 and 75 g (465 mmol) of diethylaminosulfurtrifluoride (DAST) were heated to 55° C. under Ar overnight. Because the reaction was not complete, 5 g additional DAST was added, and the reaction heated for an additional 24 h. The reaction mixture was cooled to rt, and poured very slowly into a stirred mixture of 1 kg of ice, 400 mL of ethyl acetate and 500 mL of sat. NaHCO$_3$. After the addition, the mixture was basified by the addition of solid NaHCO$_3$. The aqueous layer was extracted with EtOAc, and the combined organic layers washed with sat. NaHCO$_3$, brine, dried over Na$_2$SO$_4$ and the solvents concentrated at reduced pressure to give I-1-2 as a brown oil: $^1$H NMR (CDCl$_3$) δ1.35 (t, 3H), 4.35–4.4 (m, 2H), 7.4–7.45 (m, 1H), 7.75 (d, 1H), 7.95 (d, 1H), 8.45 (d, 1H).

2,2-Difluoro-2-(2-pyridyl)ethanol (I-1-3)

To a stirred solution of 19.5 g (97 mmol) of ethyl difluoro-2-pyridylacetate I-1-2 in 200 mL of absolute ethanol at 0° C. was added 4.42 g (116 mmol) of sodium borohydride in small portions. After 30 min, the reaction was quenched by the addition of 50 mL of sat. NH$_4$Cl. The reaction mixture was concentrated at reduced pressure and the residue partitioned between 500 mL of ethyl acetate and sat. NaHCO$_3$. The organic layer was washed with water, brine, and dried over Na$_2$SO$_4$ and concentrated at reduced pressure to give a brown oil that was purified on SiO$_2$ (10×17 cm) using 1:1 EtOAc-hexane. After re-chromatographing the mixed fractions, all clean fractions were combined and concentrated at reduced pressure, giving I-1-3 as a beige crystalline solid: $^1$H NMR (CDCl$_3$) δ3.6 (t, 1H), 4.17–4.3 (m, 2H), 7.4–7.45 (m, 1H), 7.73 (d, 1H), 7.84–7.91 (m, 1H), 8.61 (d, 1H).

2,2-Difluoro-2-(2-pyridyl)ethyl trifluoromethanesulfonate (I-1-4)

To a stirred solution of 5 g (31.4 mmol) of 2,2-difluoro-2-(2-pyridyl)ethanol I-1-3 and 9.69 g (47.2 mmol) of 2,6-di-t-butyl-4-methylpyridine in 110 mL of methylene chloride at −78° C. under Ar was added 7.93 mL (47.2 mmol) of triflic anhydride dropwise. After 1 h, the reaction was diluted with 100 mL of pentane and filtered. The filtrate was concentrated and treated again with pentane and filtered. Concentration of the filtrate gave I-1-4 as a brown oil, contaminated with 2,6-di-t-butyl-4-methylpyridine: $^1$H NMR (CDCl$_3$) δ5.12 (t, 2H), 7.45–7.5 (m, 1H), 7.75 (d, 1H), 7.86–7.94 (m, 1H), 8.65 (d, 1H).

2,2-Difluoro-2-(2-pyridyl)ethylazide (I-1-5)

To a stirred solution of 5.5 g of 2,2-difluoro-2-(2-pyridyl) ethyl trifluoromethanesulfonate I-1-4 in 70 mL of DMF was added 6.74 g (104 mmol) of sodium azide under Ar. The mixture was heated to 60° C. overnight. A second batch was run in the same manner, and after cooling to rt, both reactions were poured into 600 mL of water, and extracted with 3×500 mL of ether. The combined extracts were washed with brine, dried over $Na_2SO_4$ and concentrated at reduced pressure to give an oil that was purified by $SiO_2$ (10×6 cm) using hexane 1:3 EtOAc-hexane and 1:1 EtOAc-hexane. The product-containing fractions were concentrated at reduced pressure to give I-1-5 as a yellow oil: $^1$H NMR (CDCl$_3$) δ4.05 (t, 2H), 7.4–7.45 (m, 1H), 7.73 (d, 1H), 7.83–7.89 (m, 1H), 8.67 (d, 1H).

2,2-Difluoro-2-(2-pyridyl)ethylamine (I-1-6)

A stirred solution of 100 mg of 2,2-difluoro-2-(2-pyridyl) ethylazide I-1-6 was hydrogenated in 10 mL of ethyl acetate over 100 mg of 10% palladium on carbon using a balloon for 1 h. The catalyst was removed by filtration and the solvents removed at reduced pressure. A total of 1.8 g (9.7 mmol) of the azide was reduced using this procedure to give I-1-6 as a yellow oil: $^1$H NMR (CDCl$_3$) δ8.66 (d, 1H, 4.2 Hz), 7.82 (td, 1H, 7.7, 1.7 Hz), 7.68 (d, 1H, 8.1 Hz), 7.37–7.40 (m, 1H), 3.44 (t, 2H, 14.3 Hz), 1.41 (br s, 2H).

EXAMPLE I-2

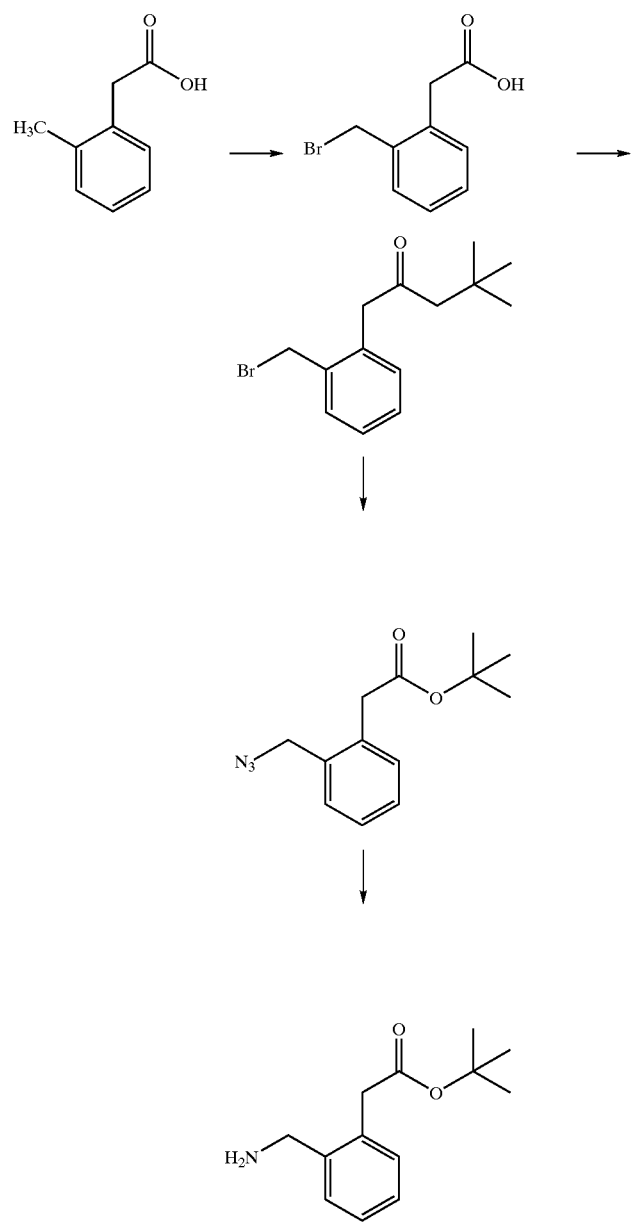

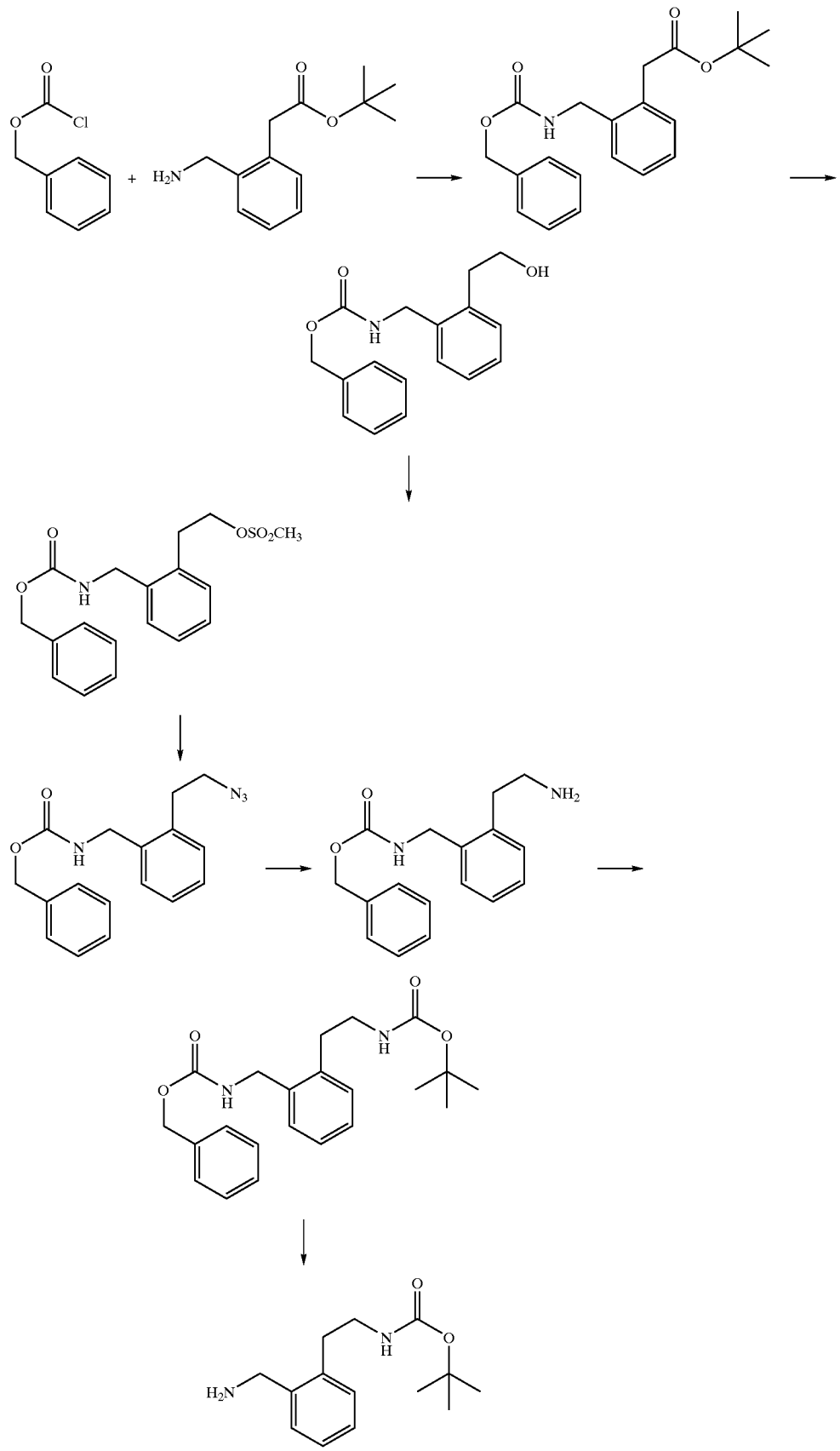
-continued tert-Butyl 2-[2-(aminomethyl)phenyl]ethylcarbamate

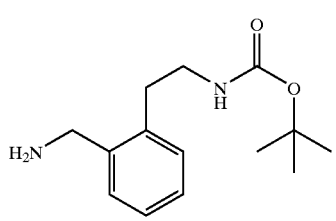

Step A. 2-Bromomethylphenylacetic acid

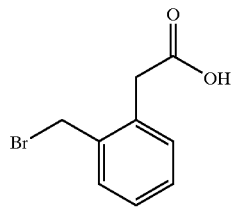

To a solution of 97.0 g (0.646 mol) o-tolylacetic acid in 1.75 L carbon tetrachloride was added 115.0 g (0.646 mol) N-bromosuccinimide and 3.4 g (0.021 mol) 2,2'-azobisisobutyronitrile. The mixture was heated at reflux under a nitrogen atmosphere for 4 h. After the mixture was cooled to 0–5° C. for 30 min, the solids were removed by filtration and washed with a small portion of carbon tetrachloride. This solid was triturated with water (0.8 L), collected on a filter, and washed with 500 mL of water to give 2-bromomethylphenylacetic acid. The filtrate was concentrated to a volume of 150 ml, and the resulting slurry cooled to 0–5° C. for 30 min. A second batch of product was obtained.

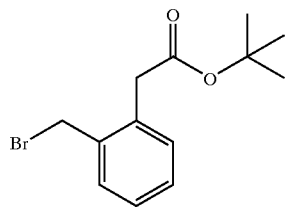

Step B. 2-Bromomethylphenylacetic acid t-butyl ester

To a solution of 80 g (0.349 mol) 2-bromomethylphenylacetic acid in 700 mL 1,4-dioxane in a 2 L heavy-walled flask was added 84 mL (1.571 mol) concentrated sulfuric acid at ambient temperature. The reaction mixture was chilled to −15° C., and 580 mL isobutylene was condensed directly into the reaction vessel. The sealed pressure flask was shaken mechanically at room temperature for 4 h (the pressure inside the flask rises to ca. 20 psi during this step). The mixture was carefully quenched by slowly pouring it into a 0–5° C. stirred mixture of 1.2 L tert-butyl methyl ether and 336 g (4.0 mol) solid sodium bicarbonate before slow dilution with 1.2 L ice-water. The separated organic phase was washed with 0.8 L brine, dried with sodium sulfate, filtered concentrated in vacuo to give an oil, which was used without further purification.

Step C. 2-Azidomethylphenylacetic acid t-butyl ester

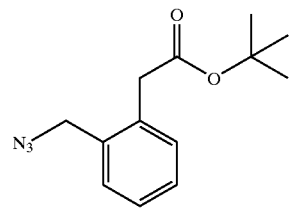

To a solution of crude 2-bromomethylphenylacetic acid t-butyl ester (0.349 mol) in 600 mL DMF was added 34.1 g (0.524 mol) sodium azide and the mixture stirred at 65° C. for 3 h. After cooling to ambient temperature, the mixture was diluted with 1.2 L ethyl acetate. The organic layer was washed with water (3×800 mL), dried over sodium sulfate, filtered and concentrated in vacuo to give the titled compound as a yellow oil. This material was used without further purification.

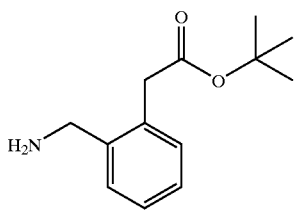

Step D. tert-Butyl [2-(aminomethyl)phenyl]acetate oxalate salt

To a solution of 78.0 g (0.312 mol) 2-azidomethylphenylacetic acid t-butyl ester in 1.36 L TBF was added 7.8 g (50% water wet) 5% Pd on C and the mixture shaken mechanically in a 2 L heavy-walled flask under H₂ at 45 psi for 2 h. The catalyst was removed by filtration through a bed of celite, rinsing with 250 mL THF. To the filtrate was added a solution of 31.25 g (0.347 mol) oxalic acid in 500 mL methyl tert-butyl ether, and the resultant suspension stirred at room temperature for 30 min. The solid was collected on a filter and washed with 300 mL methyl tert-butyl ether (the filtration was very slow, requiring about 3 hours). Drying under reduced pressure at 60° C. for 18 h gave 42.4 g (39% overall from 2-bromomethylphenylacetic acid) tert-butyl [2-(aminomethyl)phenyl]acetate oxalate salt as a white powder. The product is unstable as the free base, and will cyclize to the amide over several hours at room temperature.

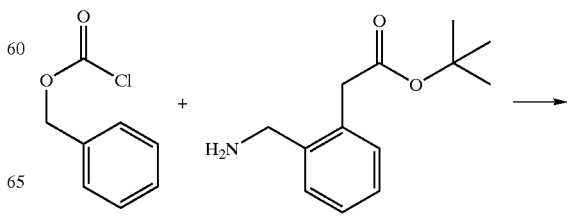

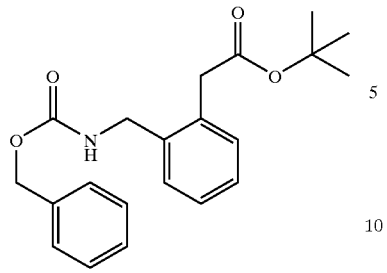

Step E. tert-Butyl [2-({[(benzyloxy)carbonyl]amino}methyl)phenyl]acetate

To a solution of 3.0 g (9.64mmol) tert-butyl [2-(aminomethyl)phenyl]acetate in 100 mL methylene chloride cooled to 0° C. was added 0.825 ml (5.78 mmol) benzyl chloroformate followed by 1.47 g (12.05 mmol) of 4-dimethylaminopyridine and a second 0.825 ml (5.78 mmol) portion of benzyl chloroformate. After 30 min the reaction was washed with 10% potassium hydrogen sulfate (aq) (2×30 mL), water (1×30 mL), and brine (1×30 mL), dried over sodium sulfate, filtered and concentrated to dryness in vacuo. The resulting crude oil (3.69 g) was flash chromatographed on silica gel (15% ethyl acetate in hexane) to give tert-butyl [2-({[(benzyloxy)carbonyl]amino}methyl)phenyl]acetate as a colorless oil: $^1$H NMR (CDCl$_3$, 400 MHz): δ7.38–7.30 (m, 5H), 7.28–7.21 (m, 4H), 5.40 (br s, 1H), 5.12 (s, 2H), 4.40 (d, 2H, J=5.5 Hz), 3.61 (s, 2H), 1.41 (s, 9H); MS (Electrospray): M+Na=378.1; TLC R$_f$=0.30 (15% ethyl acetate in hexane).

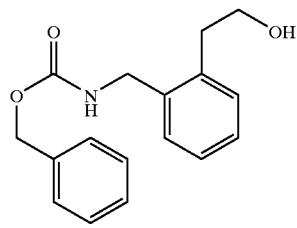

Step F. Benzyl 2-(2-hydroxyethyl)benzylcarbamate

To a solution of 3.15 g (8.86 mmol) tert-butyl [2({[(benzyloxy)carbonyl]amino}methyl)phenyl]acetate in 32 mL of THF cooled to 0° C. and under a nitrogen atmosphere was added dropwise 6.65 mL of a 2.0M lithium borohydride solution in THF over 30 min. After stirring overnight at room temperature, the reaction was cooled in an ice bath and treated with 10% potassium hydrogen sulfate (aq) portionwise until fizzing subsided and extracted with ethyl acetate (3×). The organic extracts were combined, washed with brine (1×), dried over sodium sulfate, filtered and concentrated to dryness in vacuo to give 2.58 g of a crude light yellow oil. Flash chromatography on silica gel (linear gradient from 5 to 40% ethyl acetate in hexane) gave benzyl 2-(2-hydroxyethyl)benzyl carbamate as a colorless oil: $^1$H NMR (CDCl$_3$, 400 MHz): δ7.37–7.19 (m, 9H), 5.44 (br s, 1H), 5.12 (s, 2H), 4.42 (d, 2H, J=5.2 Hz), 3.90–3.82 (br t, 2H), 2.95–2.88 (br t, 2H, J=5.2 Hz); MS (Electrospray): M+Na=308.1; TLC R$_f$=0.28 (40% ethyl acetate in hexane).

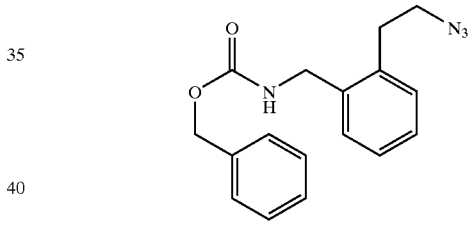

Step G. 2-[2-({[(Benzyloxy)carbonyl]amino}methyl)phenyl]ethyl methanesulfonate To a solution of 1.06 g (3.72 mmol) benzyl 2-(2-hydroxyethyl)benzyl carbamate in 10 mL of methylene chloride cooled to 0° C. was added 0.570 mL (4.09 mmol) of triethylamine followed by 0.316 mL (4.09 mmol) of methanesulfonyl chloride. After stirring overnight at room temperature, the reaction was flash chromatographed directly on silica gel (40% ethyl acetate in hexane) to give 2-[2-({[(benzyloxy)carbonyl]amino}methyl)phenyl]ethyl methanesulfonate as a colorless oil: $^1$H NMR (CDCl$_3$, 400 MHz): δ7.38–7.21 (m, 9H), 5.21 (br s 1H), 5.13 (s, 2H), 4.45–4.38 (m, 4H), 3.12 (br t, 2H, J=6.7 Hz), 2.84 (s, 3H); MS (Electrospray): M+Na=386.0; TLC R$_f$=0.35 (40% ethyl acetate in hexane).

Step H. Benzyl 2-(2-azidoethyl)benzylcarbamate

To a solution of 1.15 g (3.16 mmol) of 2-[2-({[(benzyloxy)carbonyl]amino}methyl)phenyl]ethyl methanesulfonate in 8.0 mL of DMF was added 0.411 g (6.33 mmol) of sodium azide. After stirring at room temperature overnight, an additional 0.205 g (3.15 mmol) of sodium azide was added and the reaction warmed to 40° C. for 4 h. The reaction was cooled to room temperature, treated with saturated sodium carbonate (aq) and extracted with ethyl acetate (3×). The organic extracts were combined, washed with water (1×) and brine (1×), dried over sodium sulfate and concentrated to dryness in vacuo to give 1.2 g of a crude oil. Flash chromatography on silica gel (20% ethyl acetate in hexane) gave benzyl 2-(2-azidoethyl)benzylcarbamate as a colorless oil: $^1$H NMR (CDCl$_3$, 400 MHz): δ7.39–7.20 (m, 9H), 5.14 (s, 2H), 5.05 (br s, 1H), 4.42 (d, 2H, J=5.6 Hz), 3.56–3.49 (t, 2H, J=7.0 Hz), 2.91 (t, 2H, J=7.0 Hz); MS (Electrospray): M+Na=333.1; TLC R$_f$=0.32 (20% ethyl acetate in hexane).

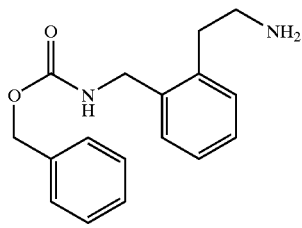

Step I. Benzyl 2-(2-aminoethyl)benzylcarbamate

To a solution of 904 mg (2.91 mmol) benzyl 2-(2-azidoethyl)benzyl carbamate in 40.0 mL THF containing 4.0 mL water was added 1.53 g (5.28 mmol) triphenylphosphine and the reaction stirred at room temperature overnight. The THF was removed in vacuo and the residual aqueous phase extracted with methylene chloride (3×). The organics were combined, washed with brine (1×), dried over sodium sulfate, filtered and concentrated to dryness in vacuo. Flash chromatography on silica gel (linear gradient from 160/10/1 to 114/10/1 of methylene chloride/methanol/concentrated ammonium hydroxide) gave benzyl 2-(2-aminoethyl) benzylcarbamate as a colorless oil: $^1$H NMR (CDCl$_3$, 400 MHz): δ7.38–7.17 (m, 9H), 6.14 (br s, 1H), 5.12 (s, 2H), 4.41 (d, 2H, J=4.5 Hz), 3.01–3.95 (t, 2H, J=6.7 Hz), 2.82–2.75 (t, 2H, J=6.7 Hz); MS (Electrospray): M+H=285.1; TLC R$_f$=0.18 (160/10/1 of methylene chloride/methanol/concentrated ammonium hydroxide).

Step J. Benzyl 2-{2-[(tert-butoxycarbonyl)amino]ethyl}benzylcarbamate

To a solution of 584 mg (2.05 mmol) benzyl 2-(2-aminoethyl)benzyl carbamate in 6.0 mL of methylene chloride at 0° C. was added a 3.0 mL methylene chloride solution of 493 mg (2.26 mmol) di-tert-butyldicarbonate. The reaction was stirred 0.5 h at 0° C. and then warmed to room temperature for 2 h. Flash chromatography of the reaction directly onto silica gel (6% diethylether in methylene chloride) gave benzyl 2-{2-[(tert-butoxycarbonyl)amino]ethyl}benzylcarbamate as a colorless oil: $^1$H NMR (CDCl$_3$, 400 MHz): δ7.38–7.15 (m, 9H), 5.56 (br s, 1H), 5.13 (s, 2H), 4.67 (br s 1H), 4.41 (d, 2H, J=5.8 Hz), 3.34–3.27 (m, 2H), 2.88–2.80 (br t, 2H, J=7.0 Hz), 1.42 (s, 9H); MS (Electrospray): M+Na=407.1; TLC R$_f$=0.42 (5% diethyl ether in methylene chloride).

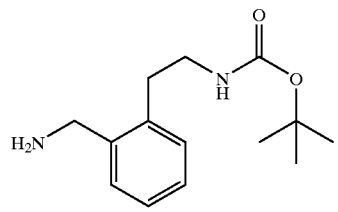

Step K. tert-Butyl 2-[2-(aminomethyl)phenyl]ethylcarbamate

To a solution of 750 mg (1.95 mmol) benzyl 2-{2-[(tert-butoxycarbonyl) amino]ethyl}benzylcarbamate in 6.0 mL absolute ethanol was added 150 mg of 10% palladium on carbon catalyst. A balloon of hydrogen was bubbled into the stirring suspension at room temperature over 2 h. The reaction was filtered through celite and the filter pad washed with fresh absolute ethanol (2×). The filtrate was concentrated to dryness in vacuo to give tert-butyl 2-[2-(aminomethyl)phenyl]ethylcarbamate as a colorless oil: $^1$H NMR (CDCl$_3$, 400 MHz): δ7.31–7.19 (m, 4H), 5.68 (br s, 1H), 3.90 (s, 2H), 3.41–3.34 (br m, 2H), 2.90–2.83 (br t, 2H, J=6.8 Hz), 1.41 (s, 9H); MS (Electrospray): M+NH=251.1; TLC R$_f$=0.24 (160/10/1 of methylene chloride/methanol/concentrated ammonium hydroxide).

EXAMPLE I-3

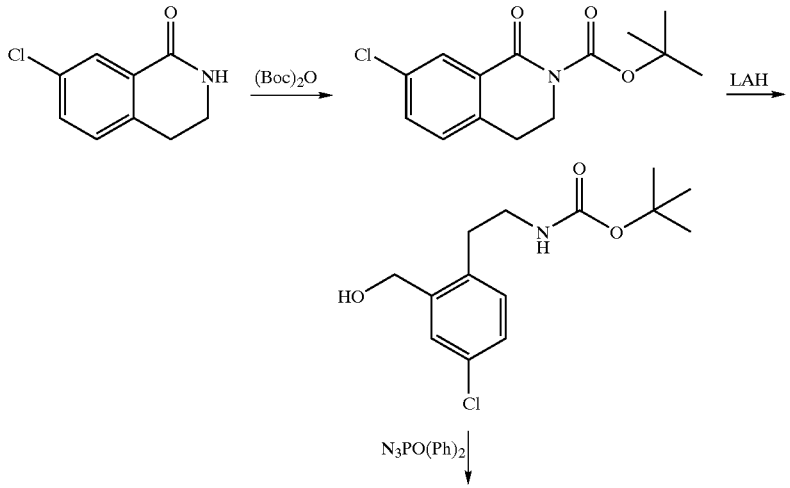

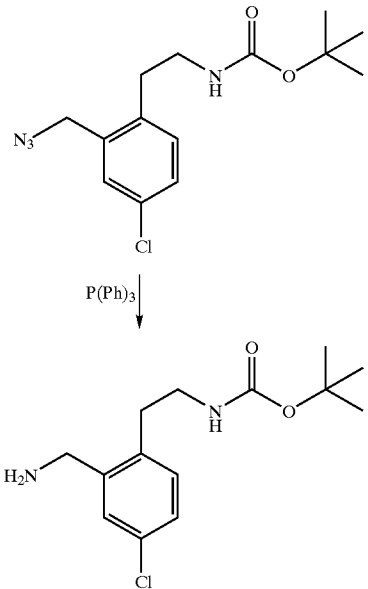

tert-Butyl 2-[2-(aminomethyl)-4-chlorophenyl]ethylcarbamate

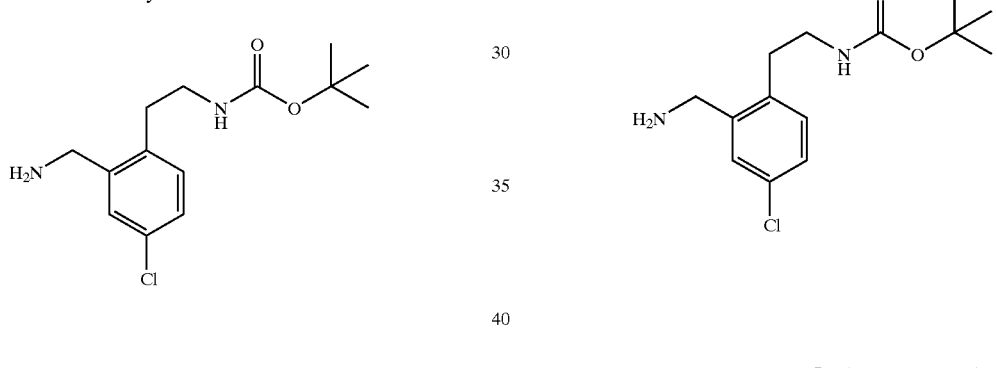

Step A. tert-Butyl 2-[2-azidomethyl)-4-chlorophenyl]ethylcarbamate

Step B. tert-Butyl 2-[2-(aminomethyl)-4-chlorophenyl]ethylcarbamate

To a solution of 649 mg (2.27 mmol) tert-butyl 2-[4-chloro-2-(hydroxymethyl)phenyl]ethylcarbamate in 5.0 mL THF at 0° C. was added 0.674 mL (3.13 mmol) of diphenylphosphoryl azide (DPPA) and 0.468 mL (3.13 mmol) of 1,8-diazabicyclo[5.4.0]undec-7-ene (DBU) and the reaction stirred at 0° C. for 10 min, then at room temperature. After 3 h the reaction was treated with saturated sodium carbonate (aq) and extracted with ethyl acetate (3×). The organic extracts were combined, washed with brine (1×), dried over sodium sulfate, filtered and concentrated to dryness in vacuo to give 963 mg of a crude oil. Flash chromatography on silica gel (15% ethyl acetate in hexane) gave tert-butyl 2-[2-azidomethyl)-4-chlorophenyl]ethylcarbamate as a colorless oil: $^1$H NMR (DMSO-d$_6$, 400 MHz): δ7.44 (d, 1H, J=1.8 Hz), 7.36 (dd, 1H, J=2.0 and 8.2 Hz), 7.26 (d, 1H, J=8.1 Hz), 6.92 (br t, 1H, J=5.5 Hz), 4.53 (s, 2H), 3.10 (dt, 2H, J=6.3 and 7.6 Hz), 2.73 (t, 2H, J=7.3 Hz), 1.36 (s, 9H); MS (Electrospray): M+Na=333.0; TLC R$_f$=0.32 (15% ethyl acetate in hexane).

To a solution of 629 mg (2.02 mmol) tert-butyl 2-[2-azidomethyl)-4-chlorophenyl]ethylcarbamate in 30.0 mL THF containing 3.1 mL water was added 1.06 g (4.05 mmol) triphenylphosphine and the reaction stirred at room temperature overnight. The THF was removed in vacuo and the residual aqueous phase extracted with methylene chloride (3×). The organics were combined, washed with brine (1×), dried over sodium sulfate, filtered and concentrated to dryness in vacuo. Flash chromatography on silica gel (linear gradient from 266/10/1 to 200/10/1 of methylene chloride/methanol/concentrated ammonium hydroxide) gave tert-butyl 2-[2-(aminomethyl)-4-chlorophenyl]ethylcarbamate as a colorless oil: $^1$H NMR (DMSO-d$_6$, 400 MHz): δ7.45 (d, 1H, J=1.7 Hz), 7.18 (dd, 1H, J=2.1 and 8.2 Hz), 7.12 (d, 1H, J=8.2 Hz), 7.01 (br t, 1H, J=5.2 Hz), 3.73 (s, 2H), 3.07 (dt, 2H, J=6.5 and 7.3 Hz), 2.68 (t, 2H, J=7.4 Hz), 1.36 (s, 9H); MS (Electrospray): M+H=285.1; TLC R$_f$=0.33 (160/10/1 of methylene chloride/methanol/concentrated ammonium hydroxide).

EXAMPLE I-4

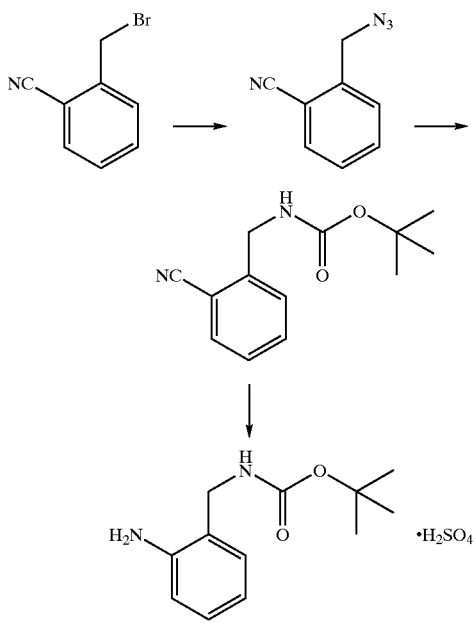

tert-Butyl 2-(aminomethyl)benzylcarbamate

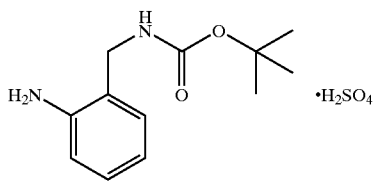

Step A. 2-(Azidomethyl)benzonitrile

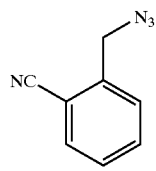

To a solution of 90 g (459 mmol) 2-cyanobenzylbromide in 600 mL THF was added in one portion a solution of 36 g (553 mmol) sodium azide in 100 mL water. The two phase mixture was stirred at 23° C. for 18 hr. The THF layer was separated from the lower water layer and used in the next step without further purification.

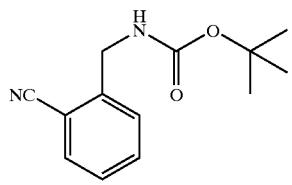

Step B. tert-Butyl 2-cyanobenzylcarbamate

To the THF layer from the previous step was diluted to a volume of 1.6 L, divided into two equal portions and each hydrogenated at 45 psi in a Parr pressure bottle containing 6 g of 5% palladium on carbon (50% water by weight). A 5–10° C. exotherm was observed within 30 min and shaking continued a total of 1.5 hr. The individual batches were filtered through celite, washed 2× with 100 mL fresh THF and the filtrates combined into a single portion. To the amine mixture without concentration (Caution: attempts to concentrate the solution resulted in a large exotherm and the batch turned black) was added 87.5 mL (381 mmol) of di-tert-butyl dicarbonate neat. After 2 hr the THF was removed in vacuo and flushed with 250 mL of 15% ethyl acetate in hexane. The semi-solid was slurried in 250 mL of 15% ethyl acetate and filtered. The filtrate was concentrated in vacuo, diluted with 10% ethyl acetate in hexane (175 mL), cooled to 0° C. and filtered to give tert-butyl 2-cyanobenzylcarbamate as a gray solid.

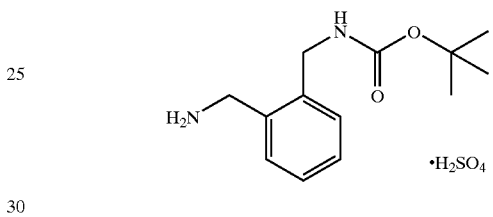

Step C. tert-Butyl 2-(aminomethyl)benzylcarbamate hemisulfate

To a 3 L, 3 neck flask fitted with a thermocouple, a condenser and nitrogen inlet was added 3 g (23 mmol) of cobaltous chloride, then 1200 mL of THF followed by 59 g (254 mmol) of tert-butyl 2-cyanobenzylcarbamate and 600 mL of ice-water. To the light pink solution at 15° C. was added 26 g (684 mmol) of sodium borohydride in portions as follows. The initial 3 g of sodium borohydride resulted in a vigorous hydrogen gas evolution and formation of a black suspension. The batch temperature reached 35° C. within 2 hr, and was maintained at this temperature with a heating mantle. Additional sodium borohydride and cobaltous chloride were added as needed to drive the reaction to completion. Typically, 2×7.5 g of additional sodium borohydride and 2×1 g portions of cobaltous chloride were added at 12 hour intervals. Once complete, the layers were allowed to settle and the clear upper THF layer was decanted from the black aqueous layer. The aqueous layer was washed with 750 mL fresh THF, the two THF layers combined and filtered through a pad of celite. The orange-yellow filtrate was concentrated to about 300 mL in vacuo, resulting in water layer with the product as an oily lower layer. The mixture was extracted with 2×250 mL ethyl acetate and the combined extracts reacted with 24 g (200 mmol) of solid sodium hydrogensulfate. A solid formed immediately, and the slurry was stirred for 30 min, filtered and washed with 2×100 mL ethyl acetate to give 62 g of a white powder. The powder was slurried in 175 mL water, cooled to 0° C., filtered, washed with 2×40 mL cold water and the solid dried in a vacuum oven at 55° C. for 24 hr to give tert-butyl 2-(aminomethyl)benzylcarbamate hemisulfate salt as a white powder.

EXAMPLE I-5

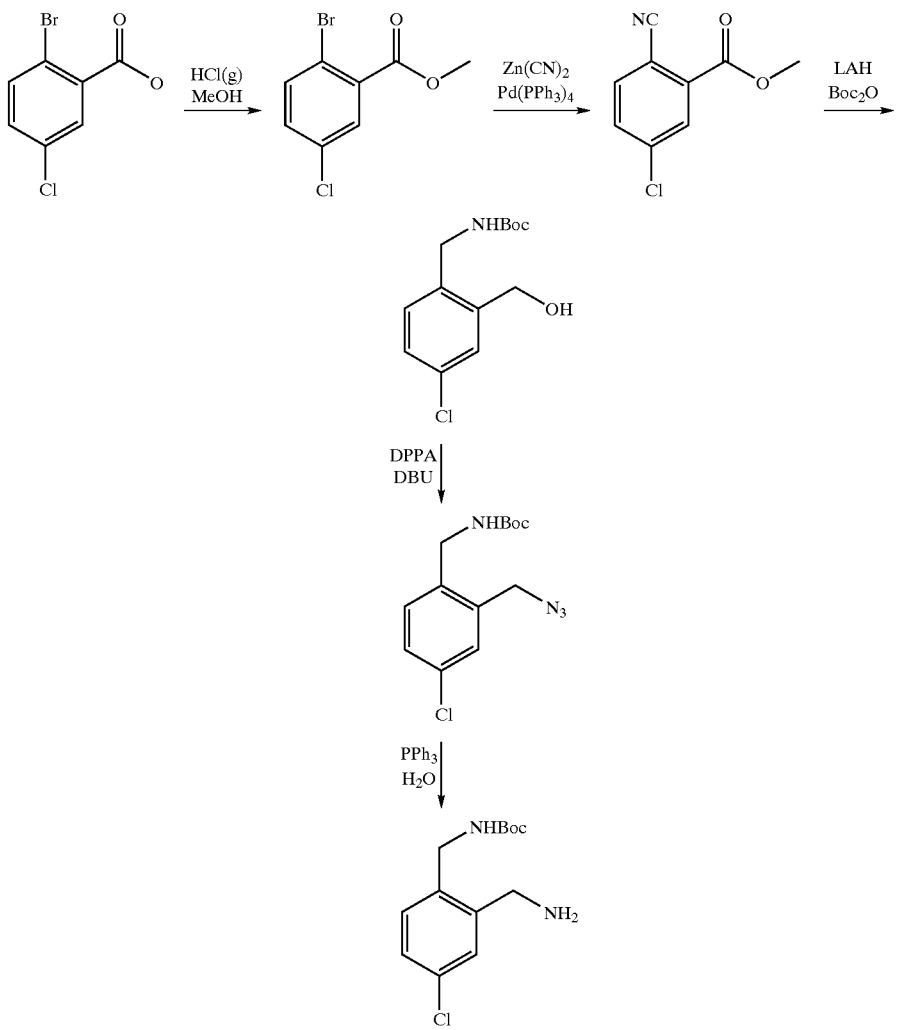

EXAMPLE I-5 tert-Butyl 2-(aminomethyl)-4-chlorobenzylcarbamate

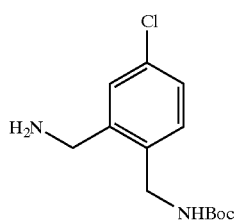

Step A. 2-bromo-5-chlorobenzoate

Through a solution of 2-bromo-chlorobenzoic acid 11 g, 46.7 mmol) in methanol (250 ml) was bubbled HCl gas. The reaction was allowed to warm to room temperature and stirred overnight. The reaction mixture is concentrated in vacuo to give an orange oil, which is purified by flash chromatography (silica gel, hexane) to give the title compound as a colorless oil.

1H NMR (CDCl$_3$, 400MHz): δ7.78 (d, 1H, J=2.6 Hz); 7.59 (d, 1H, J=12.81 Hz); 7.30 (dd, 1H, J=8.6, 2.5 Hz); 3.94 (s, 3H)

Step B. Methyl 5-chloro-2-cyanobenzoate

To a solution of methyl 2-bromo-5-chlorobenzoate (1.15 g, 4.6 mmol) in degassed DMF was added zinc cyanide (282 mg, 2.40 mmol) and palladium tetrakis triphenylphosphine (100 mg, 0.086 mmol) and the reaction is stirred at 90° C. over night. The reaction was partitioned between ethyl acetate and water. The organic was concentrated in vacuo and purified by flash chromatography eluting a gradient to 10 to 25% ethyl acetate in hexane yielding a white solid (methyl 5-chloro-2-cyanobenzoate).

H NMR (CDCl$_3$, 400 MHz): δ8.13 (d, 1H, J=1.83 Hz); 3.09 (d, 1H, J=8.24 Hz); 7.29 (dd, 1H, J=8.34, 2.10 Hz); 4.02 (s, 3H)

Step C. [2-(aminomethyl)-5-chlorophenyl]methanol

To LAH (1 M/Et$_2$O, 104.4 ml, 104.4 mmol) in anhydrous THF (300 ml) at 0° C. was added methyl 5-chloro-2-cyanobenzoate (9.28 g, 0.512 mmol) maintaining the temperature below 20° C. After one half hour, quenched at OC with water (3.97 ml), NaOH (1N, 11.9 ml, 11.9 mmol) and water (3.97 ml). A precipitate was filtered out and washed with THF. The filtrate was concentrated in vacuo and was used immediately in the next step.

H NMR (CDCl$_3$, 400 MHz): δ7.17–7.36 (m, 3H); 4.60 (s, 2H); 3.98 (s, 2H);

Step D. tert-butyl 4-chloro-2-(hydroxymethyl) benzylcarbamate

To a solution of [2-(aminomethyl)-5-chlorophenyl] methanol in dichloromethane (200 ml), was added di-tert-butyl-dicarbonate (11.38 g, 52.18 mmol) at room temperature. After one hour, the reaction was partitioned. The organic layer was concentrated in vacuo and purified by flash chromatography eluting a gradient of ethyl acetate/hexane which gave a brown oil, which was taken up in dichloromethane (500 ml) and treated with activated charcoal yielding a pink solid.

H NMR (CDCl$_3$, 400 MHz): 7.36 (s, 1H); 7.2–7.5 (m, 2H); 4.69 (b s, 2H); 4.32 (d, 2H, J=6.04 Hz); 1.43 (s, 9H).

Step E. tert-Butyl 2-(azidomethyl)-4-chlorobenzylcarbamate

To a solution of tert-butyl 4-chloro-2-(hydroxymethyl) benzylcarbamate (10 g, 36.8 mmol) in anhydrous THF (100 ml) was added DPPA (8.3 ml, 38.6 mmol) and DBU (5.79 ml, 38.6 mmol). The mixture was stirred overnight and then was partitioned between ethyl acetate and water. The organic layer was washed with brine, and was concentrated in vacuo to a crude oil (14.6 g). Purification was accomplished by silica gel chromatography, eluting a gradient of ethyl acetate-hexane (10, 15, 20, 25, 50%) to give tert-butyl 2-(aminomethyl)-4-chlorobenzylcarbamate.

H NMR (CDCl$_3$, 400 MHz): δ7.25–7.39 (m, 3H); 4.41 (s, 2H), 4.32 (d, 2H, J=5.86 Hz); 1.45 (s, 9H).

Step F. tert-Butyl 2-(aminomethyl)-4-chlorobenzylcarbamate

To a solution of tert-butyl 2-(azidomethyl)-4-chlorobenzylcarbamate (10.9 g, 36.73 mmol) in THF (60 ml) and water (6 ml) was added triphenylphospine (10.59 g, 40.40 mmol). The reaction was heated to 65 C. and stirred overnight at room temperature. The reaction was concentrated in vacuo and flashed with 4% (10% NH4OH/MeOH)/dichlor-omethane. A second purification using silica gel column chromatography with a careful gradient of 3 to 5% (10% NH4OH/MeOH)/dichloro methane gave the title compound.

H NMR (CDCl$_3$, 400 MHz) δ7.21–7.52 (m, 3H); 4.32 (b d, 2H); 3.90 (s, 2H); 1.44 (s, 9H).

EXAMPLE I-6

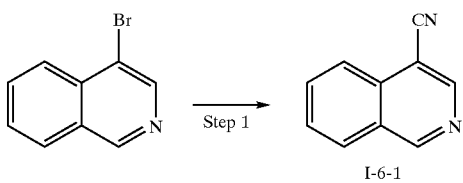

Step 1: 4-isoquinolinecarbonitrile (I-6-1)

To a mixture of 3.0442 g (14.63 mmol) 4-bromoisoquinoline, 1.0380 g (8.84 mmol) zinc cyanide and 1.0721 g (0.92 mmol) tetrakis(triphenylphosphine) palladium(0) was added 30 mL DMF. After 19 h under argon at 80° C., the reaction mixture was cooled to room temperature, diluted with 150 mL toluene and washed with 80 mL 2N NH$_4$OH and 40 mL brine. The organic layer was dried over Na$_2$SO$_4$, filtered and concentrated in vacuo. Purification by flash chromatography (75×110 mm silica gel, 1% MeOH:CH$_2$Cl$_2$) gave I-1-1. $^1$H NMR (CDC$_3$, 400 MHz) δ9.428 (s, 1H, ArH); 8.915 (s, 1H, ArH); 8.205 (d, 1H, J=8.41 Hz, ArH); 8.113 (d, 1H, J=8.23 Hz, ArH); 7.970–7.929 (m, 1H, ArH); 7.818–7.778 (m, 1H, ArH); MS (Electrospray): m/z 155.0 (M$^+$H).

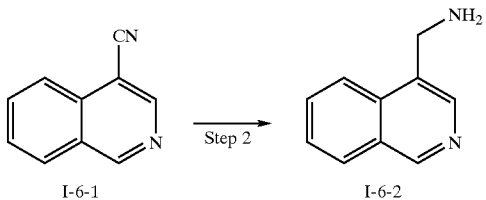

Step 2: 4-(aminomethyl)isoquinoline (I-6-2)

To a solution of 0.0934 g (0.61 mmol) I-6-1 in 3 mL NH$_3$ saturated EtOH was added a 1 mL slurry of Raney nickel (50 wt. % in EtOH). After 20.5 h under H$_2$ at atmospheric pressure, the reaction mixture was diluted with 50 mL EtOH and filtered over celite. The celite was washed with 200 mL EtOH, and the filtrate was concentrated in vacuo. Purification by flash chromatography (15×140 mm silica gel, 5% (10% NH$_4$OH:MeOH):CH$_2$Cl$_2$) produced I-6-2. $^1$H NMR (CDCl$_3$, 400 MHz) δ9.190 (s, 1H, ArH); 8.504 (s, 1H, ArH); 8.105 (d, 1H, J=8.50 Hz, ArH); 8.013 (d, 1H, J=8.13 Hz, ArH); 7.793–7.751 (m, 1H, ArH); 7.656–7.616 (m, 1H, ArH); 4.320 (s, 2H, ArCH$_2$); MS (Electrospray): m/z 159.0 (M$^+$H).

EXAMPLE I-7

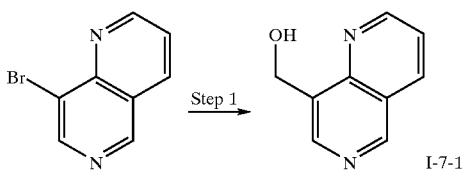

8-hydroxymethyl-1,6-napthyridine (I-7-1)

Through a solution of 3 g (14 mmol) 8-bromo-1,6-napthyridine in 700 mL DMF was passed a steady stream of CO gas for 1 h. To this was added 1.8 g (26 mmol) sodium formate and 1.5 g (2.1 mmol) (Ph$_3$P)$_2$PdCl$_2$. The resulting mixture was heated to 95° C. while continuing to bubble CO gas through the mixture for 4 h., then concentrated in vacuo. The residue was treated with 100 mL CH$_2$Cl$_2$ and filtered through celite (2×100 mL CH$_2$Cl$_2$ wash). The resulting filtrates were combined and concentrated to give 3.8 g orange oil that was taken up in 100 mL dry CH$_2$Cl$_2$ and cooled to −78° C. whereupon 14 mL (14 mmol, 1M solution in CH$_2$Cl$_2$) diisobutylalummium hydride was quickly added by syringe. The resulting mixture was stirred at −78° C. for 30 min., then poured into a well stirred mixture of 600 mL saturated aqueous sodium/potassium tartrate and 600 mL EtOAc, stirred at room temperature for 6 hours, then filtered through Celite. The layers were then separated and the aqueous layer extracted 3×400 mL EtOAc. The combined EtOAc extracts were dried over Na₂SO₄, filtered and concentrated in vacuo. Purification by flash chromatography (50×120 mm silica gel, linear gradient 3–8% MeOH:CH₂Cl₂) yielded 8-hydroxymethyl-1,6-napthyridine I-7-1. ¹H NMR (CDCl₃, 400 MHz) δ9.25 (s, 1H); 9.09 (dd, 1H, J=4.3 and 1.74 Hz); 8.68 (s, 1H); 8.35 (dd, 1H, J=8.3 and 1.74 Hz); 7.60 (dd, 1H, J=8.3 and 4.3 Hz); 5.22 (d, 2H, J=6.59 Hz); 4.42 (t, 1OH, J=6.58 Hz). Electrospray mass spectrum M+H=160.9.

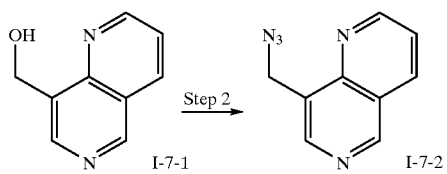

Step 2: 8-azidomethyl-1,6-napthyridine (I-7-2)

To a solution of 0.93 g (5.8 mmol) 8-hydroxymethyl-1,6-napthyridine in 20 mL THF was added 1.5 mL (7 mmol) DPPA and 1.2 mL (6.7 mmol) DBU. The reaction mixture was allowed to stir at room temperature 18 hours, then another 0.3 mL DPPA and 0.25 mL DBU were added and the reaction mixture heated to 50° C. for 8 hours then cooled to room temperature then another 0.3 mL DPPA and 0.25 mL DBU were added and the reaction mixture was allowed to stir 18 more hours at room temperature. The resulting solution was then diluted with 200 mL EtOAc, washed with saturated NaHCO₃ solution, and brine, dried over Na₂SO₄, filtered and concentrated in vacuo. Purification by flash chromatography (40×120 mm silica gel, linear gradient 2–15% MeOH:CH₂Cl₂) yielded 8-hydroxymethyl-1,6-napthyridine and 8-azidomethyl-1,6-napthyridine. ¹H NMR (CDCl₃, 400 MHz) δ9.30 (s, 1H); 9.16 (dd, 1H, J=4.3 and 1.8 Hz); 8.78 (s, 1H); 8.35 (dd, 1H, J=8.3 and 1.74 Hz); 7.61 (dd, 1H, J=8.3 and 4.3 Hz); 5.00 (s, 2H).

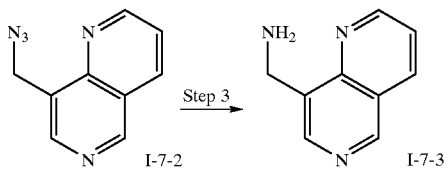

Step 3: 8-aminomethyl-1,6-napthyridine (I-7-3)

To a solution of 1.1 g (5.9 mmol) 8-azidomethyl-1,6-napthyridine in 20 mL THF was added 2 mL H₂O and 3 g PPh₃. The resulting solution was allowed to stir overnight at room temperature, then concentrated in vacuo. Purification by flash chromatography (50×140 mm silica gel, linear gradient 5–20% (10% NH₄H in MeOH):CH₂Cl₂) yielded 8-aminomethyl-1,6-napthyridine. ¹H NMR (CDCl₃, 400 MHz) δ9.22 (s, 1H); 9.13 (dd, 1H, J=4.3 and 1.8 Hz); 8.70 (s, 1H); 8.32 (dd, 1H, J=8.24 and 1.83 Hz); 7.61 (dd, 1H, J=8.24 and 4.3 Hz); 4.40 (s, 2H).

EXAMPLE I-8

Amides of 5-(aminomethyl)benzimidazole were Prepared as Follows

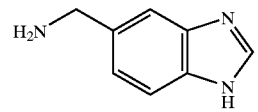

Step A: Ethyl-5-benzimidazole carboxylate

To a stirred solution of benzimidazole-5-carboxylic acid (Aldrich, 10 g, 61.7 mmol) in EtOH (200 mL) was added dropwise conc. H₂SO₄ (8 mL), and the solution was heated to reflux. After 1 h the solution was cooled to 60° C. and stirred for 16 h. The solution was then concentrated in vacuo and the residue was partitioned between EtOAc and saturated Na₂CO₃ solution. The layers were separated and the aqueous layer was extracted with EtOAc. The combined organic layers were washed with brine, dried (Na₂SO₄), and concentrated in vacuo to afford the title compound as a brown solid:

¹H NMR (400 MHz, CDCl₃): δ1.42 (t, J=7.1 Hz, 3H), 4.41 (q, J=7.1 Hz, 2H), 7.68 (d, J=8.4 Hz, 1H), 8.04 (dd, J=8.5 Hz, J=1.5 Hz, 1H), 8.23 (s, 1H), 8.43 (s, 1H); HRMS (FAB) C₁₀H₁₁N₂O₂ calcd. 191.2096 (M+1). Found 191.0541.

Step B: 5-(Hydroxymethyl)-benzimidazole

To a cooled (0° C.) suspension of ethyl-benzimidazole-5-carboxylate (4.76 g, 25 mmol) in CH₂Cl₂ (100 mL) was added a 1 M solution of DIBAL in CH₂Cl₂ (100 mL) and the mixture was stirred for 4 h. The reaction was quenched by the sequential addition of MeOH (8 mL), 1M NaOH (16 mL), and 30% sodium potassium tartrate (40 mL). The mixture was warmed to RT and filtered, and the solid residue was washed with CH₂Cl₂. The filtrate was concentrated in vacuo to afford the title compound as a brown solid: ¹H NMR (400 MHz, DMSO-d6): δ4.58 (s, 1H), 7.14 (m, 1H), 7.46 (s, 1H), 7.51 (m, 1H), 8.15 (s, 1H); HRMS (FAB) C₈H₉N₂O calcd. 149.1723 (M+1). Found 149.1045.

Step C: 5-(Azidomethyl)-benzimidazole

To a cooled (0° C.) suspension of 5-(hydroxymethyl)-benzimidazole (920 mg, 6.2 mmol) in THF (12 mL) was added sequentially DPPA (1.46 mL, 6.8 mmol) and DBU (1.11 mL, 7.4 mmol). The resulting solution was heated to reflux for 5 h, cooled to RT, and concentrated in vacuo. The residue was partitioned between sodium bicarbonate and ethyl acetate. The organic layer was washed with brine, dried (Na₂SO₄), and concentrated in vacuo. Silica gel chromatography (15% MeOH—CHCl₃), afforded the title compound as a brown solid: R_f (8:1:1 EtOAc-MeOH—NH₄H)= 0.31; m.p. 110–114° C.; ¹H NMR (400 MHz, DMSO-d6): δ8.25 (s, 1H), 7.27 (d, J=8.4, 1H), 7.62–7.60 (m, 2H), 7.20 (d, J=8.2 Hz, 1H), 8.24 (s, 1H); HRMS (FAB) C₈H₈N₅ calcd. 174.1847 (M+1). Found 174.1222.

Step D: 5-(Aminomethyl)-benzimidazole dihydrochloride

To a stirred solution of 5-(azidomethyl)benzimidazole (990 mg, 5.8 mmol) in THF (50 mL), was added Ph₃P (3.04 g, 11.6 mmol) followed by H₂O (99 μL) and the solution allowed to stir at RT for 16 h. The solution was concentrated in vacuo and EtOAc was added to the residue. The mixture was warmed gently until the solids dissolved. A saturated solution of HCl in EtOAc was added dropwise until precipitation began. The suspension was stirred for a few minutes to allow for complete precipitation and was filtered to afford the title compound as a white solid: $^1$H NMR (400 MHz, DMSO-d6): δ4.08 (s, 2H), 7.27 (d, J=8.4, 1H), 7.60 (d, J=6.2, 1H), 7.70 (s, 1H), 8.24 (s, 1H).

EXAMPLE I-9

Amides of 5-(aminomethyl)-2-methylbenzimidazole were Prepared as Follows

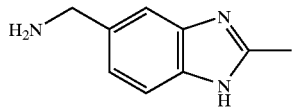

Step A: Ethyl-(2-methyl-5-benzimidazole)-carboxylate

The title compound was prepared from 2-methyl-5-benzimidazole carboxylic acid: $R_f$ (10% MeOH—CHCl$_3$)=0.31. $^1$H NMR (300 MHz, CD$_3$OD): δ(8.18, br s, 1H), 7.91 (dd, J=1.5, 8.4 Hz, 1H), 7.54 (br m, 1H), 4.38 (q, J=7.5 Hz, 2H), 2.60 (s, 3H), 1.41 (t, J=7.2 Hz, 3H).

Step B: 5-(Hydroxymethyl)-2-methylbenzimidazole

To a stirred suspension of LAH (397 mg, 10.5 mmol) in dry THF (100 mL) at 0° C. was added in portions ethyl-[2-methylbenzimidazole-5]-carboxylate (1.01 g, 4.95 mmol). After 1 h an additional 1.19 g of LAH was added and the mixture was allowed to come to room temperature. After 1 h the mixture was cooled to 0° C. and quenched by the sequential addition of H$_2$O (1.6 mL), 3N NaOH (1.6 mL) and H$_2$O (4.8 mL). The mixture was diluted with EtOAc (125 mL) and stirred at room temperature for 10–15 min until a fine gray suspension was obtained. This suspension was filtered through a small pad of Celite. The filtrate was dried (MgSO$_4$) and concentrated to afford the title compound as a white solid: $R_f$ (8:1:1 EtOAc:NH$_4$H:MeOH)=0.43. $^1$H NMR (400 MHz, CD$_3$OD): δ7.47 (s, 1H), 7.43 (d, J=8.4 Hz, 1H), 7.19 (d, J=8.4 Hz, 1H), 4.68 (s, 2H), 2.55 (s, 3H).

Step C: 5-(Aminomethyl)-2-methylbenzimidazole

The title compound was prepared from 5-(hydroxymethyl)-2-methylbenzimidazole: $R_f$ (8:1:1 EtOAc:MeOH:NH$_4$OH)=0.15. $^1$H NMR (300 MHz, CD$_3$OD): δ7.45 (m, 2H), 7.20 (d, J=8.1 Hz, 1H), 3.90 (s, 2H), 2.56 (s, 3H).

EXAMPLE I-10

Amides of 5-(Aminomethyl)-1-trityl-7-azabenzimidazole were Prepared as Follows

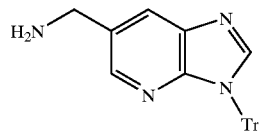

Step A: 5,6-Diaminonicotinic acid

See Markwald, W. *Chem. Ber.* 1984, 27, 1317. To a stirred solution of SnCl$_2$ (4.16 g, 22.0 mmol) in concentrated HCl (11 mL) at 0° C. was added in portions 5-nitro-6-aminonicotinic acid (1.01 g, 5.5 mmol). The resulting orange mixture was then heated to 100° C. under argon for 75 min. The mixture was then cooled to RT and was then placed in an ice bath and neutralized with concentrated aqueous ammonia (to pH 6–7), resulting in a thick cream-colored mixture. The mixture was then acidified to pH 4 with acetic acid and the precipitate collected by filtration, washed with H$_2$O and dried under vacuum overnight to afford the title compound: $^1$H NMR (300 MHz, DMSO-d6): δ7.98 (d, J=2.1 Hz, 1H), 7.21 (d, J=2.1 Hz, 1H), 6.24 (br s, 2H), 5.00 (br s, 2H).

Step B: Methyl-5,6-diaminonicotinate

A solution of 5,6-diaminonicotinic acid (5.5 mmol) in saturated methanolic HCl was heated to reflux for 3 h. The yellow solution was cooled to RT and treated with solid sodium carbonate until basic (pH 9). The mixture was filtered through Celite and the filter cake was rinsed well with methanol. The filtrate was concentrated to an oily green solid. Silica gel chromatography (16:1:1 EtOAc-MeOH—NH$_4$OH) afforded the title compound as a pale pink solid: $R_f$ (8:1:1 EtOAc-MeOH—NH$_4$OH)=0.54; $^1$H NMR (400 MHz, DMSO-d6): δ7.94 (d, J=2.0 Hz, 1H), 7.15 (d, J=2.0 Hz, 1H), 6.24 (s, 2H), 4.90 (s, 2H), 3.73 (s, 3H).

Step C: Methyl-7-azabenzimidazole-5-carboxylate

A mixture of methyl-5,6-diaminonicotinate (461 mg, 2.76 mmol), formic acid (250 μL) and triethyl orthoformate (7.5 mL) was heated to 100° C. for 2 h. The mixture was then concentrated to an oily solid. Silica gel chromatography (8:1:1 EtOAc-MeOH—NH$_4$OH) afforded the title compound as a cream-colored solid: $R_f$ (8:1:1 EtOAc-MeOH—NH$_4$OH)=0.22; $^1$H NMR (400 MHz, DMSO-d6): δ8.94 (d, J=2.0 Hz, 1H), 8.64 (s, 1H), 8.50 (d, J=2.0 Hz, 1H), 3.91 (s, 3H).

Step D: Methyl-(1-trityl-7-azabenzimidazole)-5-carboxolate

To a stirred suspension of methyl-7-azabenzimidazole-5-carboxylate (410 mg, 2.32 mmol) in CH$_2$Cl$_2$ (6.5 mL) was added Et$_3$N (646 μL, 4.63 mmol) and triphenylmethyl chloride (Aldrich, 775 mg, 2.78 mmol). The mixture was stirred at RT for 16 h and was then partitioned between CH$_2$Cl$_2$ and H$_2$O. The layers were separated and the aqueous layer was extracted once with CH$_2$Cl$_2$. The combined organic layers were washed with brine, dried (Na$_2$SO$_4$) and concentrated to an oily solid. Silica gel chromatography (gradient elution with hexanes, 25% EtOAc-hexanes, 50% EtOAc-hexanes and finally 10% MeOH—CH$_2$Cl$_2$) afforded the title compound as a white foam: $R_f$(1:1 hexanes-EtOAc)=0.12; $^1$H NMR (400 MHz, CD$_3$OD): δ8.99 (d, J=1.6 Hz, 1H), 8.40 (s, 1H), 7.47 (d, J=1.6 Hz, 1H), 7.41–7.39 (m, 9H), 7.23–7.21 (m, 6H), 3.80 (s, 3H).

Step E: 5-Aminomethyl-1-trityl-7-azabenzimidazole

The title compound was prepared from methyl-(1-trityl-7-azabenzimidazole)-5-carboxylate (530 mg, 1.26 mmol): $^1$H NMR (300 MHz, CDCl$_3$): δ8.42 (d, J=2.1 Hz, 1H), 8.12 (s, 1H), ), 7.35–7.32 (m, 9H), 7.18–7.15 (m, 6H), 6.66 (d, J=1.8 Hz, 1H), 3.71 (s, 2H).

EXAMPLE I-11

Amides of 5-(aminomethyl)-1-trityl-6-azabenzimidazole were Prepared as Follows

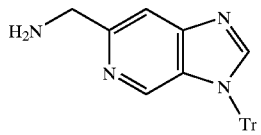

Step A: Methyl-6-azabenzimidazole-5-carboxylate

See Guzman, F. et al. *J. Med. Chem.* 1984, 27, 564. To a stirred solution of methyl-4,5,6,7-tetrahydro-6-azabenzimidazole-5-carboxylate (886 mg, 4.89 mmol) in acetic acid (15 mL) was added $SeO_2$ (2.17 g, 19.6 mmol). The reaction was stirred at 90° C. under inert atmosphere for 15 h. The mixture was then cooled and filtered through a Celite pad. The filter cake was washed with methanol. The filtrate was evaporated in vacuo to afford a solid. Silica gel chromatography eluting with 8:1:1 EtOAc:MeOH:NH$_4$OH afforded the light yellow solid: $^1$H NMR (300 MHz, CD$_3$OD): δ9.00 (d, J=0.9 Hz, 1H), 8.54 (s, 1H), 8.46 (d, J=0.9 Hz, 1H), 4.01 (s, 3H).

Step B: 5-Aminomethyl-1-trityl-6-azabenzimidazole

The title compound was prepared from methyl-6-azabenzimidazole-5-carboxylate: $^1$H NMR (400 MHz, CDCl$_3$): δ8.01 (s, 1H), 7.75 (d, J=0.8 Hz, 1H), 7.64 (s, 1H), 7.16–7.36 (m, 15H), 4.02 (s, 2), 2.00 (br s, 2H).

EXAMPLE I-12

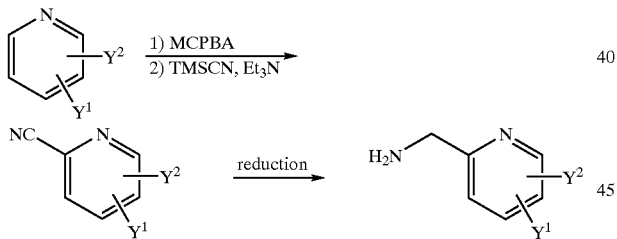

for example, when $Y^1$ is F and $Y^2$ is CH$_3$,

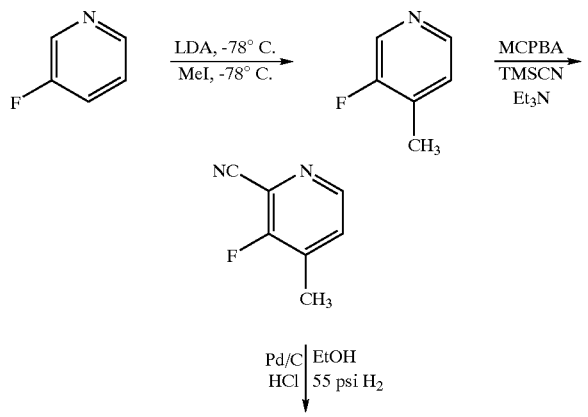

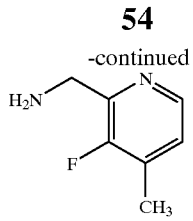

Another example, where $Y^1$ is F and $Y^2$ is H (2-aminomethyl-3-fluoropyridine), is shown below:

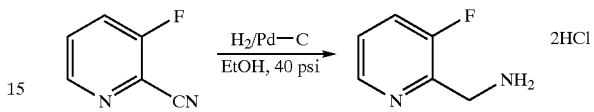

Synthesis of 2-aminomethyl-3-fluoropyridine begins with catalytic reduction of 2-cyano-3-fluoropyridine (Sakamoto et al., Chem. Pharm. Bull. 33(2) 565–571 (1985)) using palladium on carbon that provides 2-aminomethyl-3-fluoropyridine as the dihydrochloride salt.

The coupling of 2-aminomethyl-3-fluoropyridine and 3-(2,2-difluoro-2-(2-pyridyl)ethylamino)-6-methylpyrazin-2-one-1-acetic acid is carried out in DMF using EDC, HOBT and triethylamine. Addition of water precipitates the product which is then purified by silica gel chromatography to give the title compound as a slightly colored solid. Conversion to its hydrochloride salt can be carried out by treating an ethyl acetate solution with two equivalents of 1M HCl in ethyl acetate, followed by filtration.

2-Aminomethyl-3-fluoropyridine as a dihydrochloride salt

A stirred solution of 6.11 g (50.1 mmol) of 2-cyano-3-fluoropyridine in 250 mL of ethanol and 12.5 mL (150 mmol) of conc. HCl was hydrogenated over 1.90 g of 10% palladium on carbon at 40 psi for 16 h. The catalyst was removed by filtration and the solvents removed at reduced pressure. The resulting solid was diluted with acetonitrile and filtered to give 8.0 g of the title compound as an off-white solid: $^1$H NMR (CD$_3$OD) δ8.48 (d, 1H, 4.8 Hz), 7.69 (td,1H, 9.2, 1.1 Hz), 7.68 (ddd, 1H, 8.8, 4.4, 4.4 Hz), 4.34 (s, 2H).

EXAMPLE I-13

2-[1,2,3]Thiadiazole-4-yl-benzylamine

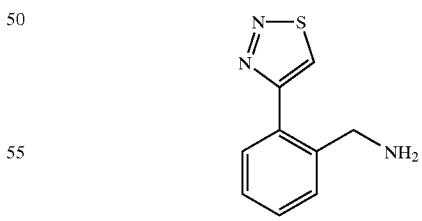

Step A: N'-(1-o-Tolyl-ethylidene)-hydrazinecarboxylic acid ethyl ester (I-13-1)

A solution of 2'-methylacetophenone (0.98 ml, 7.4 mmol), ethyl carbazate (0.81 g, 7.8 mmol) and p-toluenesulfonic acid monohydrate (70 mg, 0.37 mmol) in toluene (30 ml) was heated at reflux temperature with a Dean-Stark apparatus for 2 h. Solvent evaporation and flash chromatography (silica gel, hexane-ethyl acetate, 80:20) gave N'-(1-o-tolyl-ethylidene)-hydrazinecarboxylic acid ethyl ester; $^1$H NMR (CDCl$_3$, 400 MHz) δ7.72 (bs, 1H), 7.21 (m, 4H), 4.31 (q, 2H, J=7.1 Hz), 2.37 (s, 3H), 2.17 (s, 3H), 1.34 (t, 3H, J=7.1 Hz).

Step B: 4-o-Tolyl-[1,2,3]thiadiazole (I-13-2)

To thionyl chloride (1 ml), cooled to 0° C. was added N'-(1-o-tolyl-ethylidene)-hydrazinecarboxylic acid ethyl ester. The reaction mixture was heated to 60° C. for 1 h. Solvent evaporation gave 4-o-tolyl-[1,2,3]thiadiazole; $^1$H NMR (CDCl$_3$, 400 MHz) δ8.51 (s, 1H), 7.65 (d, 1H, J=7.3 Hz), 7.36 (m, 3H), 2.46 (s, 3H).

Step C: 4-(2-Bromomethyl-phenyl)-[1,2,3]thiadiazole (I-13-3)

A solution of 4-o-tolyl-[1,2,3]thiadiazole (100 mg, 0.57 mmol), N-bromosuccinimide (100 mg, 0.57 mmol) and 2,2'-azobisisobutyronitrile (9.4 mg, 0.057 mmol) in chloroform (10 ml) was heated at reflux temperature for ~18 h. Additional chloroform was added and the mixture was washed with water, 5% sodium thiosulfate solution and brine. Drying and solvent evaporation gave 4-(2-bromomethyl-phenyl)-[1,2,3]thiadiazole; $^1$H NMR (CDCl$_3$, 300 MHz) δ8.87 (s, 1H), 7.67–7.39 (m, 4H), 4.71 (s, 2H). cls

Step D: 4-(2-Azidomethyl-phenyl)-[1,2,3]thiadiazole (I-13-4)

A solution of 4-(2-bromomethyl-phenyl)-[1,2,3]thiadiazole (7.0 g, 0.027 mol) and sodium azide (5.3 g, 0.081 mol) in N,N-dimethylformamide (200 ml) was stirred at room temperature overnight. Ethyl acetate was added and the reaction mixture was washed with water and brine. Drying and solvent evaporation gave an oil; flash chromatography (silica gel, hexane-ethyl acetate, 96:4) gave 4-(2-azidomethyl-phenyl)-[1,2,3]thiadiazole; $^1$H NMR (CDCl$_3$, 300 MHz) δ8.74 (s, 1H), 7.76 (m, 1H), 7.53 (m, 3H), 4.54 (s, 2H).

Step E: 2-[1,2,3]Thiadiazole-4-yl-benzylamine (I-13-5)

A solution of 4-(2-azidomethyl-phenyl)-[1,2,3]thiadiazole (1.0 g, 4.6 mmol), triphenylphosphine (1.4 g, 5.5 mmol) and water (0.12 ml, 6.9 mmol) in tetrahydrofuran (20 ml) was stirred at room temperature overnight. Solvent evaporation and flash chromatography (silica gel, chloroform-2-propanol, 95:5–92:8) gave 2-[1,2,3]thiadiazole-4-yl-benzylamine; $^1$H NMR (CDCl$_3$, 300 MHz) δ8.87 (s, 1H), 7.67 (d, 1H, J=8 Hz), 7.45 (m, 3H), 3.88 (s, 2H).

EXAMPLE I-14

2-Pyrazol-1-yl-benzylamine trifluoroacetic acid salt

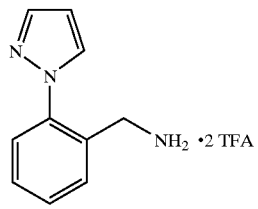

Step A: 2-Pyrazol-1-yl-benzoic acid (I-14-1)

To a vigorously stirred mixture of 2-hydrazinobenzoic acid hydrochloride (50 g, 0.27 mol) and malonaldehyde bis-dimethylacetal (43 ml, 0.27 mol) in water (630 ml) was gradually added conc. HCl (30 ml). The reaction mixture was refluxed for 2 h and methanol was evaporated. The inorganic layer was treated with charcoal until colorless, cooled, left for 2 h and filtered. The residue was washed with cold water and dried in the air to give 2-pyrazol-1-yl-benzoic acid; MS (ES+) M+1 189.4 for C$_{10}$H$_8$N$_2$O$_2$.

Step B: 2-Pyrazol-1-yl-benzamide (I-14-2)

A solution of 2-pyrazol-1-yl-benzoic acid (50 mg, 0.26 mmol), ammonium chloride (28 mg, 0.52 mmol), 1-(3-dimethylaminopropyl)-3-ethylcarbodiimide hydrochloride (100 mg, 0.52 mmol), 1-hydroxy-7-azabenzotriazole (71 mg, 0.52 mmol) and diisopropylethylamine (0.17 ml, 1.0 mmol) in N,N-dimethylformamide (0.75 ml) was stirred at room temperature for 5 h. Water was added and the reaction mixture was extracted with ethyl acetate. Drying and solvent evaporation gave 2-pyrazol-1-yl-benzamide; $^1$H NMR (CD$_3$OD, 400 MHz) δ7.92 (d, 1H, J=2.4 Hz), 7.70–7.48 (m, 5H), 6.49 (m, 1H).

Step C: 2-Pyrazol-1-yl-benzylamine trifluoroacetic acid salt (I-14-3)

A solution of 2-pyrazol-1-yl-benzamide (68 mg) and borane-tetrahydrofuran complex (1M solution in tetrahydrofuran, 1.4 ml, 1.4 mmol) in tetrahydrofuran (2 ml) was heated at reflux temperature for 2 h. Hydrochloric acid (1M solution in water, 2.8 ml) was added and the reaction mixture was heated at reflux temperature for 30 minutes. The solution was neutralized with 1N sodium hydroxide, concentrated to remove tetrahydrofuran and extracted with chloroform. Drying and solvent evaporation gave an oil; purification by reverse phase preparative HPLC (5% to 95% CH$_3$CN in water containing 0.1% TFA, C18 PRO YMC 20×150 mm) gave 2-pyrazol-1-yl-benzylamine trifluoroacetic acid salt; $^1$H NMR (CDCl$_3$, 400 MHz) δ8.80 (bs, 2H), 7.80 (m, 2H), 7.62–7.37 (m, 4H), 6.56 (t, 1H, J=2.2 Hz), 4.07 (s, 2H).

EXAMPLE I-15

2-(1H-Imidazol-2-yl)-benzylamine

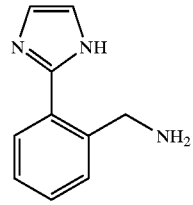

Step A: 2-Cyano-benzimidic acid ethyl ester hydrochloride (I-15-1)

A suspension of phthalonitrile (70 g, 0.55 mol) in ethanol (100 ml) and chloroform (200 ml) was warmed and then cooled to 0° C. The reaction mixture was saturated with HCl (g) and then aged at 0° C. for 2 weeks. The resultant precipitate was filtered and washed with chloroform. Dilution of the filtrate with ether produced additional 2-cyano-benzimidic acid ethyl ester hydrochloride.

Step B: 2-(1H-Imidazol-2-yl)-benzonitrile hydrochloride (I-15-2)

A solution of 2-cyano-benzimidic acid ethyl ester hydrochloride (43 g, 0.20 mol) and 2,2-diethoxy-ethylamine (30 ml, 0.21 mol) in methanol (430 ml) was aged at room temperature for 1 h. The reaction mixture was concentrated to remove methanol and conc. sulfuric acid (110 ml) was added. After heating on a steam bath for 1.5 h, the reaction mixture was diluted with water (700 ml) and extracted with chloroform. The aqueous phase was made strongly basic with sodium hydroxide and extracted with chloroform. Hydrochloric acid (12N) was added to give pH 3–4, tar was filtered and the filtrate was concentrated. The resultant brown solid was sublimed at 200–220° C. The purified solid was dissolved in hydrochloric acid solution (6N, 110 ml), byproducts filtered and the filtrate concentrated. The residue was diluted with ethanol (100–120 ml) containing hydrochloric acid (12N, 1 ml), boiled briefly and filtered. Further concentration and cooling of the filtrate gave 2-(1H-imidazol-2-yl)-benzonitrile hydrochloride (1.5 g). The filtrate was concentrated further and diluted with acetone. Filtration gave 2-(1H-imidazol-2-yl)-benzoic acid hydrochloride (7.3 g). Dilution of the filtrate with acetone and filtration of the resultant solid gave additional 2-(1H-imidazol-2-yl)-benzonitrile hydrochloride; mp 200–204° C.; IR 4.5μ.

Step C: 2-(1H-Imidazol-2-yl)-benzonitrile (I-15-3)

To a solution of 2-(1H-imidazol-2-yl)-benzonitrile hydrochloride (3 g, 0.014 mol) in water (20 ml) was added sodium hydroxide solution (2.5 N, 5 ml). Filtration of the resultant precipitate and recrystallization from ethyl acetate gave 2-(1H-imidazol-2-yl)-benzonitrile; Anal. Calcd. For $C_{10}H_7N_3$: C, 70.99; H, 4.17; N, 24.84. Found: C, 70.74; H, 4.08; N, 25.24.

Step D: 2-(1H-Imidazol-2-yl)-benzylamine (I-15-4)

A solution of 2-(1H-imidazol-2-yl)-benzonitrile (50 mg, 0.30 mmol) in ethanol saturated with ammonia (5 ml) was stirred in the presence of Raney nickel (50% slurry in water, washed with ethanol, catalytic amount) under a hydrogen atmosphere for 2 h. The reaction mixture was filtered over celite and concentrated to give 2-(1H-imidazol-2-yl)-benzylamine; $^1$H NMR (CDCl$_3$, 400 MHz) δ8.13 (d, 1H, J=7.5 Hz), 7.42 (m, 1H), 7.28 (m, 2H), 7.18 (bs, 2H), 3.96 (s, 2H).

EXAMPLE I-16

2-(1H-Pyrazol-3-yl)-benzylamine hydrochloride salt

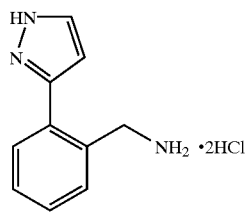

Step A: 1-(Tetrahydro-pyran-2-yl)-1H-pyrazole (I-16-1)

To pyrazole (14.3 g, 0.21 mol) was added 3,4-dihydro-2H-pyran (29 ml, 0.315 mol) and, after complete dissolving, trifluoroacetic acid (0.1 ml, 0.0013 mol) was added to the obtained solution. The reaction mixture was refluxed for 5 h, sodium hydride (0.2 g, 0.008 mol) was added, and the mixture was distilled to give 1-(tetrahydro-pyran-2-yl)-1H-pyrazole; b.p. ~60–65° C./0.5–1 torr.

Step B: 1H-Pyrazol-3-ylboronic acid (I-16-2)

To a solution of 1-(tetrahydro-pyran-2-yl)-1H-pyrazole (7.61 g, 0.0525 mol) in dry THF (50 ml), a 1.6M hexane solution of BuLi (33 ml) was added dropwise at −70° C. A white bulky precipitate formed immediately. Triisopropyl borate (12.7 ml, 0.055 mol) was added over 10 min at the same temperature (−70° C.), and kept at this temperature for 1 h. Then the mixture was decomposed with 2 eq. of 2M HCl under intensive stirring to give a white bulky precipitate. During decomposition, the temperature rose from −70° C. to 20° C. The precipitate was filtered off, washed with water and benzene (until the disappearance of a typical smell) to give 1H-pyrazol-3-ylboronic acid; $^1$H NMR (D$_2$O) δ7.47 (d, 1H), 6.20 (d, 1H).

Step C: tert-Butyl-2-bromobenzylcarbamate (I-16-3)

To a solution of 2-bromobenzylamine hydrochloride (11.12 g, 0.05 mol) in dimethylformamide (50 ml) was added di-tert-butyl dicarbonate (10.91 g, 0.05 mol) and triethylamine (3.66 ml, 0.05 mol). The reaction mixture was stirred at room temperature overnight. Saturated sodium carbonate solution was added and the mixture was extracted with ethyl acetate. The combined organic layers were washed with brine. Drying and solvent evaporation gave tert-butyl-2-bromobenzylcarbamate; MS (ES+) M+1 286.4 for $C_{12}H_{16}BrNO_2$.

Step D: tert-Butyl-2-(1H-pyrazol-3-yl) benzylcarbamate (I-16-4)

To a solution of 1H-pyrazol-3-ylboronic acid (156 mg, 1.4 mmol), tetrakis(triphenylphosphine)palladium(0) (242 mg, 0.21 mmol), and sodium carbonate (222 mg, 2.1 mmol) in dimethylformamide (2 ml), was added tert-butyl-2-bromobenzylcarbamate (200 mg, 0.699 mmol). The suspension was stirred at 100° C. for 2 h, cooled to room temperature, poured onto saturated sodium bicarbonate and extracted with ethyl acetate. The combined organic layers were washed with saturated sodium chloride, dried with magnesium sulfate and concentrated in vacuo. The crude material was passed through silica (ISCO, 0–30% ethyl acetate/hexane) to give tert-butyl 2-(1H-pyrazol-3-yl) benzylcarbamate; MS (ES+) M+1 274.1 for $C_{15}H_{19}N_3O_2$.

Step E: 2-(1H-Pyrazol-3-yl)-benzylamine hydrochloride salt (I-1 6-5)

Hydrogen chloride gas was bubbled through a 0° C. solution of tert-butyl 2-(1H-pyrazol-3-yl)benzylcarbamate (60 mg, 0.220 mmol) in ethyl acetate (5 ml) for 2 min and stirred for 40 min. A precipitate formed, and the suspension was concentrated in vacuo to give 2-(1H-pyrazol-3-yl)-benzylamine hydrochloride salt; MS (ES+) M+1 174.1 for $C_{10}H_{11}N_3$.

EXAMPLE I-17

2-Imidazol-1-yl-benzylamine

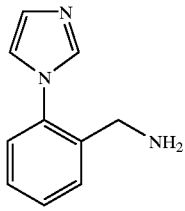

Step A: 2-Imidazol-1-yl-benzonitrile (I-17-1)

To a solution of 1H-imidazole (0.61 g, 9.0 mmol) in dimethylformamide (8 ml) was added sodium hydride (60% in oil, 0.36 g, 9.0 mmol) and the reaction mixture was stirred at room temperature for 40 min. 2-Fluoro-benzonitrile (0.9 ml, 8.2 mmol) was added and the reaction was stirred at room temperature for 45 min, heated to 60° C. for 45 min and then stirred at room temperature overnight. Ethyl acetate was added and the mixture was washed with water and brine. Drying and solvent evaporation gave 2-imidazol-1-yl-benzonitrile; $^1$H NMR (CDCl$_3$, 400 MHz) δ7.86 (bs, 1H), 7.84 (m, 1H), 7.75 (m, 1H), 7.54 (m, 1H), 7.47 (dd, 1H, J=8.1 Hz, J=1 Hz), 7.36 (m, 1H), 7.27 (m, 1H).

Step B: 2-Imidazol-1-yl-benzylamine (I-17-2)

A solution of 2-imidazol-1-yl-benzonitrile (200 mg, 1.2 mmol) in ethanol saturated with ammonia (20 ml) was stirred in the presence of Raney nickel (50% slurry in water, washed with ethanol, catalytic amount) under a hydrogen atmosphere for 4 h. The reaction mixture was filtered over celite and concentrated to give 2-Imidazol-1-yl-benzylamine; $^1$H NMR (CDCl$_3$, 400 MHz) δ7.69 (bs, 1H), 7.57 (m, 1H), 7.47 (m, 1H), 7.38 (m, 1H), 7.27 (m, 1H), 7.22 (bs, 1H), 7.16 (m, 1H) 3.73 (s, 2H).

EXAMPLE I-18

2-(1H-Tetrazol-5-yl)-benzylamine hydrochloride salt

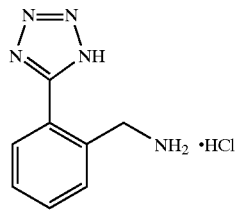

Step A: 2-Azidomethyl-benzonitrile (I-18-1)

A solution of 2-bromomethyl-benzonitrile (1.0 g, 5.1 mmol) and sodium azide (0.40 g, 6.1 mmol) in dimethylformamide (10 ml) was stirred at room temperature for 2 h. Ethyl acetate was added and the reaction mixture was washed with water and brine. Drying and solvent evaporation gave 2-azidomethyl-benzonitrile; $^1$H NMR (CDCl$_3$, 400 MHz) δ7.71 (d, 1H, J=7.7 Hz), 7.64 (m, 1H), 7.53 (d, 1H, J=7.8 Hz), 7.47 (t, 1H, J=7.6 Hz), 4.62 (s, 2H).

Step B: (2-Cyano-benzyl)-carbamic acid tert-butyl ester (I-18-2)

A solution of 2-azidomethyl-benzonitrile (0.59 g, 3.7 mmol), tin (II) chloride (1.0 g, 5.5 mmol) and di-tert-butyl dicarbonate (1.2 g, 5.5 mmol) in methanol (16 ml) and tetrahydrofuran (8 ml) was stirred at room temperature for 1 h. Concentration and flash chromatography (silica gel, hexane-ethyl acetate, 85:15) gave (2-cyano-benzyl)-carbamic acid tert-butyl ester; $^1$H NMR (CDCl$_3$, 400 MHz) δ7.64 (d, 1H, J=7.8 Hz), 7.58 (m, 1H), 7.52 (m, 1H), 7.37 (m, 1H), 5.12 (bs, 1H), 4.50 (d, 2H, J=6 Hz), 1.45 (s, 9H).

Step C: [2-(1H-Tetrazol-5-yl)-benzyl]-carbamic acid tert-butyl ester (I-18-3)

A solution of (2-cyano-benzyl)-carbamic acid tert-butyl ester (35 mg, 0.15 mmol), sodium azide (49 mg, 0.75 mmol), ammonium chloride (40 mg, 0.75 mmol) in dimethylformamide (0.5 ml) was heated to 110° C. for 8 h. After cooling to room temperature, ethyl acetate was added and the resultant solid filtered. Concentration of the filtrate gave [2-(1H-tetrazol-5-yl)-benzyl]-carbamic acid tert-butyl ester; $^1$H NMR (CD$_3$OD, 400 MHz) δ7.71(d, 1H, J=7.5 Hz), 7.58 (m, 2H), 7.48 (m, 1H), 4.44 (s, 2H), 1.42 (s, 9H).

Step D: 2-(1H-Tetrazol-5-yl)-benzylamine hydrochloride salt (I-18-4)

Through a solution of [2-(1H-tetrazol-5-yl)-benzyl]-carbamic acid tert-butyl ester (33 mg) in ethyl acetate (15 ml), cooled to 0° C. was bubbled HCl (g) for 5 min. The reaction was stirred at room temperature for 0.5 h. Nitrogen was bubbled through the reaction mixture and ether was added. Filtration gave 2-(1H-tetrazol-5-yl)-benzylamine hydrochloride salt; $^1$H NMR (CD$_3$OD, 400 MHz) δ7.86 (d, 1H, J=7.7 Hz), 7.79 (m, 1H), 7.69 (m, 1H), 7.63 (m, 1H), 4.36 (s, 2H).

EXAMPLE I-19

2-(1-Methyl-1H-tetrazol-5-yl)-benzylamine hydrochloride salt

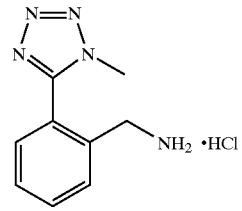

Step A: [2-(1-Methyl-1H-tetrazol-5-yl)-benzyl]-carbamic acid tert-butyl ester (I-19-1)

A solution of [2-(1H-tetrazol-5-yl)-benzyl]-carbamic acid tert-butyl ester (0.23 g, 0.84 mmol), crushed potassium carbonate (0.58 g, 4.2 mmol) and iodomethane (0.26 ml, 4.2 mmol) in dimethylformamide (4.7 ml) was stirred at room temperature for 1 h. Water was added and the reaction mixture was extracted with chloroform. Drying and solvent evaporation gave a mixture of regioisomers; separation and purification by reverse phase preparative HPLC (5% to 95% CH$_3$CN in water containing 0.1% TFA, C18 PRO YMC 20×150 mm) gave [2-(1-methyl-1H-tetrazol-5-yl)-benzyl]-carbamic acid tert-butyl ester; $^1$H NMR (CDCl$_3$, 400 MHz) δ7.66 (d, 1H, J=7.4 Hz), 7.58 (m, 1H), 7.46 (m, 1H), 7.33 (d, 1H, J=7.6 Hz), 4.17 (d, 2H, J=6.3 Hz), 4.05 (s, 3H), 1.41 (s, 9H) and [2-(2-methyl-2H-tetrazol-5-yl)-benzyl]-carbamic acid tert-butyl ester; $^1$H NMR (CDCl$_3$, 400 MHz) δ8.06 (d, 1H, J=7.4 Hz), 7.61 (d, 1H, J=7 Hz), 7.44 (m, 2H), 5.82 (bs, 1H), 4.52 (d, 2H, J=6.5 Hz), 4.44 (s, 3H), 1.43 (s, 9H ).

Step B: 2-(1-Methyl-1H-tetrazol-5-yl)-benzylamine hydrochloride salt (I-19-2)

Through a solution of [2-(1-methyl-1H-tetrazol-5-yl)-benzyl]-carbamic acid tert-butyl ester (10 mg) in ethyl acetate (5 ml), cooled to 0° C. was bubbled HCl (g) for 5 min. The reaction was stirred at room temperature for 0.5 h. Nitrogen was bubbled through the reaction mixture. Concentration from ethyl acetate gave 2-(1-methyl-1H-tetrazol-5-yl)-benzylamine hydrochloride salt; $^1$H NMR (CD$_3$OD, 400 MHz) δ7.75 (m, 4H), 4.18 (s, 3H), 4.11 (m, 2H).

EXAMPLE I-20

2-(1-Methyl-1H-tetrazol-5-yl)-benzylamine hydrochloride salt

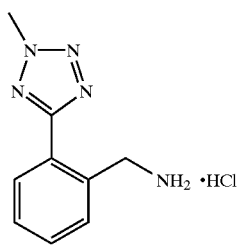

Step A: 2-(2-Methyl-2H-tetrazol-5-yl)-benzylamine hydrochloride salt (I-20-1)

Through a solution of [2-(2-methyl-2H-tetrazol-5-yl)-benzyl]-carbamic acid tert-butyl ester (15 mg) in ethyl acetate (5 ml), cooled to 0° C. was bubbled HCl (g) for 5 min. The reaction was stirred at room temperature for 0.5 h. Nitrogen was bubbled through the reaction mixture. Concentration from ethyl acetate gave 2-(2-methyl-2H-tetrazol-5-yl)-benzylamine hydrochloride salt; $^1$H NMR (CD$_3$OD, 400 MHz) δ8.24 (m, 1H), 7.63 (m, 3H) 4.48 (s, 3H), 4.47 (m, 2H).

EXAMPLE I-21

2-Tetrazol-1-yl-benzylamine

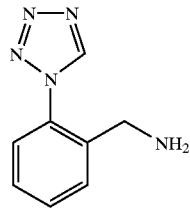

Step A. 2-Tetrazol-1-yl-benzoic acid

A suspension of 2-aminobenzoic acid (6.0 g, 0.044 mol), trimethyl orthoformate (14.2 ml, 0.13 mol) and sodium azide (8.4 g, 0.13 mol) in glacial acetic acid (150 ml) was stirred at room temperature for 2 h. Filtration and concentration from toluene gave 2-Tetrazol-1-yl-benzoic acid; $^1$H NMR (CD$_3$OD, 400 MHz) δ9.47 (s, 1H), 8.19 (dd, 1H, J=7.7 Hz, J=1.6 Hz), 7.79 (m, 2H), 7.61 (dd, 1H, J=7.7 Hz, J=1.5 Hz).

Step B. 2-Tetrazol-1-yl-benzamide

A solution of 2-Tetrazol-1-yl-benzoic acid (1.0 g, 5.2 mmol), ammonium chloride (0.56 g, 10.4 mmol), 1-(3-dimethylaminopropyl)-3-ethylcarbodiimide hydrochloride (2.0 g, 10.4 mmol), 1-hydroxy-7-azabenzotriazole (1.4 g, 10.4 mmol) and diisopropylethylamine (3.6 ml, 20.8 mmol) in N,N-dimethylformamide (15 ml) was stirred at room temperature overnight. Water was added and the reaction mixture was extracted with ethyl acetate. The combined organic layers were washed with brine. Drying and solvent evaporation gave 2-Tetrazol-1-yl-benzamide; $^1$H NMR (CD$_3$OD, 400 MHz) δ9.44 (s, 1H), 7.72 (m, 4H).

Step C. 2-Tetrazol-1-yl-benzonitrile

To a solution of 2-Tetrazol-1-yl-benzamide (1.5 g, 7.9 mmol) in tetrahydrofuran (50 ml) was added (methoxycarbonylsulfamoyl)ammonium hydroxide, inner salt (2.8 g, 11.8 mmol) in three portions over 1.5 h. Water was added and the reaction mixture was extracted with ethyl acetate. The combined organic layers were washed with brine. Drying and solvent evaporation gave 2-Tetrazol-1-yl-benzonitrile; $^1$H NMR (CDCl$_3$, 400 MHz) δ9.27 (s, 1H), 7.90 (m, 3H), 7.72 (m, 1H).

Step D. 2-Tetrazol-1-yl-benzylamine

A solution of 2-Tetrazol-1-yl-benzonitrile (1.3 g, 7.6 mmol) in ethanol saturated with ammonia (125 ml) was stirred in the presence of Raney nickel (50% slurry in water, washed with ethanol, catalytic amount) under a hydrogen atmosphere overnight. The reaction mixture was filtered over celite and concentrated to give 2-Tetrazol-1-yl-benzylamine; $^1$H NMR (CDCl$_3$, 400 MHz) δ9.28 (s, 1H), 7.59 (m, 2H), 7.47 (m, 2H), 3.70 (s, 2H).

EXAMPLE I-22

5-Chloro-2-tetrazol-1-yl-benzylamine

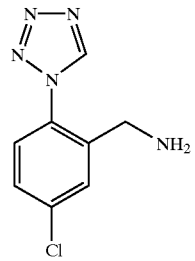

2-amino-5-chloro-benzoic acid was converted to 5-Chloro-2-tetrazol-1-yl-benzylamine $^1$H NMR (CDCl$_3$, 400 MHz) δ9.24 (s, 1H), 7.64 (d, 1H, J=2.2 Hz), 7.46 (m, 1H), 7.38 (m, 1H), 3.68 (s, 2H).

EXAMPLE I-23

C-(3-[1,2,4]Triazol-1-yl-pyridin-2-yl)-methylamine di hydrochloride

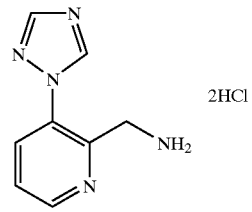

Step A. 3-[1,2,4]Triazol-1-yl-pyridine-2-carbonitrile

To a solution of 2-cyano-3-fluoro-pyridine (2.99 g, 24.49 mmol) in DMF (30 ml) is added cesium carbonate (2.03 g, 29.39 mmol) and 1,2,4-triazole (2.03 g, 29.39 mmol) and the reaction mixture is stirred at 65° C. for 4 h. After cooling to room temperature, the mixture is diluted with water and extracted with EtOAc 3 times. The aqueous layer is saturated with LiCl and further extracted with EtOAc. The combined organic layer is dried on sodium sulfate, concentrated in vacuo. The crude product is purified by flash chromatography (silica gel, 2% MeOH containing 10% NH$_4$OH in CH$_2$Cl$_2$ to 6%) to give 3-[1,2,4]Triazol-1-yl-pyridine-2-carbonitrile. $^1$H NMR (CDCl$_3$, 400 MHz) δ8.95 (s, 1H); 8.8 (d, J=4 Hz, 1H); 8.24 (s, 1H); 8.22 (d, J=8.5 Hz, 1H); 7.75 (dd, J=4, 8.5 Hz, 1H).

Step B. (3-[1,2,4]Triazol-1-yl-pyridin-2-ylmethyl)-carbamic acid tert-butyl ester To a suspension of Raney Nickel (ca. 3 pipettes of suspension in water, washed/decanted with EtOH several times) in MeOH saturated with NH$_3$ (200 ml) was added 3-[1,2,4]Triazol-1-yl-pyridine-2-carbonitrile (3.745 g, 21.88 mmol). The mixture was hydrogenated at 55 Psi for 18 h. The reaction mixture was filtered on celite under a flow of argon and the filtrate was concentrated in vacuo. To a solution of the crude material in CH$_2$Cl$_2$ (100 ml) and MeOH (10 ml) was added di-tert-butyl dicarbonate (6.2 g, 28.4 mmol) and the reaction mixture was stirred at room temperature for 30 min. The crude product obtained by concentration in vacuo is purified by flash chromatography (silica gel, 2% MeOH containing 10% NH$_4$OH in CH$_2$Cl$_2$ to 6%) to give (3-[1,2,4]Triazol-1-yl-pyridin-2-ylmethyl)-carbamic acid tert-butyl ester. $^1$H NMR (CDCl$_3$, 400 MHz) δ8.72 (d, J=4.8 Hz, 1H); 8.42 (s, 1H); 8.18 (s, 1H); 7.70 (d, J=7.6 Hz, 1H); 7.40 (dd, J=4.8, 7.6 Hz, 1H); 5.85 (bs, 1H); 4.43 (d, J=5.4 Hz, 2H); 1.45 (s, 9H).

Step C. C-(3-[1,2,4]Triazol-1-yl-pyridin-2-yl)-methylamine di hydrochloride

Through a solution of (3-[1,2,4]Triazol-1-yl-pyridin-2-ylmethyl)-carbamic acid tert-butyl ester (4.08 g) in CH$_2$Cl$_2$ (100 ml) and MeOH (20 ml) cooled to 0° C. is bubbled HCl (g) for 10 min. The flask is sealed and the reaction mixture is stirred at room temperature for 18 h. Nitrogen is bubbled through the reaction mixture for 5 min and the reaction mixture is concentrated to give C-(3-[1,2,4]Triazol-1-yl-pyridin-2-yl)-methylamine di hydrochloride as a white solid. $^1$H NMR (CD$_3$OD, 400 MHz) δ9.67 (s, 1H); 8.85 (d, J=5.3 Hz, 1H); 8.72 (s, 1H); 8.18 (d, J=8 Hz, 1 H); 7.7 (dd, J=5.3, 8 Hz, 1H); 4.45 (s, 2H).

EXAMPLE I-24

5-Chloro-2-[1,2,4]triazol-1-yl-benzylamine

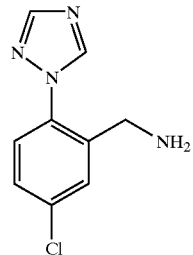

Step A. 5-Chloro-2-[1,2,4]triazol-1-yl-benzonitrile

To a solution of 2,5-dichlorobenzonitrile (10 g, 58.1 mmol) in DMF (100 ml) is added cesium carbonate (22.7 g, 69.8 mmol) and 1,2,4-triazole (4.8 g, 69.8 mmol) and the reaction mixture is stirred at 65° C. for 5.5 h, at 75° C. for 16 h, at 85° C. for 7 h. More 1,2,4-triazole (5 g) is added and the reaction mixture is stirred at 85° C. for 18 h and at 100° C. for 4 h. After cooling to room temperature, the mixture is diluted with water and extracted with EtOAc 3 times. The combined organic layer is washed with aqueous LiCl, dried on sodium sulfate, concentrated in vacuo to give 5-Chloro-2-[1,2,4]triazol-1-yl-benzonitrile as a white solid which is used in the next step without further purification.

Step B. 5-Chloro-2-[1,2,4]triazol-1-yl-benzylamine

To a suspension of 5-Chloro-2-[1,2,4]triazol-1-yl-benzonitrile (11.87 g, 58 mmol) in EtOH saturated with NH$_3$ (500 ml) was added Raney Nickel (ca. 5 pipettes of suspension in water, washed/decanted with EtOH several times). The mixture was hydrogenated at 1 atm for 26 h. The reaction mixture was filtered on celite under a flow of argon and the filtrate was concentrated in vacuo. The crude product was purified by flash chromatography (silica gel, 5% MeOH containing 10% NH$_4$OH in CH$_2$Cl$_2$ to 10%) to give 5-Chloro-2-[1,2,4]triazol-1-yl-benzylamine as a white solid. $^1$H NMR (CDCl$_3$, 400 MHz) δ8.47 (s, 1H); 8.14 (s, 1H); 7.58 (d, J=2.3 Hz, 1H); 7.38 (dd, J=2.3, 7.9 Hz, 1H); 7.30 (d, J=7.9 Hz, 1H); 3.70 (s, 2H). 8.72 (d, J=4.8 Hz, 1H); 8.42 (s, 1H); 8.18 (s, 1H); 7.70 (d, J=7.6 Hz, 1H); 7.40 (dd, J=4.8, 7.6 Hz, 1H); 5.85 (bs, 1H); 4.43 (d, J=5.4 Hz, 2H); 1.45 (s, 9H).

EXAMPLE I-25

2-(1,2,4-Triazol-1-yl)benzylamine

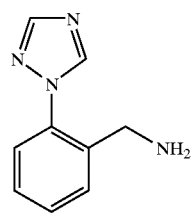

Step A. 2-(1,2,4-triazol-4-yl)cyanobenzene

To a stirred solution of 2-fluorocyanobenzene (5.0 g, 41 mmol) in DMF (75 mL) was added 1,2,4-triazole (3.0 g, 43 mmol) and cesium carbonate (14 g, 43 mmol). The mixture was warmed to 50° C. and stirred under inert atmosphere for 18 h. The mixture was cooled to ambient temperature, diluted with an equal volume of EtOAc, filtered, and the filtrate solvents were removed under reduced pressure. The residue was partitioned between ether (50 mL) and water (100 mL). The undissolved solid was collected by suction filtration and dried under reduced pressure to give 4.6 g of a 10:1 mixture of 2-(1,2,4-triazol-1-yl)cyanobenzene (hplc retention time=2.29 min, method X; TLC Rf=0.6, EtOAc) and 2-(1,2,4-triazol-4-yl)cyanobenzene (hplc retention time=1.91 min, method X; TLC Rf=0.1, EtOAc). The mixture was separated by flash chromatography using a gradient elution of 0:100 to 5:95 MeOH:EtOAc to give 2-(1,2,4-triazol-1-yl)cyanobenzene ($^1$H NMR (DMSO-d$_6$) δ9.19 (s, 1H), 8.37 (s, 1H), 8.10 (d, J=7.6 Hz, 1H), 7.96–7.87 (m, 2H), 7.71 (t, J=7.7 Hz, 1H); mass spec m/z=171 (M$^+$+H)) and 0.38 g of 2-(1,2,4-triazol-4-yl)cyanobenzene ($^1$H NMR (DMSO-d$_6$) δ9.03 (s, 2H), 8.13 (d, J=7.6 Hz, 1H), 7.93(t, J=7.8 Hz, 1H), 7.80 (d, J=7.8 Hz, 1H), 7.74 (t, J=7.7 Hz, 1H); mass spec m/z=171 (M$^+$+H)), both as white solids.

Step B. 2-(1,2,4-triazol-1-yl)-benzylamine

A solution of 2-(1,2,4-triazol-1-yl)cyanobenzene (508 mg, 2.99 mmol) and 25% by weight of palladium on carbon, 10% catalyst (134 mg) in ethanol (75 ml) was placed on a PARR Hydrogenation Apparatus under a hydrogen atmosphere at 55 psi. overnight. The mixture was filtered through celite and concentrated to give 2-(1,2,4-triazol-1-yl)-benzylamine; $^1$H NMR (CD3OD) δ8.80 (s, 1H), 8.22 (s, 1H), 7.64–7.43 (m, 4H), 3.66 (s, 2H).

EXAMPLE I-26

2-(1,2,4-Triazol-4-yl)benzylamine

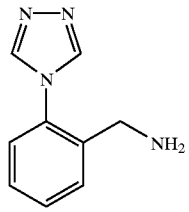

2-(1,2,4-Triazol-4-yl)cyanobenzene (0.3 g; 1.76 mmol) was combined with 30% by weight of palladium on carbon, 10% catalyst (100 mg) in ethanol (75 ml) and placed on a PARR Hydrogenation apparatus under a hydrogen atmosphere at 55 psi. for 48 hours. The mixture was filtered through celite and concentrated to give 2-(1,2,4-triazol-4-yl)benzylamine; $^1$H NMR (CD3OD) δ8.77 (s, 2H), 7.69–7.59 (m, 4H), 3.61 (s, 2H).

EXAMPLE I-27

3-(Tetrazol-1-yl)-2-aminomethylpyridine

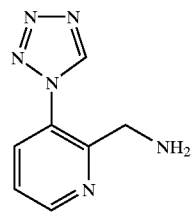

Step A. 3-(tetrazol-1-yl)cyanopyridine

To a stirred solution of tetrazole (1.0 g; 14 mmol) in DMF (150 mL) was added 40% aqueous tetrabutylammonium hydroxide (7.8 g; 12 mmol). The solvent was removed under reduced pressure. To ensure removal of all the water from the tetrabutylammonium hydroxide solution, the residue was redissolved in DMF and the solution was evaporated under reduced pressure. This procedure was repeated a total of three times. The residue was then dissolved in DMF (60 mL) and 3-fluoro-2-cyanopyridine (1.5 g; 12 mmol) was added. The reaction was stirred at ambient temperature under inert atmosphere for four days, at which time hplc analysis indicated about 65% conversion of the 3-fluoro-2-cyanopyridine to new products. The solvent was removed under reduced pressure and the residue was partitioned between EtOAc and water. The EtOAc layer was separated, dried over anhydrous MgSO$_4$, and filtered. The solvent was removed under reduced pressure and the residue was purified by flash chromatography using a gradient elution of 1:4 to 100:0 EtOAc:hexanes to give 3-(tetrazol-1-yl) cyanopyridine as a white crystalline solid (TLC Rf=0.5, 1:1 EtOAc-hexanes; hplc retention time =2.04 min, method X; $^1$H NMR (CDCl$_3$) δ9.42 (s, 1H), 8.94 (dd, J=1.3, 4.6 Hz, 1H), 8.31 (dd, J=1.3, 8.4 Hz, 1H), 7.87 (dd, J=4.6, 8.4 Hz, 1H).

Step B. 3-(tetrazol-1-yl)-2-aminomethylpyridine

A solution of 3-(tetrazol-1-yl)cyanopyridine (250 mg, 1.45 mmol) and 45% by weight of palladium on carbon, 10% catalyst (110 mg) in ethanol (75 ml) was placed on a PARR Hydrogenation Apparatus under a hydrogen atmosphere at 55 psi. overnight. The mixture was filtered through celite and concentrated to give 3-(tetrazol-1-yl)-2-aminomethylpyridine; $^1$H NMR (CD3OD) δ9.60 (s, 1H), 8.83–8.81 (m, 1H), 7.99–7.97 (m, 1H), 7.59–7.56 (m, 1H), 3.77 (s, 2H).

Exemplary procedures for preparing compounds of the invention are described below:

EXAMPLE 1

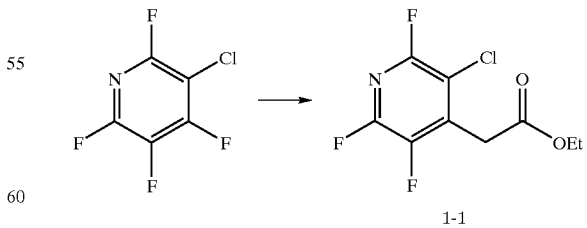

1-1

Ethyl(3-chloro-2,5,6-trifluoro-4-pyridinyl)acetate (1-1)

To a solution of 11.8 mL (58 mmol) ethyl trimethylsilylmalonate in 150 mL THF at −78° C. was added 23 mL (58 mmol, 2.5M solution in hexane)butyllithium via syringe. The reaction mixture was stirred 15 min at −78° C. then warmed to 0° C. whereupon 5.1 g (27 mmol) 3-chloro-2,4,5,6-tetrafluoropyridine was added rapidly via syringe. Stir 1 hr at 0° C. then warmed to room temperature and stirred 16 hours. The reaction mixture was diluted with 400 mL ether, mixed vigorously with 300 mL 0.05M HCl for 5 min then brought to pH 4–5 w NaOH. The layers were separated and the ether layer was washed with 300 mL brine, dried over $MgSO_4$, filtered, concentrated. Purification by automated flash chromatography (90 g silica cartridge, linear gradient 0–10% EtOAc/hex over 30 min, 70 mL/min flow rate.) afforded ethyl(3-chloro-2,5,6-trifluoro-4-pyridinyl)acetate 1-1 as a clear oil. $^1$H NMR (400 mHz, $CDCl_3$) δ4.22 (q, 2H, J=7.33 Hz); 3.93 (d, 2H, J=1.95Hz); 1.29 (t, 3H, J=7.33 Hz). Mass Spec (electrospray) M+H=254.1

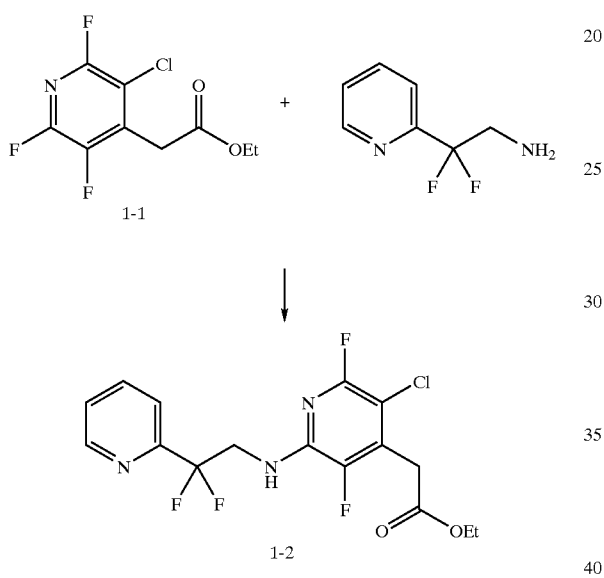

Ethyl(3-chloro-6-{[2,2-difluoro-2-(2-pyridinyl)ethyl]amino}-2,5-difluoro-4-pyridinyl)acetate (1-2)

To a solution of 5.5 g (22 mmol) ethyl(3-chloro-2,5,6-trifluoro-4-pyridinyl)acetate 1-1 in 75 mL DMF was added 3 g (19 mmol) 2,2-difluoro-2-(2-pyridinyl)ethylamine and 4 g (40 mmol) $CaCO_3$ and the reaction mixture was heated to 70° C. for 18 hours. The reaction mixture was then cooled, diluted w. 400 mL ether, washed 2×300 mL water, and 1×300 mL brine, dried over $MgSO_4$, filtered, and concentrated. Purification by automated flash chromatography (90 g silica cartridge, linear gradient 5–50% EtOAc/hex over 30 min, 70 mL/min flow rate.) afforded ethyl (3-chloro-6-{[2,2-difluoro-2-(2-pyridinyl)ethyl]amino}-2,5-difluoro-4-pyridinyl)acetate 1-2 as a white solid. $^1$H NMR (400 mHz, $CDCl_3$) δ8.66 (br d, 1H, J=4.94 Hz); 7.84 (ddd, 1H, J=7.7, 7.7, and 1.64 Hz); 7.70 (d, 1H, J=7.88 Hz); 7.41 (dd, 1H, J=4.95, 7.14 Hz); 5.40 (br m, 1H); 4.36 (dt, 2H, J=13.9, 6.22 Hz); 4.19 (q, 2H, J=7.14 Hz); 3.77 (d, 2H, J=1.83 Hz); 1.27 (t, 3H, J=7.14 Hz). Mass Spectrum (electrospray) M+H= 392.0.

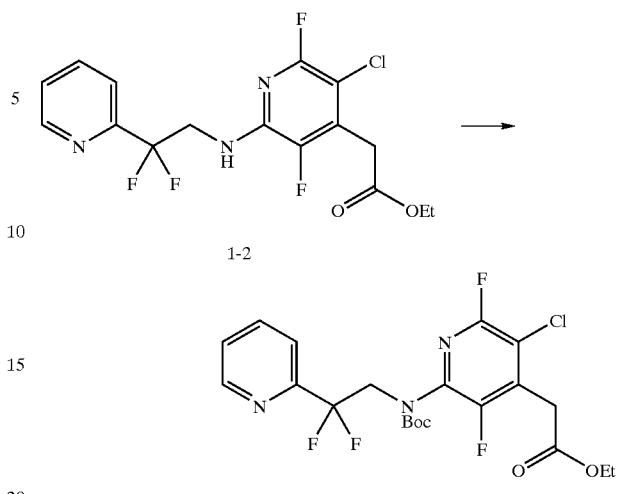

Ethyl(2-{(tert-butoxycarbonyl)[2,2-difluoro-2-(2-pyridinyl)ethyl]amino}-5-chloro-3,6-difluoro-4-pyridinyl)acetate (1-3)

To a solution of 1.63 g (4.16 mmol) ethyl(3-chloro-6-{[2,2-difluoro-2-(2-pyridinyl)ethyl]amino}-2,5-difluoro-4-pyridinyl)acetate 1-2 in 50 mL $CH_2Cl_2$ was added 1.09 g di-tert-butyldicarbonate and 0.56 g 4-N,N-dimethylaminopyridine and the reaction mixture stirred at room temperature 60 hours. The reaction mixture was diluted with 200 mL ether, washed with 200 mL each of 0.03M HCl, saturated sodium bicarbonate solution, and brine, then dried over $MgSO_4$, filtered, and concentrated. Purification by automated flash chromatography (90 g silica cartridge, linear gradient 5–40% EtOAc/hex over 25 min, 70 mL/min flow rate.) afforded ethyl(2-{(tert-butoxycarbonyl)[2,2-difluoro-2-(2-pyridinyl)ethyl]amino}-5-chloro-3,6-difluoro-4-pyridinyl)acetate 1-3 as a thick oil. $^1$H NMR (400 mHz, $CDCl_3$) δ8.59 (br d, 1H, J=4.76 Hz); 7.77 (ddd, 1H, J=7.7, 7.7, and 1.65 Hz); 7.60 (d, 1H, J=7.88 Hz); 7.34 (dd, 1H, J=4.76, 6.96 Hz); 4.67 (t, 2H, J=13.7 Hz); 4.19 (q, 2H, J=7.14 Hz); 3.85 (d, 2H, J=1.64 Hz); 1.38 (s, 9H); 1.27 (t, 3H, J=7.14 Hz).

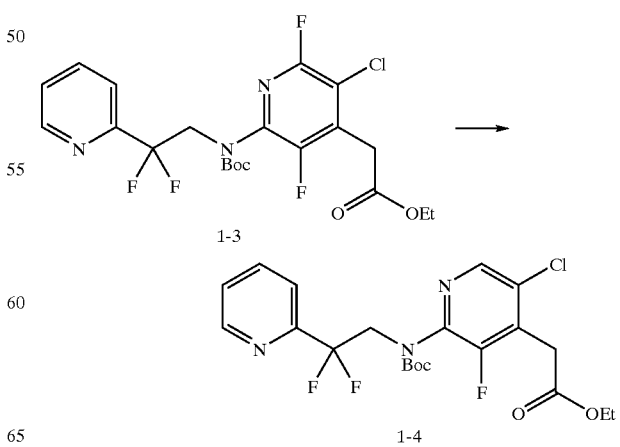

Ethyl(2-{(tert-butoxycarbonyl)[2,2-difluoro-2-(2-pyridinyl)ethyl]amino}-5-chloro-3-fluoro-4-pyridinyl)acetate (1-4)

To a solution of 1.9 g (3.86 mmol) ethyl(2-{(tert-butoxycarbonyl)[2,2-difluoro-2-(2-pyridinyl)ethyl]amino}-5-chloro-3,6-difluoro-4-pyridinyl)acetate 1-3 in 20 mL THF was added 0.3 g (4.25 mmol) NaSMe as a slurry in 20 mL DMF. The reaction mixture was stirred 30 min at room temperature, then another 15 mg portion of NaSMe in 1 mL DMF was added, and after stirring 15 min the reaction mixture was poured into 250 mL ether/200 mL H2O/4.5 mL 1N HCl. The layers were mixed and separated. The ether layer was washed with 200 mL dilute saturated sodium bicarbonate solution, brine, dried over $MgSO_4$, filtered, concentrated. to give 2.2 g of a viscous oil that was dissolved in 15 mL ethanol. To this was added 10 mL of a thick EtOH slurry of raney nickel. After 15 min, another 10 mL portion was added, and after 30 more min another 1 mL portion was added. The mixture was then filtered through celite, rinsed with 300 mL MeOH, and concentrated. Purification by automated flash chromatography (90 g silica cartridge, linear gradient 5–40% EtOAc/hex over 25 min, 70 mL/min flow rate.) afforded ethyl(2-{(tert-butoxycarbonyl)[2,2-difluoro-2-(2-pyridinyl)ethyl]amino}-5-chloro-3-fluoro-4-pyridinyl)acetate 1-4. $^1$H NMR (400 mHz, $CDCl_3$) δ8.58 (br d, 1H, J=4.76 Hz); 8.22 (s, 1H); 7.76 (br dd, 1H, J=7.7 and 7.7 Hz); 7.63 (d, 1H, J=7.88 Hz); 7.32 (dd, 1H, J=4.76 and 7.51 Hz); 4.73 (t, 2H, J=13.6 Hz); 4.19 (q, 2H, J=7.14 Hz); 3.81 (s, 2H); 1.36 (s, 9H); 1.26 (t, 3H, J=7.14 Hz). Mass spectrum (electrospray) M+H=474.1

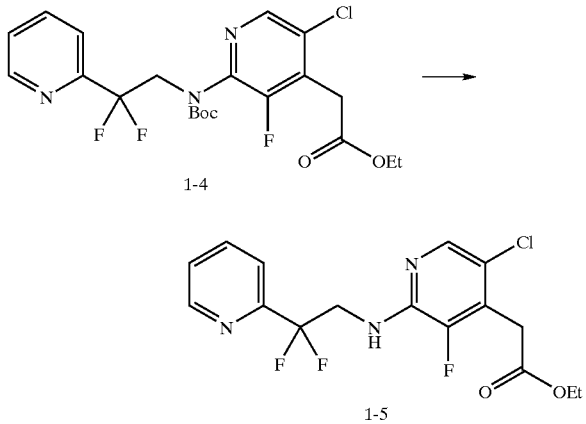

Ethyl(5-chloro-2-{[2,2-difluoro-2-(2-pyridinyl)ethyl]amino}-3-fluoro-4-pyridinyl)acetate (1-5)

Through a 0° C. solution of 0.6 g (1.6 mmol) ethyl(2-{(tert-butoxycarbonyl)[2,2-difluoro-2-(2-pyridinyl)ethyl]amino}-5-chloro-3-fluoro4-pyridinyl)acetate 1-4 in 12 mL EtOAc was passed a steady stream of HCl gas for 20 min, then the reaction mixture was allowed to stir at 0° C. for 20 min. A precipitate formed so 1 mL MeOH was added to make the reaction homogeneous and HCl gas was passed through the mixture for another 15 min., then a stream of $N_2$ gas for 5 min, then the mixture poured into 300 mL EtOAc/100 mL 2M NaOH/15 mL conc NaOH and the layers mixed and separated. The aqueous, layer was back extracted with 50 mL EtOAc and the combined organic layers washed with 150 mL water, and brine, then dried over $Na_2SO_4$, filtered, concentrated, to give ethyl(5-chloro-2-{[2,2-difluoro-2-(2-pyridinyl)ethyl]amino}-3-fluoro-4-pyridinyl) acetate 1-5 which was used without further purification. $^1$H NMR (400 mHz, $CDCl_3$) δ8.66 (br d, 1H, J=4.76 Hz); 7.88 (s, 1H); 7.82 (ddd, 1H, J=7.7, 7.7, and 1.64 Hz); 7.69 (d, 1H, J=7.87 Hz); 7.39 (dd, 1H, J=4.76 and 7.33 Hz); 5.21 (br m, 1H); 4.43 (dt, 2H, J=13.9 and 6.05 Hz); 4.18 (q, 2H, J=7.14 Hz); 3.75 (d, 2H, J=1.65 Hz); 1.26 (t, 3H, J=7.14 Hz). Mass spectrum (electrospray) M+H=374.1

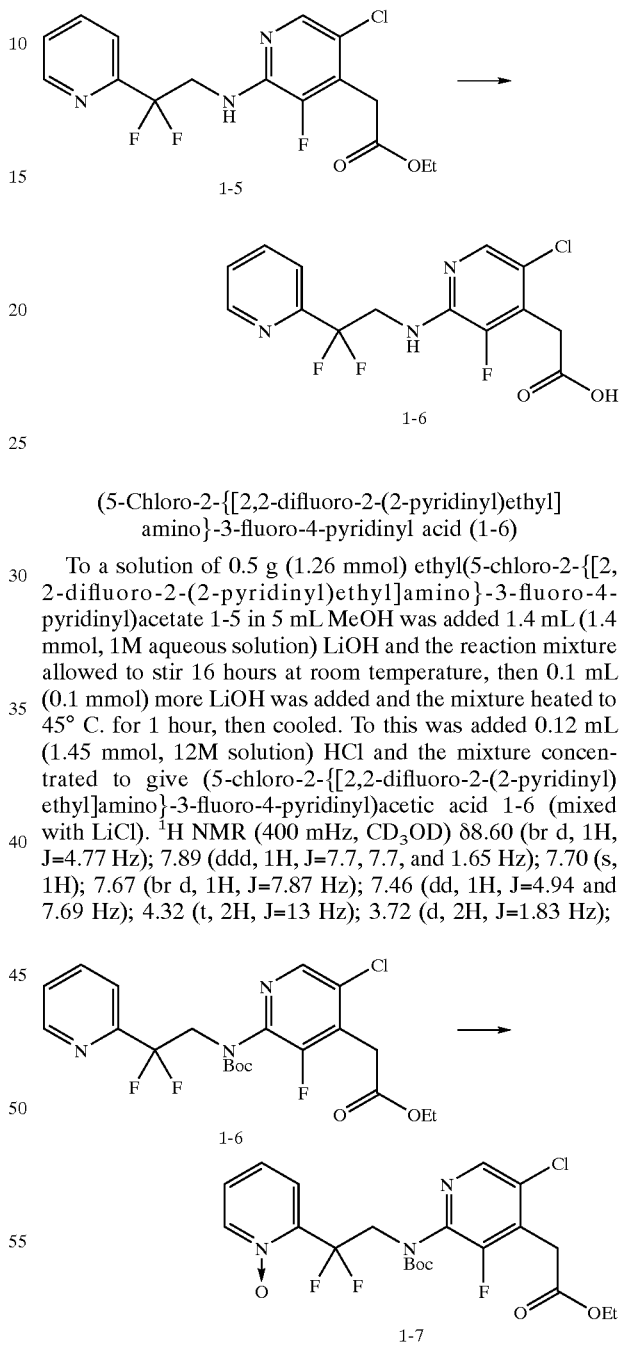

(5-Chloro-2-{[2,2-difluoro-2-(2-pyridinyl)ethyl]amino}-3-fluoro-4-pyridinyl acid (1-6)

To a solution of 0.5 g (1.26 mmol) ethyl(5-chloro-2-{[2,2-difluoro-2-(2-pyridinyl)ethyl]amino}-3-fluoro-4-pyridinyl)acetate 1-5 in 5 mL MeOH was added 1.4 mL (1.4 mmol, 1M aqueous solution) LiOH and the reaction mixture allowed to stir 16 hours at room temperature, then 0.1 mL (0.1 mmol) more LiOH was added and the mixture heated to 45° C. for 1 hour, then cooled. To this was added 0.12 mL (1.45 mmol, 12M solution) HCl and the mixture concentrated to give (5-chloro-2-{[2,2-difluoro-2-(2-pyridinyl)ethyl]amino}-3-fluoro-4-pyridinyl)acetic acid 1-6 (mixed with LiCl). $^1$H NMR (400 mHz, $CD_3OD$) δ8.60 (br d, 1H, J=4.77 Hz); 7.89 (ddd, 1H, J=7.7, 7.7, and 1.65 Hz); 7.70 (s, 1H); 7.67 (br d, 1H, J=7.87 Hz); 7.46 (dd, 1H, J=4.94 and 7.69 Hz); 4.32 (t, 2H, J=13 Hz); 3.72 (d, 2H, J=1.83 Hz);

Ethyl(2-{(tert-butoxycarbonyl)[2,2-difluoro-2-(1-oxido-2-pyridinyl)ethyl]amino}-5-chloro-3-fluoro-4-pyridinyl)acetate (1-7)

To a solution of 0.8 g (1.7 mmol) ethyl(2-{(tert-butoxycarbonyl)[2,2-difluoro-2-(2-pyridinyl)ethyl]amino}-5-chloro-3-fluoro-4-pyridinyl)acetate 1-6 in 3 mL 1,2- dichloroethane was added 0.44 g (1.8 mmol, 70% by weight) m-chloroperoxybenzoic acid. The reaction mixture was stirred at room temperature 16 h, heated to 60° C. 2 h, cooled, diluted with 300 mL EtOAc, washed with 200 mL 0.1M NaOH, and 200 mL brine. Dried over $Na_2SO_4$, filtered, and concentrated. Purification by automated flash chromatography (40 g silica cartridge, linear gradient 1–10% $MeOH/CH_2Cl_2$ over 25 min, 40 mL/min flow rate) followed by repurification of the mixed fractions by traditional silica gel chromatography (2×15 cm silica gel, linear gradient 2–5% $MeOH/CH_2Cl_2$) afforded ethyl(2-{(tert-butoxycarbonyl)[2,2-difluoro-2-(1-oxido-2-pyridinyl)ethyl]amino}-5-chloro-3-fluoro-4-pyridinyl)acetate 1-7. $^1H$ NMR (400 mHz, $CDCl_3$) δ8.20 (s, 1H); 8.18 (br d, 1H, J=5 Hz); 7.57 (br dd, 1H, J=7.7 and 2 Hz); 7.31 (br m, 2H); 5.0 (br m, 2H); 4.19 (q, 2H, J=7.14 Hz); 3.82 (s, 2H); 1.28 (s, 9H); 1.25 (t, 3H, J=7.14 Hz). Mass spectrum (electrospray) M+H=490.1

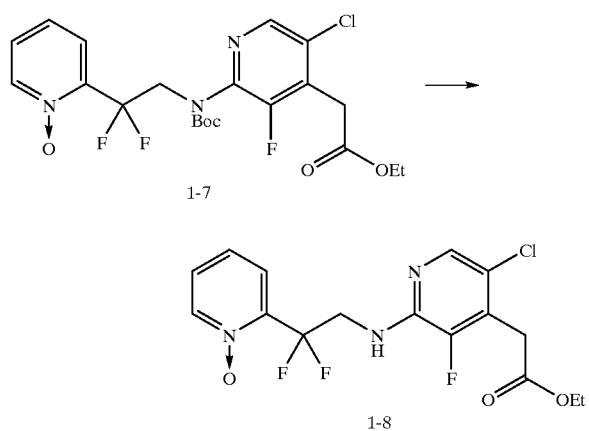

Ethyl(5-chloro-2-{[2,2-difluoro-2-(1-oxido-2-pyridinyl)ethyl]amino}-3-fluoro-4-pyridinyl)acetate (1-8)

To a 0° C. solution of 0.6 g (1.25 mmol) ethyl(2-{(tert-butoxycarbonyl)[2,2-difluoro-2-(1-oxido-2-pyridinyl)ethyl]amino}-5-chloro-3-fluoro-4-pyridinyl)acetate 1-7 in 20 mL EtOAc was passed a steady stream of HCl gas for 10 min, then the reaction mixture was allowed to stir at 0° C. for 1 hr. A stream of $N_2$ gas was then passed through the mixture for 5 min, and the mixture poured into 200 mL EtOAc/50 mL 2M NaOH/7 mL conc NaOH and the layers mixed and separated. The aqueous, layer was back extracted with 50 mL EtOAc and the combined organic layers washed with 150 mL water, and brine, then dried over $Na_2SO_4$, filtered, concentrated, to give ethyl(5-chloro-2-{[2,2-difluoro-2-(1-oxido-2-pyridinyl)ethyl]amino}-3-fluoro-4-pyridinyl)acetate 1-8 which was used without further purification. $^1H$ NMR (400 mHz, $CDCl_3$) δ8.28 (br d, 1H, J=6.41 Hz); 7.81 (s, 1H); 7.62 (dd, 1H, J=8.06 and 2.20 Hz); 7.33 (m, 2H); 5.21 (br m, 1H); 4.68 (dt, 2H, J=13.9 and 6.59 Hz); 4.18 (q, 2H, J=6.96 Hz); 3.72 (d, 2H, J=1.47 Hz); 1.26 (t, 3H, J=7.14 Hz). Mass spectrum (electrospray) M+H=390.1

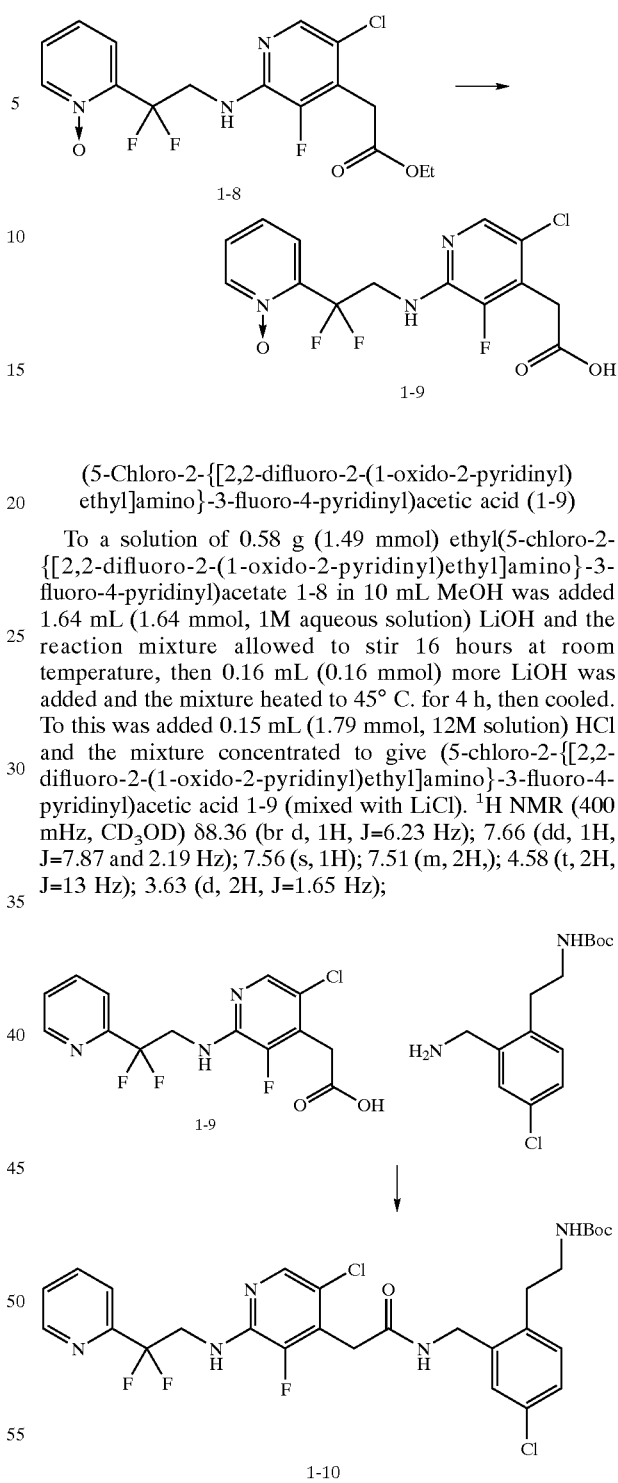

(5-Chloro-2-{[2,2-difluoro-2-(1-oxido-2-pyridinyl)ethyl]amino}-3-fluoro-4-pyridinyl)acetic acid (1-9)

To a solution of 0.58 g (1.49 mmol) ethyl(5-chloro-2-{[2,2-difluoro-2-(1-oxido-2-pyridinyl)ethyl]amino}-3-fluoro-4-pyridinyl)acetate 1-8 in 10 mL MeOH was added 1.64 mL (1.64 mmol, 1M aqueous solution) LiOH and the reaction mixture allowed to stir 16 hours at room temperature, then 0.16 mL (0.16 mmol) more LiOH was added and the mixture heated to 45° C. for 4 h, then cooled. To this was added 0.15 mL (1.79 mmol, 12M solution) HCl and the mixture concentrated to give (5-chloro-2-{[2,2-difluoro-2-(1-oxido-2-pyridinyl)ethyl]amino}-3-fluoro-4-pyridinyl)acetic acid 1-9 (mixed with LiCl). $^1H$ NMR (400 mHz, $CD_3OD$) δ8.36 (br d, 1H, J=6.23 Hz); 7.66 (dd, 1H, J=7.87 and 2.19 Hz); 7.56 (s, 1H); 7.51 (m, 2H,); 4.58 (t, 2H, J=13 Hz); 3.63 (d, 2H, J=1.65 Hz);

tert-Butyl 2-[4-chloro-2-({[(5-chloro-2-{[2,2-difluoro-2-(2-pyridinyl)ethyl]amino}-3-fluoro-4-pyridinyl)acetyl]amino}methyl)phenyl]ethylcarbamate (1-10)

To a solution of 0.035 g (0.1 mmol) (5-chloro-2-{[2,2-difluoro-2-(2-pyridinyl)ethyl]amino}-3-fluoro-4-pyridinyl)acetic acid 1-9 (mixed with LiCl) in 1 mL DMF was added 0.029 g (0.1 mmol) tert-butyl 2-[2-(aminomethyl)-4- chlorophenyl]ethylcarbamate, 0.03 g (0.15 mmol) EDC and 0.014 g (0.1 mmol) HOAt and the reaction mixture stirred at room temperature 4 h, then diluted with 50 mL EtOAc, washed with 50 mL saturated aqueous sodium bicarbonate solution, brine, then dried over $Na_2SO_4$, filtered, and concentrated. Purification by flash chromatography (2×12 cm silica gel, linear gradient 2–6% MeOH (containing 10% saturated ammonium hydroxide solution)/$CH_2Cl_2$ afforded tert-butyl 2-[4-chloro-2-({[(5-chloro-2-{[2,2-difluoro-2-(2-pyridinyl)ethyl]amino}-3-fluoro-4-pyridinyl)acetyl]amino}methyl)phenyl]ethylcarbamate 1-10. $^1$H NMR (400 mHz, $CD_3OD$) δ8.60 (d, 1H, J=4.58 Hz); 7.89 (ddd, J=7.7, 7.7, and 1.47 Hz); 7.72 (s, 1H); 7.67 (d, 1H, J=7.87 Hz); 7.46 (dd, 1H, J=7.51 and 4.58); 7.29(d, 1H, J=1.83 Hz); 7.18 (m, 2H); 4.42 (s, 2H); 4.32 (t, 2H, J=13.9 Hz); 3.74 (d, 2H, J=1.46 Hz); 3.21 (t, 2H, J=7.14 Hz); 2.80 (t, 2H, J=7.4 Hz); 1.40 (s, 9H). Mass Spectrum (electrospray) M+H=612.3.

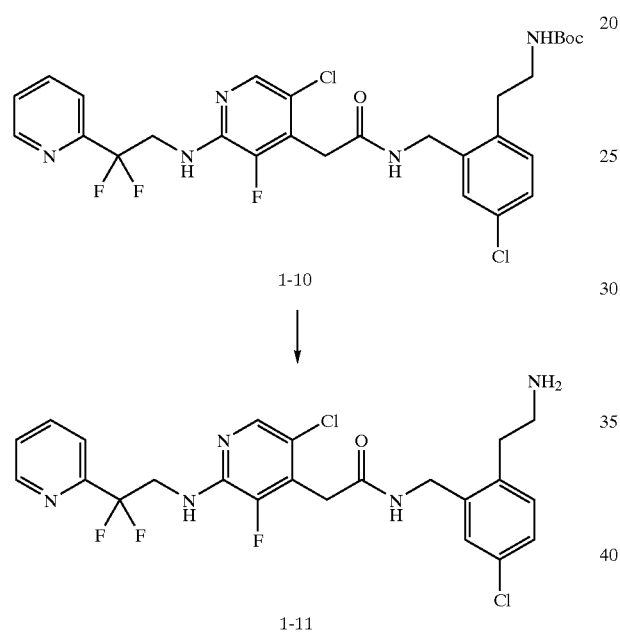

1-10

↓

1-11

N-[2-(2-aminoethyl)-5-chlorobenzyl]-2-(5-chloro-2-{[2,2-difluoro-2-(2-pyridinyl)ethyl]amino}-3-fluoro-4-pyridinyl)acetamide (1-11)

To a 0° C. solution of 0.04 g (0.065 mmol) tert-butyl 2-[4-chloro-2-({[(5-chloro-2-{[2,2-difluoro-2-(2-pyridinyl)ethyl]amino}-3-fluoro-4-pyridinyl)acetyl]amino}methyl)phenyl]ethylcarbamate 1-10 in 2 mL EtOAc/1 mL MeOH was passed through a steady stream of HCl gas for 5 minutes, then the reaction mixture was concentrated to give N-[2-(2-aminoethyl)-5-chlorobenzyl]-2-(5-chloro-2-{[2,2-difluoro-2-(2-pyridinyl)ethyl]amino}-3-fluoro-4-pyridinyl)acetamide 1-11. $^1$H NMR (400 mHz, $CD_3OD$) δ8.71 (d, 1H, J=4.58 Hz); 8.15 (apparent t, 1H, J=7.51 Hz); 7.89 (d, J=8.06 Hz); 7.70 (m, 2H); 7.29(d, 1H, J=1.84 Hz); 7.28 (dd, 1H, J=2.01 and 8.24 Hz); 7.23 (d, 1H, J=8,24 Hz); 4.42 (s, 2H); 4.36 (t, 2H, J=13.5 Hz); 3.80 (s, 2H); 3.41 (m, 2H); 3.02 (m, 2H). Mass Spectrum (electrospray) M+H=512.2

The following compounds were prepared by similar procedures to those listed above.

EXAMPLE 2

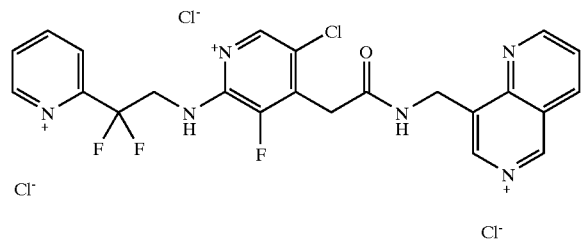

2-1

8-({[(5-Chloro-2-{[2,2-difluoro-2-(2-pyridiniumyl)ethyl]amino}-3-fluoro-4 -pyridiniumyl)acetyl]amino}methyl)[1,6]naphthyridin-6-ium trichloride
2-1

(ES) exact mass calcd for $C_{23}H_{18}ClF_3N_6O$: 487.1255, Found: 487.1234

EXAMPLE 3

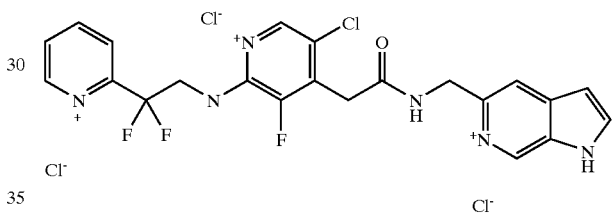

3-1

5-({[(5-Chloro-2-{[2,2-difluoro-2-(2-pyridiniumyl)ethyl]amino}-3-fluoro-4 -pyridiniumyl)acetyl]amino}methyl)-1H-pyrrolo[2,3-c]pyridin-6-ium trichloride 3-1

(ES) exact mass calcd for $C_{22}H_{18}ClF_3N_6O$: 475.1255, Found: 475.1229

EXAMPLE 4

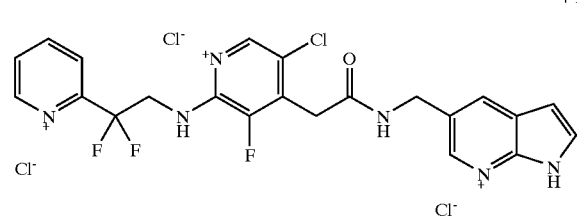

4-1

5-({[(5-Chloro-2-{[2,2-difluoro-2-(2-pyridiniumyl)ethyl]amino}-3-fluoro4-pyridiniumyl)acetyl]amino}methyl)-1H-pyrrolo[2,3-β]pyridin-7-ium trichloride 4-1

(ES) exact mass calcd for $C_{22}H_{18}ClF_3N_6O$: 475.1255, Found: 475.1226

EXAMPLE 5

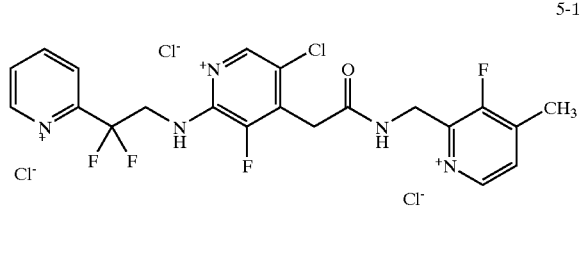

5-Chloro-2-{[2,2-difluoro-2-(2-pyridiniumyl)ethyl]amino}-3-fluoro-4-(2-{[(3-fluoro-4-methyl-2-pyridiniumyl)methyl]amino}-2-oxoethyl)pyridinium trichloride 5-1

(ES) M+H=468.1

EXAMPLE 6

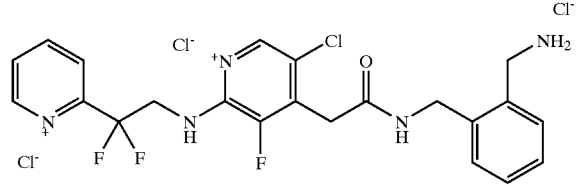

4-(2-{[2-(Ammoniomethyl)benzyl]amino}-2-oxoethyl)-5-chloro-2-{[2,2-difluoro-2-(2-pyridiniumyl)ethyl]amino}-3-fluoropyridinium trichloride 6-1

(ES) exact mass calcd for $C_{22}H_{21}ClF_3N_5O$: 464.1459, Found: 464.1466

EXAMPLE 7

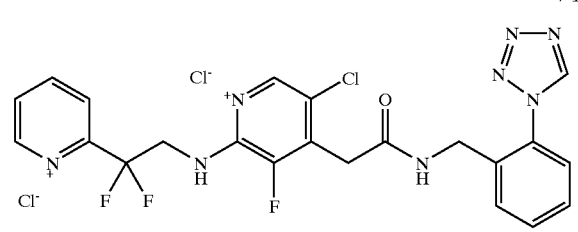

5-Chloro-2-{[2,2-difluoro-2-(2-pyridiniumyl)ethyl]amino}-3-fluoro-4-(2-oxo-2-{[2-(1H-tetraazol-1-yl)benzyl]amino}ethyl)pyridinium dichloride 7-1

(ES) exact mass calcd for $C_{22}H_{18}ClF_3N_8O$: 503.1317, Found: 503.1315

EXAMPLE 8

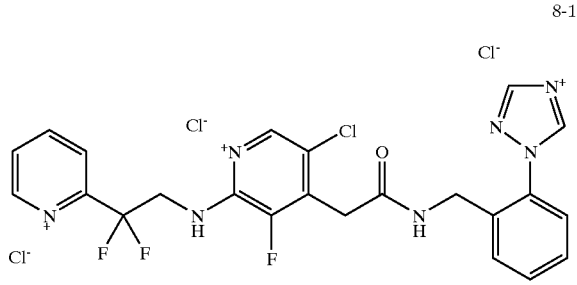

5-Chloro-2-{[2,2-difluoro-2-(2-pyridiniumyl)ethyl]amino}-3-fluoro-4-(2-oxo-2-{[2-(1H-1,2,4-triazol-4-ium-1-yl)benzyl]amino}ethyl)pyridinium trichloride 8-1

(ES) exact mass calcd for $C_{23}H_{19}ClF_3N_7O$: 502.1364, Found: 502.1367

EXAMPLE 9

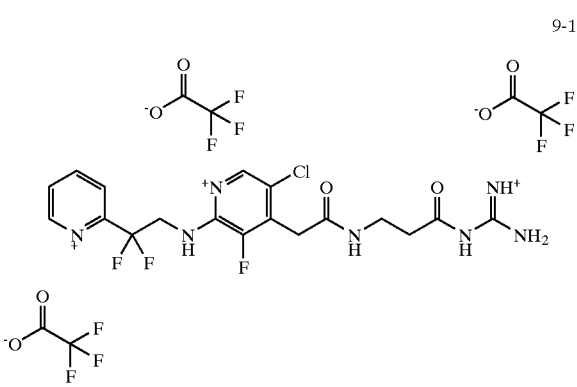

4-{2-[(3-{[Amino(iminio)methyl]amino}-3-oxopropyl)amino]-2-oxoethyl}-5-chloro-2-{[2,2-difluoro-2-(2-pyridiniumyl)ethyl]amino}-3-fluoropyridinium tris(trifluoroacetate) 9-1

(ES) M+H=458.1

EXAMPLE 10

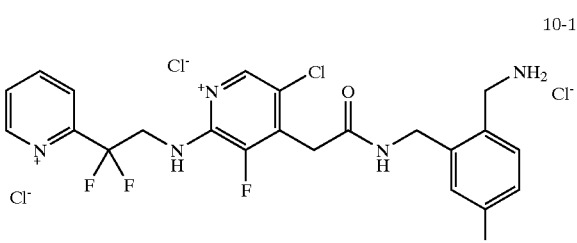

N-[2-(2-aminomethyl)-5-chlorobenzyl]-2-(5-chloro-2-{[2,2-difluoro-2-(2-pyridinyl)ethyl]amino}-3-fluoro-4-pyridinyl)acetamide 10-1

Mass Spectrum (electrospray) M+H=498.1

EXAMPLE 11

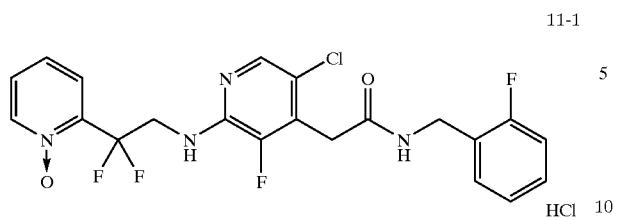

11-1

2-(5-Chloro-2-{[2,2-difluoro-2-(1-oxido-2-pyridinyl)ethyl]amino}-3-fluoro-4-pyridinyl)-N-(2-fluorobenzyl)acetamide 11-1

$C_{21}H_{17}ClF_4N_4O_2$, Mol. Wt.=468.842 (MS: M+H=469.1)

EXAMPLE 12

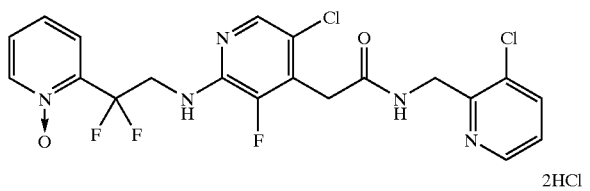

12-1

2-(5-Chloro-2-{[2,2-difluoro-2-(1-oxido-2-pyridinyl)ethyl]amino}-3-fluoro-4-pyridinyl)-N-[(3-chloro-2-pyridinyl)methyl]acetamide 12-1

$C_{20}H_{16}Cl_2F_3N_5O_2$, Mol. Wt.=486.284 (MS: M+H=486.0)

EXAMPLE 13

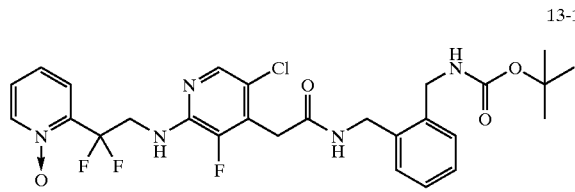

13-1 tert-Butyl-2-({[[(5-chloro-2-{[2,2-difluoro-2-(1-oxido-2-pyridinyl)ethyl]amino}-3-fluoro-4-pyridinyl)acetyl]amino}methyl)benzylcarbamate 13-1

$C_{27}H_{29}ClF_3N_5O_4$, Mol. Wt.=580.011 (MS: M+H=580.3)

EXAMPLE 14

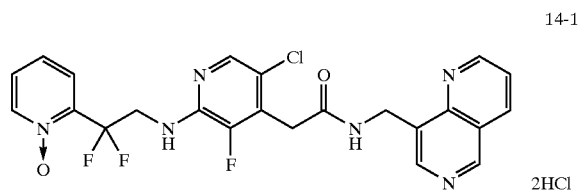

14-1

2-(5-Chloro-2-{[2,2-difluoro-2-(1-oxido-2-pyridinyl)ethyl]amino}-3-fluoro-4-pyridinyl)-N-([1,6]naphthyridin-8-ylmethyl)acetamide 14-1

$C_{23}H_{18}ClF_3N_6O_2$, Mol. Wt.=502.887 (MS: M+H=503.1)

EXAMPLE 15

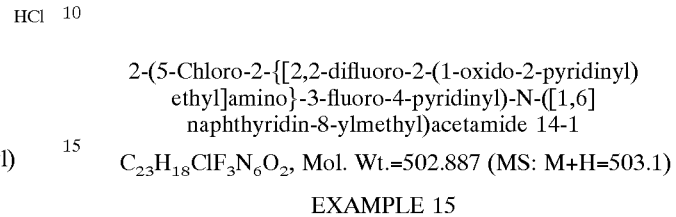

15-1

2-(5-Chloro-2-{[2,2-difluoro-2-(1-oxido-2-pyridinyl)ethyl]amino}-3-fluoro-4-pyridinyl)-N-[2-(1H-1,2,4-triazol-1-yl)benzyl]acetamide 15-1

$C_{23}H_{19}ClF_3N_7O_2$, Mol. Wt.=517.902 (MS: M+H=518.2)

EXAMPLE 16

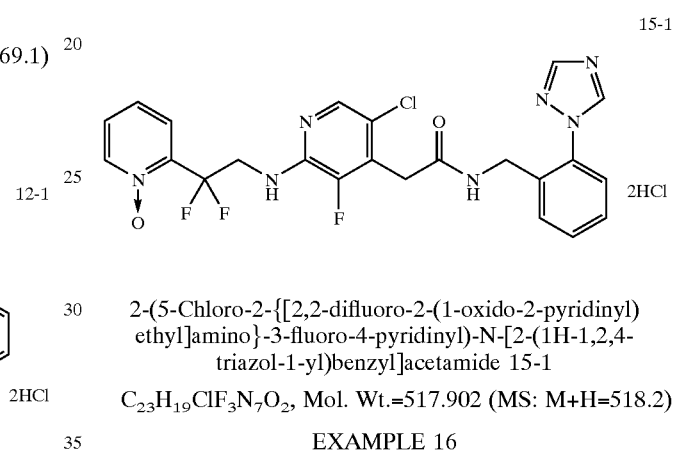

16-1

2-(5-Chloro-2-{[2,2-difluoro-2-(1-oxido-2-pyridinyl)ethyl]amino}-3-fluoro-4-pyridinyl)-N-[2-(3-chlorophenyl)ethyl]acetamide 16-1

$C_{22}H_{19}Cl_2F_3N_4O_2$, Mol. Wt.=499.324 (MS: M+H=499.1)

EXAMPLE 17

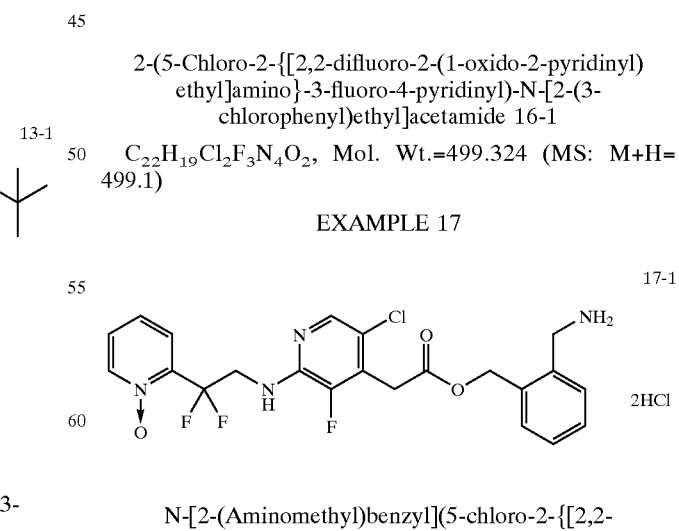

17-1

N-[2-(Aminomethyl)benzyl](5-chloro-2-{[2,2-difluoro-2-(1-oxido-2-pyridinyl)ethyl]amino}-3-fluoro-4-pyridinyl)acetate 17-1

$C_{22}H_{21}ClF_3N_5O_2$, Mol. Wt.=479.893 (MS: M+H=480.1)

EXAMPLE 18

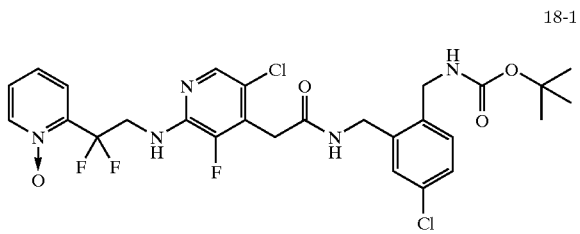

18-1 tert-Butyl 4-chloro-2-({[(5-chloro-2-{[2,2-difluoro-2-(1-oxido-2-pyridinyl)ethyl]amino}-3-fluoro-4-pyridinyl)acetyl]amino}methyl)benzylcarbamate 18-1

$C_{27}H_{28}Cl_2F_3N_5O_4$, Mol. Wt.=614.457 (MS: M+H= 614.2)

EXAMPLE 19

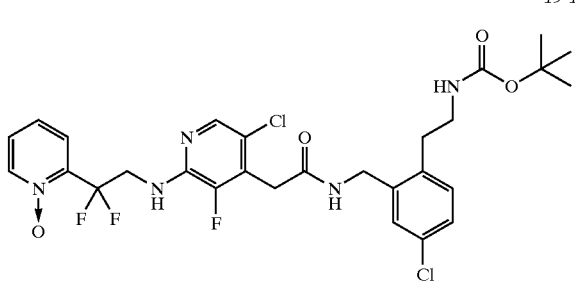

19-1 tert-Butyl 2-[4-chloro-2-({[(5-chloro-2-{[2,2-difluoro-2-(1-oxido-2-pyridinyl)ethyl]amino}-3-fluoro-4-pyridinyl)acetyl]amino}-methyl)phenyl]ethylcarbamate 19-1

$C_{28}H_{30}Cl_2F_3N_5O_4$, Mol. Wt.=628.484 (MS: M+H= 628.3)

EXAMPLE 20

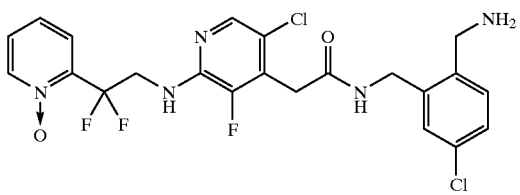

20-1

N-[2-(Aminomethyl)-5-chlorobenzyl]-2-(5-chloro-2-{[2,2-difluoro-2-(1-oxido-2-pyridinyl)ethyl]amino}-3-fluoro-4-pyridinyl)acetamide 20-1

$C_{22}H_{20}Cl_2F_3N_5O_2$, Mol. Wt. 514.338 (MS: M+H=514.2)

EXAMPLE 21

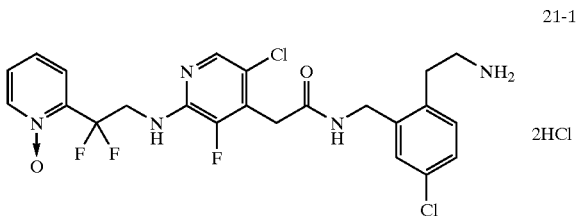

21-1

N-[2-(2-Aminoethyl)-5-chlorobenzyl]-2-(5-chloro-2-{[2,2-difluoro-2-(1-oxido-2-pyridinyl)ethyl]amino}-3-fluoro-4-pyridinyl)acetamide 21-1

$C_{23}H_{22}Cl_2F_3N_5O_2$, Mol. Wt.=528.365 (MS: M+H= 528.2)

EXAMPLE 22

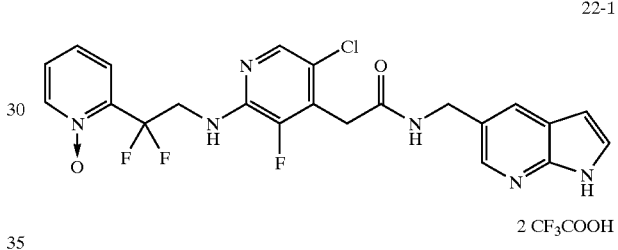

22-1

2-(5-Chloro-2-{[2,2-difluoro-2-(1-oxido-2-pyridinyl)ethyl]amino}-3-fluoro-4-pyridinyl)-N-(1H-pyrrolo[2,3-b]pyridin-5-ylmethyl)acetamide 22-1

$C_{22}H_{18}ClF_3N_6O_2$, Mol. Wt.=490.876 (MS: M+H=491.1)

EXAMPLE 23

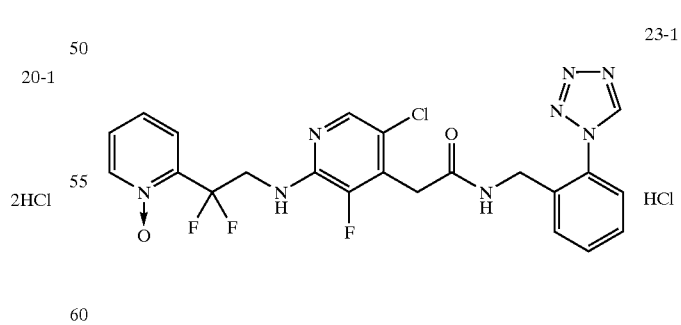

23-1

2-(5-Chloro-2-{[2,2-difluoro-2-(1-oxido-2-pyridinyl)ethyl]amino}-3-fluoro-4-pyridinyl)-N-[2-(1H-tetraazol-1-yl)benzyl]acetamide 23-1

$C_{22}H_{18}ClF_3N_8O_2$, Mol. Wt.=518.889 (MS: M+H=519.2)

EXAMPLE 24

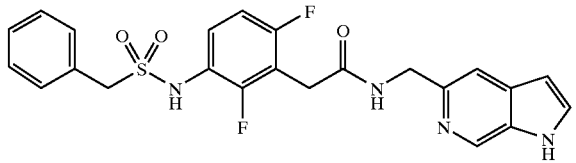

24-1

2-{3-[(benzylsulfonyl)amino]-2,6-difluorophenyl}-
N-(1H-pyrrolo[2,3-c]pyridin-5-ylmethyl)acetamide
24-1

Step 1

To a stirred mixture 2,6-difluorophenylacetonitrile (3.06 g, 20.0 mmol) in 30 mL of $H_2SO_4$ at 0° C. was added 12 mL of a 1:1 mixture of nitric acid and sulfuric acid. The reaction mixture stirred for 5 h and poured onto crushed ice. The resulting solid was filtered and air dried to give 2,6-difluoro-3-nitro-phenylacetamide.

$^1$H NMR (CDCl$_3$) δ 8.01 (m, 1H), 7.08 (m, 2H), 6.25 (bs, 1H), 3.75 (s, 2H) LCMS (M+Na)=239.0.

Step 2

A −15° C. solution containing 3.0 g (13.9 mmol) of the nitro compound from step 1 in 25 mL of MeOH was treated with a solution of 12.2 g (54.2 mmol) of stannous chloride dihydrate in 11.6 mL (139.0 mmol) of concentrated sulfuric acid. The ice bath was removed and the solution was stirred at ambient temperature for 16 h. The reaction mixture was quenched by the careful addition of saturated NaHCO$_3$ and the resulting solids were removed by filtration. The filtrate was extracted with 3×50 mL of EtOAc. The combined organics were washed with water (10 mL) and brine (10 mL) before being dried (MgSO$_4$). Evaporation of the solvent left 3-amino-2,6-difluorophenylacetamide which was used directly in the next step.

LCMS (M+1)=186.3.

Step 3

A solution of 500 mg (2.68 mmol) of the amide from step 2 in 10 mL of MeOH was treated with 0.5 mL of concentrated sulfuric acid. The resulting solution was heated at reflux over 16 h. The reaction mixture was cooled, evaporated and quenched by the careful addition of saturated NaHCO$_3$. The mixture was extracted with 3×10 mL of EtOAc. The combined organics were washed with water (2 mL) and brine (2 mL) before being dried (MgSO$_4$). Evaporation of the solvent left methyl 3-amino-2,6-difluorophenylacetate which was used directly in the next step.

$^1$H NMR (CDCl$_3$) δ 6.74 (m, 2H), 3.75 (s, 2H), 3.73 (s, 2H), 3.65 (bs, 2H). LCMS (M+1)=201.1.

Step 4

A solution containing 390 mg (1.94 mmol) of the aniline from step 3 in 6 mL of DCM and 1.6 mL (19.4 mmol) of pyridine was treated with 371 mg (1.94 mmol) of benzylsulfonyl chloride and the whole was stirred at ambient temperature for 16 h. The reaction mixture was diluted with 10 mL of DCM, washed with water (5×2 mL) and dried (MgSO$_4$). The resulting solid was triturated with ether and filtered to give methyl 3-(N-benzylsulfonylamino)-2,6-difluorophenylacetate.

$^1$H NMR (CDCl$_3$) δ 7.21–7.55 (m, 6H), 6.94 (t, 1H), 6.25 (bs, 1H), 4.38 (s, 2H), 3.75 (s, 2H), 3.68 (s, 2H).

Step 5

A solution of 177 mg (0.5 mmol) of the ester from step 4 above in 12 mL of dioxane and 4 mL of water was treated with 63 mg (1.5 mmol) of LiOH.H$_2$O at 0° C. The reaction mixture was stirred for 3 h and quenched to pH=3 with 1N HCl. The mixture was diluted with 35 mL of EtOAc and the organic phase was separated and washed with 10 mL of brine. The organic solution was dried over MgSO$_4$ and concentrated to dryness to leave crude carboxylic acid which was coupled in the next step without further purification.

Step 6

A solution containing 61 mg (0.18 mmol) of the carboxylic acid from step 5 above, 39 mg (0.18 mmol) of 5-aminomethyl-6-azaindole dihydrochloride, 38 mg (0.18 mmol) of EDC, 28 mg (0.18 mmol) of HOBT and 0.055 mL (0.54 mmol) of NMM in 3 mL of DMF were stirred at ambient temperature for 16 h. The reaction mixture was diluted with 10 mL of EtOAc, washed with water (5×2 mL) and dried (MgSO$_4$). The resulting solid was triturated with ether and filtered to afford the title compound 24-1.

LCMS (M+1)=472.4

EXAMPLE 25

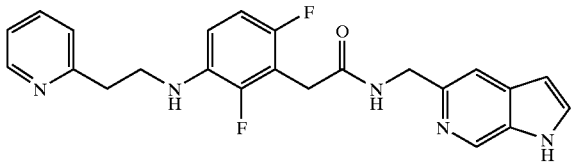

25-1

2-{2,6-difluoro-3-[(2-pyridin-2-ylethyl)amino]
phenyl}-N-(1H-pyrrolo[2,3-c]pyridin-5-ylmethyl)
acetamide 25-1

Step 1

A solution of 402 mg (2.0 mmol) of methyl 3-amino-2,6-difluorophenylacetate (prepared in step 3 of example 24) in 15 mL of MeOH was treated with 1.1 mL (20.0 mmol) of HOAc and 0.28 mL (2.6 mmol) of 2-vinylpyridine. The reaction mixture was stirred at reflux for 16 h. The mixture was cooled and the acetic acid was removed in vacuo. The residue was dissolved in EtOAc and washed with saturated NaHCO$_3$ (4×5 mL), water (1×10 mL) and brine. Column chromatography (1:4 EtOAc/Hex) afforded methyl 3-(2-pyridylethyl)amino-2,6-difluorophenylacetate.

$^1$H NMR (CDCl$_3$) δ 8.61 (d, 1H), 7.60 (t, 1H), 7.17 (m, 2H), 6.78 (t, 1H), 6.65 (m, 1H), 4.30 (bs, 1H), 3.75 (s, 2H), 3.68 (s, 2H), 3.55 (m, 2H), 3.07 (t, 2H). LCMS (M+1)=314.2.

Step 2

A solution of 70 mg (0.22 mmol) of the ester from step 1 above in 4 mL of dioxane and 1.5 mL of water was treated with 28 mg (0.66 mmol) of LiOH.H$_2$O at 0° C. The reaction mixture was stirred for 3 h and quenched to pH=7 with 1N HCl. The mixture was concentrated to dryness to leave crude carboxylic acid which was coupled in the next step without further purification.

Step 3

A solution containing 215 mg (0.736 mmol) of the carboxylic acid from step 2 above, 163 mg (0.736 mmol) of 5-aminomethyl-6-azaindole dihydrochloride, 141 mg (0.736 mmol) of EDC, 99 mg (0.736 mmol) of HOBT and 0.32 mL (2.94 mmol) of NMM in 3 mL of DMF were stirred at ambient temperature for 16 h. The reaction mixture was diluted with 10 mL of EtOAc, washed with water (5×2 L) and dried (MgSO$_4$). The resulting solid was triturated with ether and filtered to afford the title compound 25-1.

$^1$H NMR (CDCl$_3$) δ 8.61 (s, 1H), 8.55 (d, 1H), 7.60 (t, 1H), 7.51 (s, 1H), 7.40 (d, 1H), 7.17 (m, 2H), 6.78 (t, 1H), 6.65 (m, 1H), 6.51 (d, 1H), 4.57 (d, 2H), 3.65 (s, 2H), 3.53 (t, 2H), 3.01 (t, 2H), 3.07 (t, 2H). LCMS (M+1)=422.2.

EXAMPLE 26

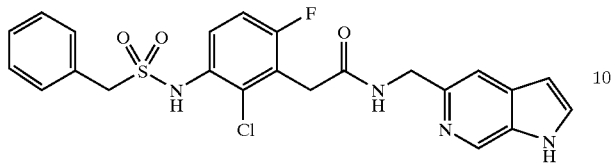

26-1

2-{3-[(benzylsulfonyl)amino]-2-chloro-6-fluorophenyl}-N-(1H-pyrrolo[2,3-c]pyridin-5-ylmethyl)acetamide 26-1

This compound was prepared in an analogous fashion using the 6 step procedure outlined in example 24 starting from 2-chloro-6-fluorophenylacetonitrile.

LCMS (M+1)=488.3

EXAMPLE 27

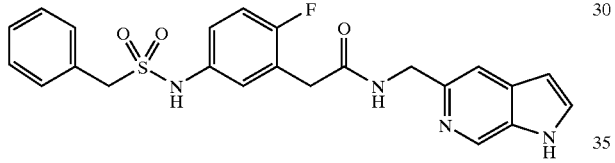

27-1

2-{5-[(benzylsulfonyl)amino]-2-fluorophenyl}-N-(1H-pyrrolo[2,3-c]pyridin-5-ylmethyl)acetamide 27-1

This compound was prepared in an analogous fashion using the 6 step procedure outlined in example 24 starting from 2-fluorophenylacetonitrile.

LCMS (M+1)=454.2.

EXAMPLE 28

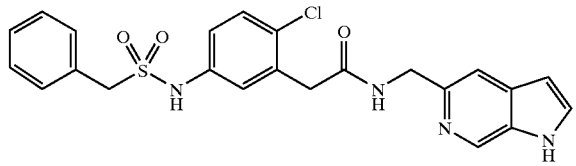

28-1

2-{5-[(benzylsulfonyl)amino]-2-chlorophenyl}-N-(1H-pyrrolo[2,3-c]pyridin-5-ylmethyl)acetamide 28-1

This compound was prepared in an analogous fashion using the 6 step procedure outlined in example 24 starting from 2-chlorophenylacetonitrile. LCMS(M+1)=471.1.

EXAMPLE 29

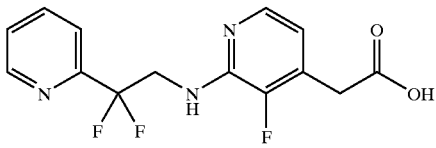

29-3

{2-[(2,2-difluoro-2-pyridin-2-ylethyl)amino]-3-fluoropyridin-4-yl}acetic acid (29-3)

Step 1

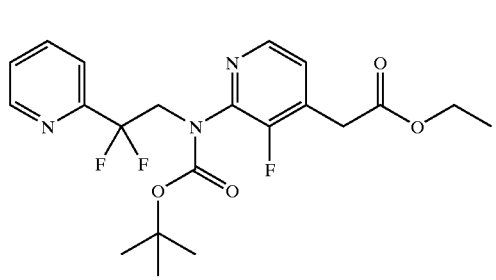

29-1

Ethyl{2-[(tert-butoxycarbonyl)(2,2-difluoro-2-pyridin-2-ylethyl)amino]-3-fluoropyridin-4-yl}acetate (29-1)

To a solution of 9.83 g (20.0 mmol) of ethyl {2-[(tert-butoxycarbonyl)(2,2-difluoro-2-pyridin-2-ylethyl)amino]-5-chloro-3,6-difluoropyridin-4-yl}acetate in 80 mL THF was added 1.54 g (22.0 mmol) NaSMe as a slurry in 80 mL DMF. After 40 min at room temperature, the rxn was poured onto 500 mL ether/400 mL H$_2$O/9 mL 1N HCl. The layers were mixed and then separated. The ether layer was washed with 400 mL saturated sodium bicarbonate solution and 400 mL brine, dried over Na$_2$SO$_4$, filtered, and concentrated in vacuo to give 10.10 g yellow oil. To a solution of 10.05 g of this oil in 60 mL EtOH was added a 10 mL thick EtOH slurry of Raney nickel. Then over a period of 5 h, an additional 61 mL of the Raney nickel slurry was added in six portions. The mixture was then filtered over celite, rinsed with 600 mL MeOH, and concentrated in vacuo. Purification by automated flash chromatography (120 g silica cartridge, linear gradient 5–40% EtOAc/hexane over 40 min, 90 mL/min flow rate) afforded ethyl {2-[(tert-butoxycarbonyl)(2,2-difluoro-2-pyridin-2-ylethyl)amino]-3-fluoropyridin-4-yl}acetate 29-1.

$^1$H NMR (CDCl$_3$, 400 MHz) δ8.554 (d, 1H, J=4.67 Hz, ArH); 8.154 (d, 1H, J=4.95 Hz, ArH); 7.774–7.732 (m, 1H, ArH); 7.625 (d, 1H, J=7.87 Hz, ArH); 7.297 (dd, 1H, J=5.08 Hz, 7.19 Hz, ArH); 7.133 (t, 1H, J=4.95 Hz, ArH); 4.750 (t, 2H, J=13.51 Hz, CH$_2$); 4.188 (dd, 2H, J=7.10 Hz, 14.24 Hz, CH$_2$); 3.659 (s, 2H, CH$_2$); 1.353 (s, 9H, C(CH$_3$)$_3$); 1.269 (t, 3H, J=7.14 Hz, CH$_3$); MS (Electrospray): m/z 440.1 (M$^+$H).

Step 2

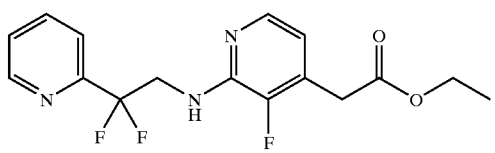

Ethyl{2-[(2,2-difluoro-2-pyridin-2-ylethyl)amino]-3-fluoropyridin-4-yl}acetate (29-2)

Through a 0° C. solution of 0.218 g (0.496 mmol) ethyl {2-[(tert-butoxycarbonyl)(2,2-difluoro-2-pyridin-2-ylethyl)amino]-3-fluoropyridin-4-yl}acetate 29-1 in 10 mL EtOAc was passed a steady stream of HCl gas for 10 min. The reaction was stirred at 0° C. for 1.5 h and then at room temperature for 10 min. The reaction mixture was then flushed with $N_2$ and poured onto 150 mL EtOAc/50 mL 2M NaOH/7 mL conc NaOH. The layers were mixed and then separated. The aqueous layer was back extracted with 50 mL EtOAc. The combined organics were washed w/50 mL water and 50 mL brine, dried over $Na_2SO_4$, filtered, and concentrated in vacuo. Purification by automated flash chromatography (40 g silica cartridge, linear gradient 0–50% EtOAc/hexane over 30 min, 30 mL/min flow rate) gave ethyl {2-[(2,2-difluoro-2-pyridin-2-ylethyl)amino]-3-fluoropyridin-4-yl}acetate 29-2. $^1$H NMR (CDCl$_3$, 400 MHz) δ8.663 (d, 1H, J=4.67 Hz, ArH); 7.829–7.790 (m, 2H, ArH); 7.693 (d, 1H, J=7.14 Hz, ArH); 7.377 (t, 1H, J=6.14 Hz, ArH); 6.489 (t, 1H, J=4.99 Hz, ArH); 4.492–4.405 (m, 2H, CH$_2$); 4.199–4.145 (m, 2H, CH$_2$); 3.585 (s, 2H, CH$_2$); 1.276–1.237 (m, 3H, CH$_3$); MS (Electrospray): m/z 340.1 (M$^+$H).

Step 3

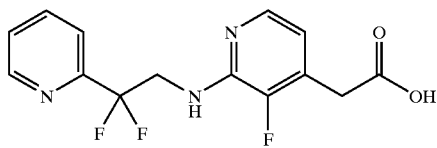

{2-[(2,2-difluoro-2-pyridin-2-ylethyl)amino]-3-fluoropyridin-4-yl}acetic acid (29-3)

To a solution of 0.159 g (0.469 mmol) ethyl {2-[(2,2-difluoro-2-pyridin-2-ylethyl)amino]-3-fluoropyridin-4-yl}acetate 29-2 in 1 mL MeOH was added 469 uL (0.469 mmol, 1M aqueous solution) LiOH. The reaction was stirred at room temperature for 23 h. To the reaction was added 38.7 uL (0.469 mmol, 12M aqueous solution) HCl. The mixture was stirred for 10 min, concentrated in vacuo, and placed under vacuum alongside $P_2O_5$ to yield {2-[(2,2-difluoro-2-pyridin-2-ylethyl)amino]-3-fluoropyridin-4-yl}acetic acid 29-3. $^1$H NMR (CD$_3$OD, 400 MHz) δ8.606 (d, 1H, J=4.77 Hz, ArH); 7.894 (t, 1H, J=7.83 Hz, ArH); 7.692 (d, 1H, J=7.69 Hz, ArH); 7.609 (d, 1H, J=5.22 Hz, ArH); 7.458 (t, 1H, J=6.05 Hz, ArH); 6.499 (t, 1H, J=4.99 Hz, ArH); 4.324 (t, 2H, J=13.92 Hz, CH$_2$); 3.572 (s, 2H, CH$_2$); MS (Electrospray): m/z 312.0 (M$^+$H).

EXAMPLE 30

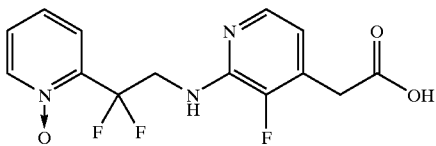

(2-{[2,2-difluoro-2-(1-oxidopyridin-2-yl)ethyl]amino}-3-fluoropyridin-4-yl)acetic acid (30-3)

Step 1

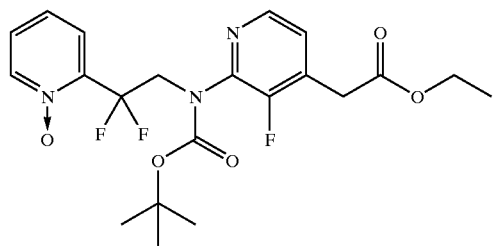

Ethyl(2-{(tert-butoxycarbonyl)[2,2-difluoro-2-(1-oxidopyridin-2-yl)ethyl]amino}-3-fluoropyridin-4-yl)acetate (30-1)

To a solution of 0.372 g (0.847 mmol) ethyl {2-[(tert-butoxycarbonyl)(2,2-difluoro-2-pyridin-2-ylethyl)amino]-3-fluoropyridin-4-yl}acetate in 8 mL dichloroethane was added 0.199 g (0.889 mmol) m-chloroperoxybenzoic acid. After 16 h at room temperature, the mixture was heated to 60° C. for 3 h and then cooled to room temperature, diluted with 100 mL EtOAc, washed with 60 mL 0. 1M aqueous NaOH and 60 mL brine, dried over Na$_2$SO$_4$, filtered, and concentrated in vacuo. Purification by automated flash chromatography (40 g silica cartridge, linear gradient 0–5% MeOH/CH$_2$Cl$_2$ over 20 min, 30 mL/min flow rate) afforded a 1.7 to 1 mixture of ethyl(2-{(tert-butoxycarbonyl)[2,2-difluoro-2-(1-oxidopyridin-2-yl)ethyl]amino}-3-fluoropyridin-4-yl)acetate 30-1 and ethyl(2-{(tert-butoxycarbonyl)[2,2-difluoro-2-(1-oxidopyridin-2-yl)ethyl]amino}-3-fluoropyridin-4-yl)acetate 30-1. $^1$H NMR (CDCl$_3$, 400 MHz) δ8.286 (d, 1H, J=5.76 Hz, ArH); 8.139 (d, 1H, J=4.85 Hz, ArH); 7.615 (dd, 1H, J=2.75 Hz, 7.23 Hz, ArH); 7.346–7.299 (m, 2H, ArH); 7.135 (t, 1H, J=4.95 Hz, ArH); 5.029 (t, 2H, J=11.45 Hz, CH$_2$); 4.236–4.165 (m, 2H, CH$_2$); 3.676 (s, 2H, CH$_2$); 1.291–1.256 (m, 12H, CH$_3$ and C(CH$_3$)$_3$); MS (Electrospray): m/z 456.1 (M$^+$H).

Step 2

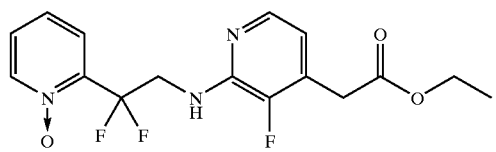

Ethyl(2-{[2,2-difluoro-2-(1-oxidopyridin-2-yl)ethyl]amino}-3-fluoropyridin-4-yl)acetate (30-2)

Through a 0° C. solution of 0.221 g (0.485 mmol) ethyl(2-{(tert-butoxycarbonyl)[2,2-difluoro-2-(1- oxidopyridin-2-yl)ethyl]amino}-3-fluoropyridin-4-yl) acetate 30-1, contaminated with ethyl(2-{(tert-butoxycarbonyl)[2,2-difluoro-2-(1-oxidopyridin-2-yl)ethyl]amino}-3-fluoropyridin-4-yl)acetate, in 3 mL EtOAc was passed a steady stream of HCl gas for 20 min. The reaction was stirred at 0° C. for 20 min. The mixture was then flushed with $N_2$ and poured onto 200 mL EtOAc/50 mL 2.0M NaOH/7 mL conc NaOH. The layers were mixed and then separated. The aqueous layer was back extracted with 25 mL EtOAc. The combined organics were washed w/100 mL water and 100 mL brine, dried over $Na_2SO_4$, filtered, and concentrated in vacuo. Purification by automated flash chromatography (40 g silica cartridge, linear gradient 0–5% MeOH/$CH_2Cl_2$ over 30 min, 30 mL/min flow rate) provided ethyl(2-{[2,2-difluoro-2-(1-oxidopyridin-2-yl)ethyl]amino}-3-fluoropyridin-4-yl)acetate 30-2. $^1$H NMR (CDCl$_3$, 400 MHz) δ8.288 (d, 1H, J=6.41 Hz, ArH); 7.727 (d, 1H, J=5.13 Hz, ArH); 7.622 (dd, 1H, J=2.20 Hz, 7.87 Hz, ArH); 7.363–7.323 (m, 1H, ArH); 7.297–7.257 (m, 1H, ArH); 6.455 (t, 1H, J=4.95 Hz, ArH); 4.751–4.663 (m, 2H, CH$_2$); 4.164 (dd, 2H, J=7.14 Hz, 14.28 Hz, CH$_2$); 3.560 (s, 2H, CH$_2$); 1.254 (t, 3H, J=7.15 Hz, CH$_3$); MS (Electrospray): m/z 356.1 (M$^+$H).

Step 3

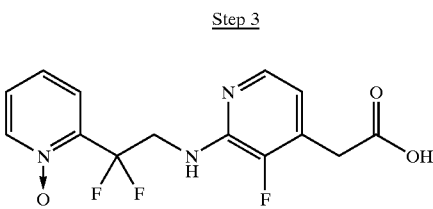

(2-{[2,2-difluoro-2-(1-oxidopyridin-2-yl)ethyl]amino}-3-fluoropyridin-4-yl)acetic acid (30-3)

To a solution of 0.064 g (0.18 mmol) ethyl(2-{[2,2-difluoro-2-(1-oxidopyridin-2-yl)ethyl]amino}-3-fluoropyridin-4-yl)acetate 30-2 in 1 mL MeOH was added 198 uL (0.198 mmol, 1M aqueous solution) LiOH. The reaction was stirred at room temperature for 19 h. To the mixture was added 36 uL (0.036 mmol, 1M aqueous solution). After an additional 24 h, 54 uL (0.054 mmol, 1M aqueous solution) more LiOH was added. After an another 4 h at room temperature, 23.8 uL (0.288 mmol, 12M aqueous solution) HCl was added. The reaction was stirred for 5 min and then concentrated in vacuo to give (2-{[2,2-difluoro-2-(1-oxidopyridin-2-yl)ethyl]amino}-3-fluoropyridin-4-yl)acetic acid 30-3. $^1$H NMR (CD$_3$OD, 400 MHz) δ8.426 (d, 1H, J=5.86 Hz, ArH); 7.765 (dd, 1H, J=2.34 Hz, 7.37 Hz, ArH); 7.628–7.565 (m, 3H, ArH); 6.646 (t, 1H, J=5.36 Hz, ArH); 4.636 (t, 2H, J=13.60 Hz, CH$_2$); 3.659 (s, 2H, CH$_2$); MS (Electrospray): m/z 328.0 (M$^+$H).

Using the coupling step illustrated in Schemes 1a and 1b, compounds describes in Examples 31–46 were prepared.

EXAMPLE 31

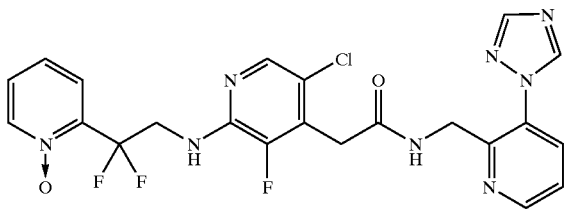

2-(5-chloro-2-{[2,2-difluoro-2-(1-oxidopyridin-2-yl)ethyl]amino}-3-fluoropyridin-4-yl)-N-{[3-(1H-1,2,4-triazol-1-yl)pyridin-2-yl]methyl}acetamide (31-1)

MS (Electrospray): m/z M+H=519.1264

EXAMPLE 32

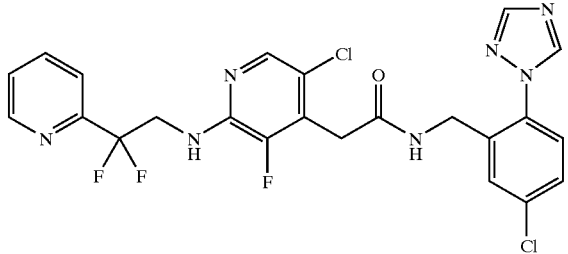

2-{5-chloro-2-[(2,2-difluoro-2-pyridin-2-ylethyl)amino]-3-fluoropyridin-4-yl1}-N-[5-chloro-2-(1H-1,2,4-triazol-1-yl)benzyl]acetamide (32-1)

MS (Electrospray): m/z M+H=536.0973

EXAMPLE 33

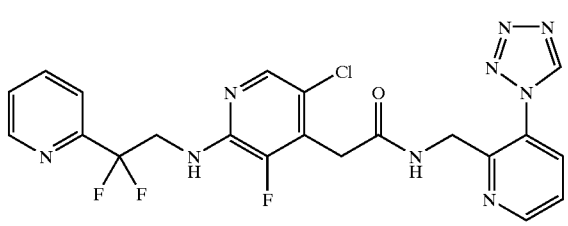

2-{5-chloro-2-[(2,2-difluoro-2-pyridin-2-ylethyl)amino]-3-fluoropyridin-4-yl}-N-{[3-(1H-tetraazol-1-yl)pyridin-2-yl]methyl}acetamide (33-1)

MS (Electrospray): m/z M+H=504.1294

EXAMPLE 34

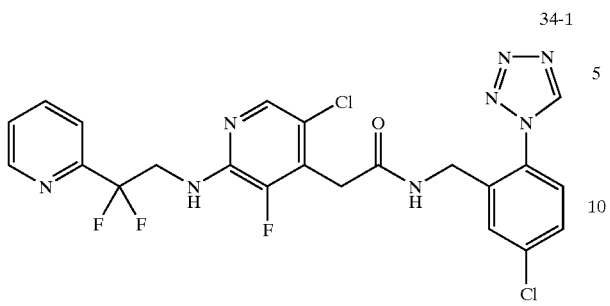

2-{5-chloro-2-[(2,2-difluoro-2-pyridin-2-ylethyl)amino]-3-fluoropyridin-4-yl}-N-[5-chloro-2-(1H-tetraazol-1-yl)benzyl]acetamide (34-1)

MS (Electrospray): m/z M+H=537.0934

EXAMPLE 35

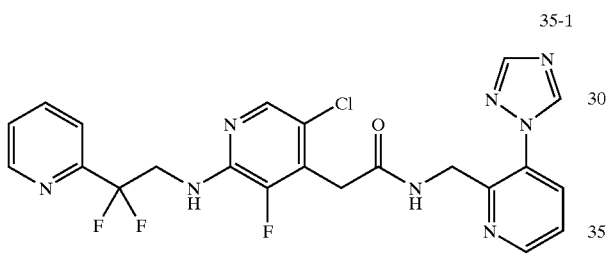

N-[3-(1H-1,2,4-triazol-1-yl)pyridin-2-yl]methyl-2-{5-chloro-2-[(2,2-difluoro-2-pyridin-2-ylethyl)amino]-3-fluoropyridin-4-yl}acetate (35-1)

MS (Electrospray): m/z M+H=503.1320

EXAMPLE 36

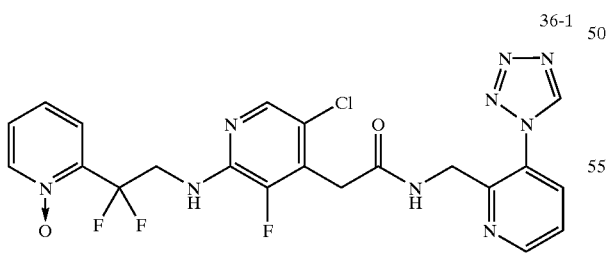

N-[3-(1H-tetraazol-1-yl)pyridin-2-yl]methyl-2-(5-chloro-2-{[2,2-difluoro-2-(1-oxidopyridin-2-yl)ethyl]amino}-3-fluoropyridin-4-yl)acetate (36-1)

MS (Electrospray): m/z M+H=520.1226

EXAMPLE 37

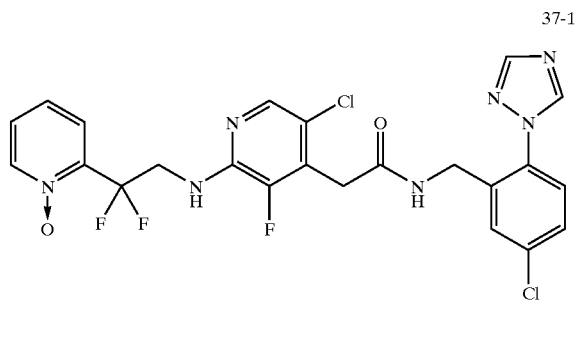

N-[5-chloro-2-(1H-1,2,4-triazol-1-yl)benzyl]-2-(5-chloro-2-{[2,2-difluoro-2-(1-oxidopyridin-2-yl)ethyl]amino}-3-fluoropyridin-4-yl)acetate (37-1)

MS (Electrospray): m/z M+H=552.0934

EXAMPLE 38

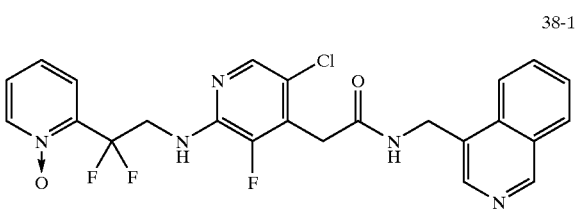

2-(5-chloro-2-{[2,2-difluoro-2-(1-oxidopyridin-2-yl)ethyl]amino}-3-fluoropyridin-4-yl)-N-(isoquinolin-4-ylmethyl)acetamide (38-1)

MS (Electrospray): m/z M+H=502.1256

EXAMPLE 39

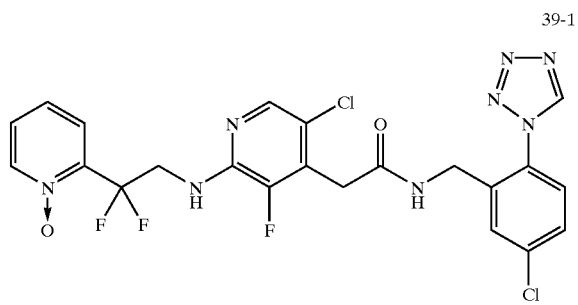

N-[5-chloro-2-(1H-tetraazol-1-yl)benzyl]-2-(5-chloro-2-{[2,2-difluoro-2-(1-oxidopyridin-2-yl)ethyl]amino}-3-fluoropyridin-4-yl)acetate (39-1)

MS (Electrospray): m/z M+H=553.0885

EXAMPLE 40

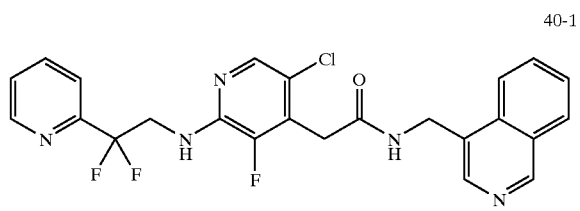

2-{5-chloro-2-[(2,2-difluoro-2-pyridin-2-ylethyl)amino]-3-fluoropyridin-4-yl}-N-(isoquinolin-4-ylmethyl)acetamide (40-1)

MS (Electrospray): m/z M+H=486.1309

EXAMPLE 41

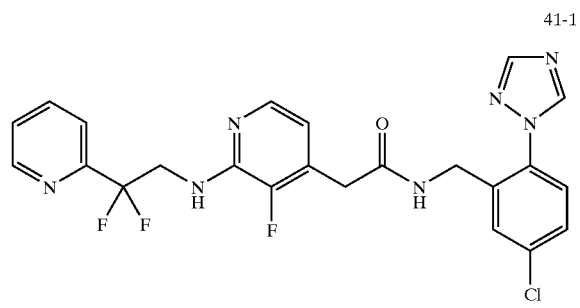

N-[5-chloro-2-(1H-1,2,4-triazol-1-yl)benzyl]-2-{2-[(2,2-difluoro-2-pyridin-2-ylethyl)amino]-3-fluoropyridin-4-yl}acetamide (41-1)

MS (Electrospray): m/z M+H=502.1406

EXAMPLE 42

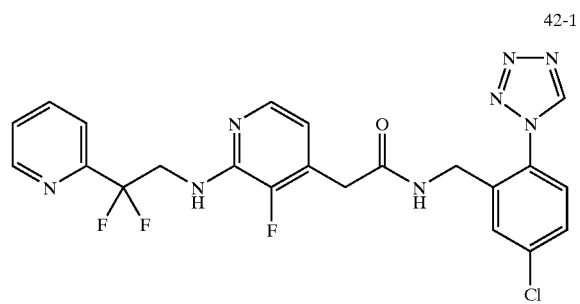

N-[5-chloro-2-(1H-tetraazol-1-yl)benzyl]-2-{2-[(2,2-difluoro-2-pyridin-2-ylethyl)amino]-3-fluoropyridin-4-yl}acetamide (42-1)

MS (Electrospray): m/z M+H=503.1336

EXAMPLE 43

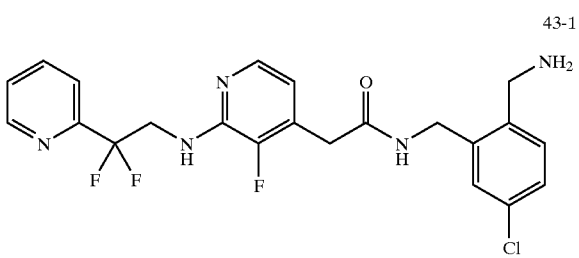

N-[2-(aminomethyl)-5-chlorobenzyl]-2-{2-[(2,2-difluoro-2-pyridin-2-ylethyl)amino]-3-fluoropyridin-4-yl}acetamide (43-1)

MS (Electrospray): m/z M+H=464.1456

EXAMPLE 44

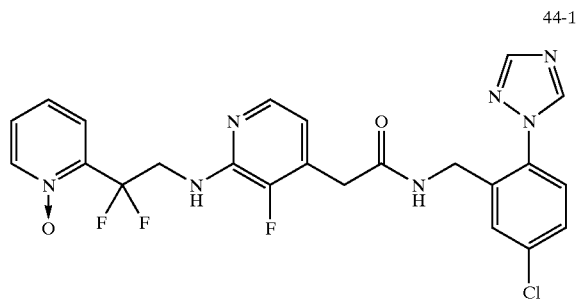

N-[5-chloro-2-(1H-1,2,4-triazol-1-yl)benzyl]-2-(2-{[2,2-difluoro-2-(1-oxidopyridin-2-yl)ethyl]amino}-3-fluoropyridin-4-yl)acetamide (44-1)

MS (Electrospray): m/z M+H=518.1308

EXAMPLE 45

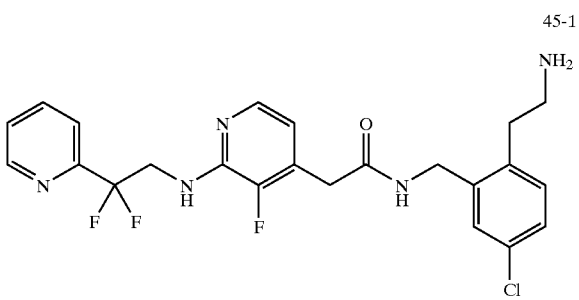

N-[2-(2-aminoethyl)-5-chlorobenzyl]-2-{2-[(2,2-difluoro-2-pyridin-2-ylethyl)amino]-3-fluoropyridin-4-yl}acetamide (45-1)

MS (Electrospray): m/z M+H=478.1608

EXAMPLE 46

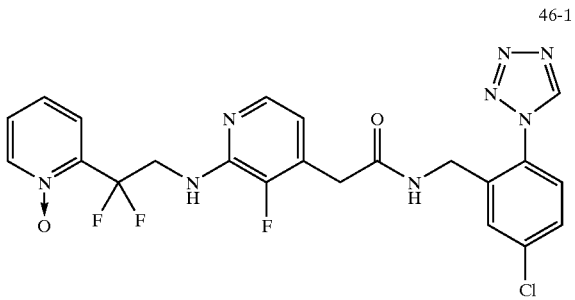

N-[5-chloro-2-(1H-tetraazol-1-yl)benzyl]-2-(2-{[2,2-difluoro-2-(1-oxidopyridin-2-yl)ethyl]amino}-3-fluoropyridin-4-yl)acetamide (46-1)

MS (Electrospray): m/z M+H=519.1251

Typical tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

In order to determine activity of compounds prepared according to the process of the invention, assays of human α-thrombin and human trypsin were performed by the methods substantially as described in *Thrombosis Research*, Issue No. 70, page 173 (1993) by S. D. Lewis et al.

Activity assays were performed by diluting a stock solution of substrate at least tenfold to a final concentration $\leq 0.1$ $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared to $K_m/[S]$ and $[I]/e$ (where $[S]$, $[I]$, and e respectively represent the total concentrations, of substrate, inhibitor and enzyme), the equilibrium constant ($K_i$) for dissociation of the inhibitor from the enzyme can be obtained from the dependence of $V_o/v_i$ on $[I]$ shown in the equation:

$$V_o/V_i = 1 + [I]/K_i.$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The inhibitory activity of compounds of the invention against human thrombin, represented by Ki, is less than 24 nM. These are selective compounds, as evidenced by their inhibitory activity against human trypsin (represented by Ki), which is at least 1000 nM.

EXAMPLE 47

Tablet Preparation

Tablets containing 25.0, 50.0, and 100.0 mg., respectively, of the following active compounds are prepared as illustrated below (compositions A-I), Active I is N-[2-(2-aminoethyl)-5-chlorobenzyl]-2-(5-chloro-2-{[2,2-difluoro-2-(2-pyridinyl)ethyl]amino}-3-fluoro-4-pyridinyl)acetamide;

Active II is 2-(5-Chloro-2-{[2,2-difluoro-2-(1-oxido-2-pyridinyl)ethyl]amino}-3-fluoro-4-pyridinyl)-N-(2-fluorobenzyl)acetamide;

Active III is tert-Butyl 2-({[(5-chloro-2-{[2,2-difluoro-2-(1-oxido-2-pyridinyl)ethyl]amino}-3-fluoro-4-pyridinyl)acetyl]amino}methyl)benzylcarbamate.

| Component | Amount-mg | | | | | | | | |
|---|---|---|---|---|---|---|---|---|---|
| | A | B | C | D | E | F | G | H | I |
| Active I | 25 | 50 | 100 | — | — | — | — | — | — |
| Active II | — | — | — | 25 | 50 | 100 | — | — | — |
| Active III | — | — | — | — | — | — | 25 | 50 | 100 |
| Microcrystalline Cellulose | 37.25 | 100 | 200 | 37.25 | 100 | 200 | 37.25 | 100 | 200 |
| Modified food corn starch | 37.25 | 4.25 | 8.5 | 37.25 | 4.25 | 8.5 | 37.25 | 4.25 | 8.5 |
| Magnesium stearate | 0.5 | 0.75 | 1.5 | 0.5 | 0.75 | 1.5 | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 48

Tablet Preparation

Exemplary compositions of 2-(Aminomethyl)benzyl (5-chloro-2-{[2,2-difluoro-2-(1-oxido-2-pyridinyl)ethyl]amino}-3-fluoro-4-pyridinyl)acetate (Active IV) tablets are shown below:

| Component | 0.25 mg | 2 mg | 10 mg | 50 mg |
|---|---|---|---|---|
| Active IV | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet Preparation via Direct Compression

Active IV, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation via Dry Granulation

Alternatively, a dry powder blend is compacted under modest forces and remilled to afford granules of specified particle size. The granules are then mixed with magnesium stearate and tabletted as stated above.

EXAMPLE 49

Intravenous Formulations

Intravenous formulations of (Active IV) were prepared according to general intravenous formulation procedures.

| Component | Estimated range |
|---|---|
| Active IV | 0.12–0.61 mg |
| D-glucuronic acid* | 0.5–5 mg |
| Mannitol NF | 50–53 mg |
| 1 N Sodium Hydroxide | q.s. pH 3.9–4.1 |
| Water for injection | q.s. 1.0 mL |

Exemplary compositions A–C are as follows:

| Component | A | B | C |
|---|---|---|---|
| Active IV | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1 N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base
**0.25 mg free base
***0.12 mg free base

Various other buffer acids, such as L-lactic acid, acetic acid, citric acid or any pharmaceutically acceptable acid/ conjugate base with reasonable buffering capacity in the pH range acceptable for intravenous administration may be substituted for glucuronic acid.

What is claimed is:
1. A compound having the formula:

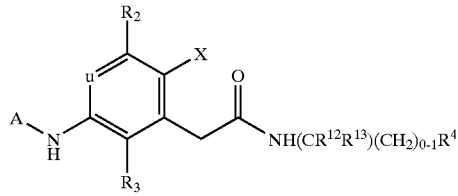

wherein
u is N;
A is —$CH_2C(Y)_2R^1$ or —$S(O)_2CH_2R^1$;
$R^1$ is
1) a 6-membered non-heterocyclic unsaturated ring system, unsubstituted, monosubstituted or disubstituted, same or different, with $R^8$,
2) a 6-membered heterocyclic saturated ring system wherein 1 or 2 ring atoms are independently selected from the group of heteroatoms consisting of N, O and S, wherein the ring is unsubstituted, monosubstituted or disubstituted, same or different, with $R^8$, or
3)

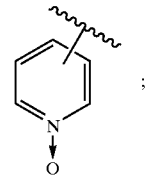

;

$R^2$ is hydrogen or F;
$R^3$ is hydrogen or halogen;
X is hydrogen, halogen, $C_{1-4}$ alkyl, CN or $CF_3$;
Y is hydrogen, $C_{1-4}$ alkyl, or F;
$R^4$ is
1) a 6-membered non-heterocyclic unsaturated ring system, unsubstituted, monosubstituted, or disubstituted, same or different, with $R^9$,
2) a 5- or 6-membered monocyclic heteroatom-containing unsaturated ring system wherein 1 or 2 ring atoms is selected from N, wherein the ring is unsubstituted or monosubstituted with $R^9$,
3) a 9- or 10-membered bicyclic heteroatom-containing unsaturated ring system wherein 1 or 2 ring atoms is selected from N, wherein the ring is unsubstituted or monosubstituted with $R^9$,
4) —$CH_2C(O)NHC(NH)NH_2$;
$R^8$ and $R^9$ are independently
1) halogen,
2) $C_{1-8}$ alkyl,
3) $C_{1-4}$ alkylene $C_{3-7}$ cycloalkyl
4) $(CH_2)_{1-2}NH_2$,
5) a 5-membered heterocylcic unsaturated ring having 3 or 4 N atoms, wherein the ring is unsubstituted, monosubstituted, or disubstituted, same or different, with $C_{1-8}$ alkyl, $C_{3-7}$ cycloalkyl, $C_{1-4}$ alkylene $C_{3-7}$ cycloalkyl, $NH_2$, or $(CH_2)_{0-4}X^2$ $(CH_2)_{0-3}CH_3$, wherein $X^2$ is a bond, S, S(O), $S(O)_2$, O, or NH,
6) —$OCH_2C(O)NHR^{10}$, or
7) —$(CH_2)_{1-2}NHC(O)OR^{11}$;

$R^{10}$ is $C_{1-4}$ alkyl or $C_{3-7}$ cycloalkyl;

$R^{11}$ is $C_{1-4}$ alkyl; and $R^{12}$ and $R^{13}$, same or different, are selected from the group consisting of hydrogen and $C_{1-4}$ alkyl, or a pharmaceutically acceptable salt thereof.

2. A compound of claim 1, or a pharmaceutically acceptable salt thereof, wherein Y is hydrogen, $CH_3$, or F, and $R^3$ is hydrogen, Cl, or F.

3. A compound of claim 2, or a pharmaceutically acceptable salt thereof, wherein X is hydrogen, F, Cl, Br, $C_{1-4}$ alkyl, CN or $CF_3$.

4. A compound of claim 3, or a pharmaceutically acceptable salt thereof, wherein $R^1$ is

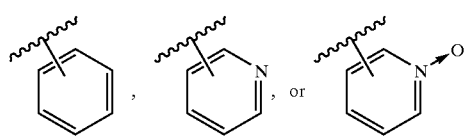

5. A compound of claim 4, or a pharmaceutically acceptable salt thereof, wherein $R^4$ is $CH_2C(O)NHC(NH)NH_2$,

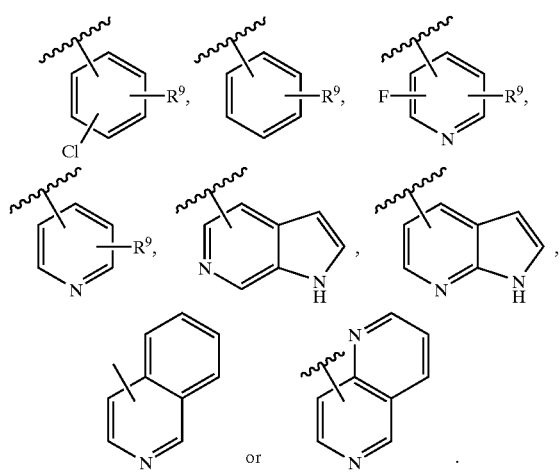

6. A compound of claim 5, or a pharmaceutically acceptable salt thereof, wherein $R^9$ is selected from the group consisting of Cl, F, —$CH_3$, —$OCH_2C(O)NHCH_2CH_3$, —$(CH_2)_{1-2}NHC(O)OC(CH_3)_3$, —$(CH_2)_{1-2}NH_2$,

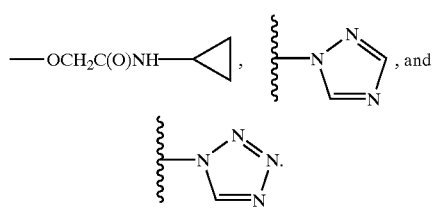

7. A compound of claim 6, or a pharmaceutically acceptable salt thereof, wherein A is

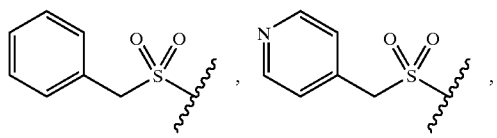

-continued

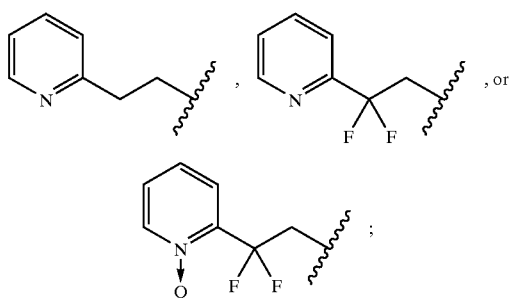

u is N or CH;

$R^2$ is hydrogen or F;

$R^3$ is Cl or F;

X is hydrogen, Cl or F;

$R^{12}$ is hydrogen;

$R^{13}$ is hydrogen or $CH_3$;

$R^4$ is

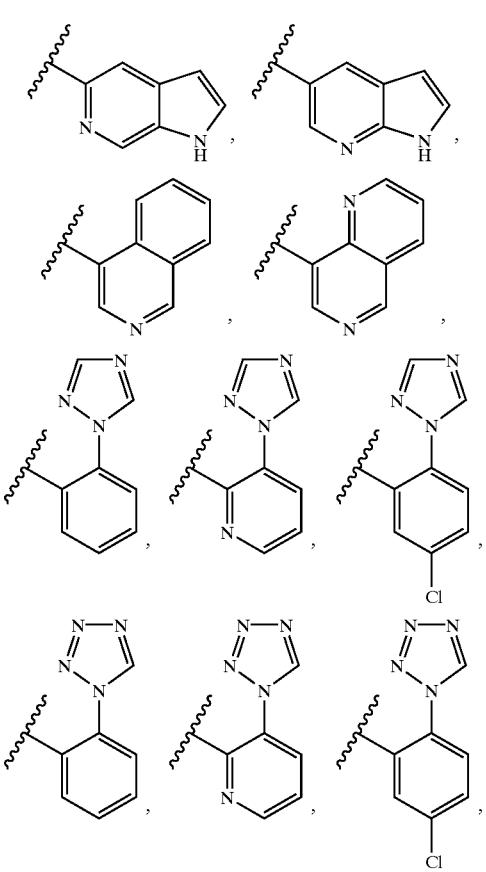

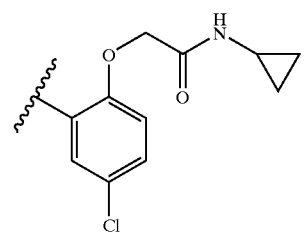

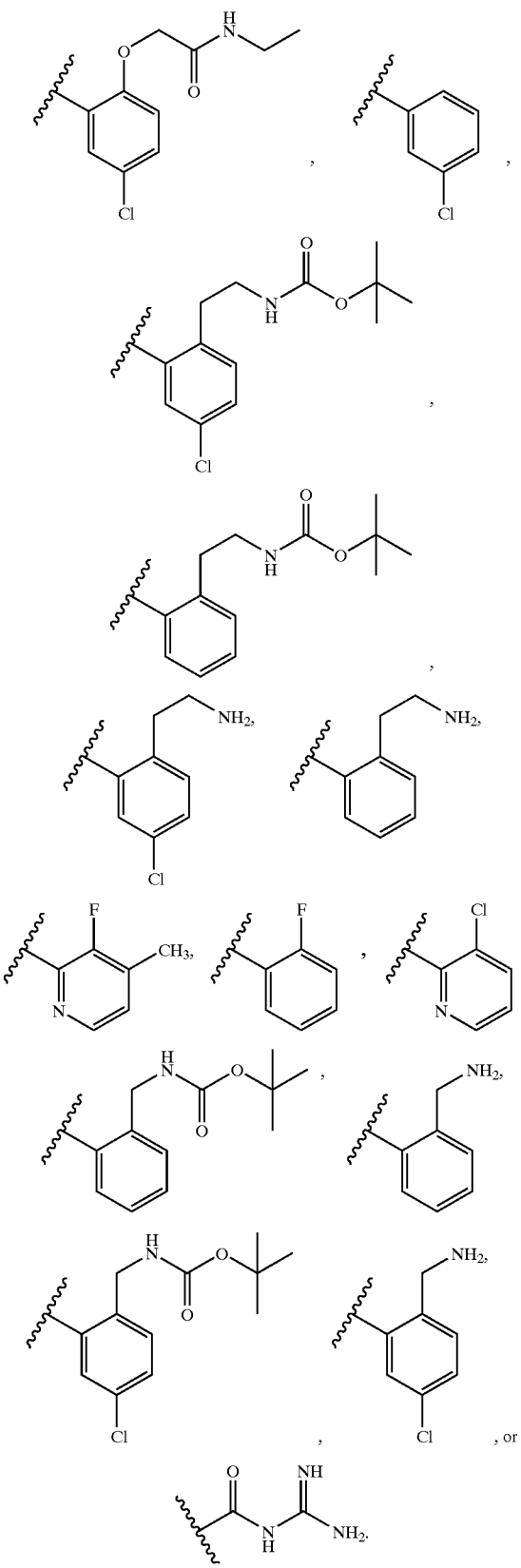
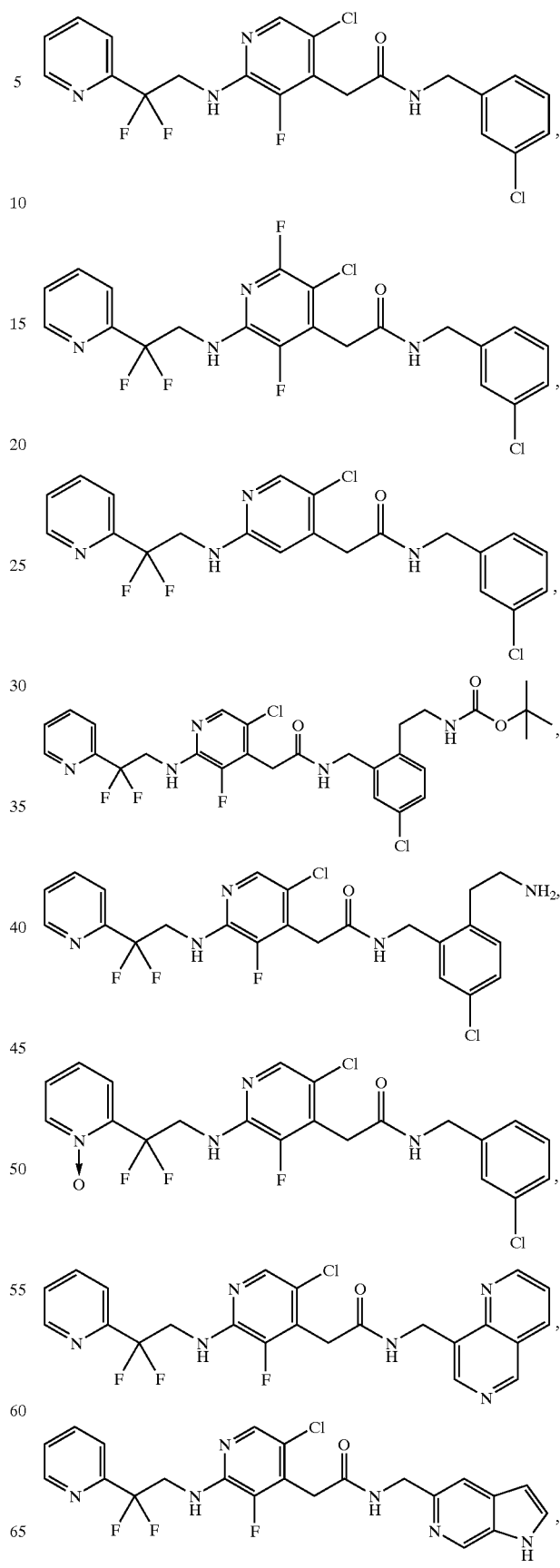
8. A compound of claim 7, or a pharmaceutically acceptable salt thereof, selected from the group consisting of 101
-continued
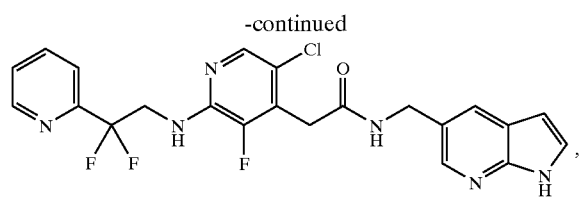
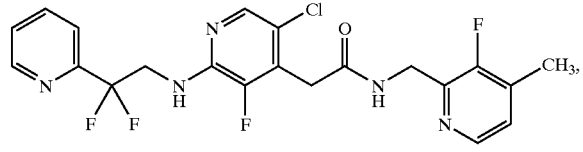
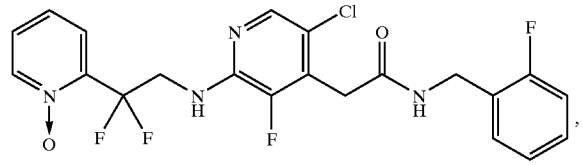
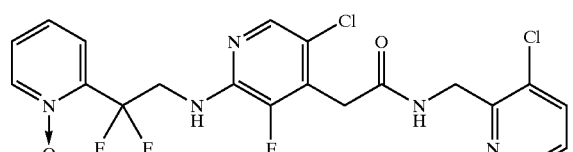
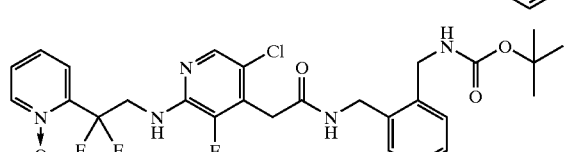
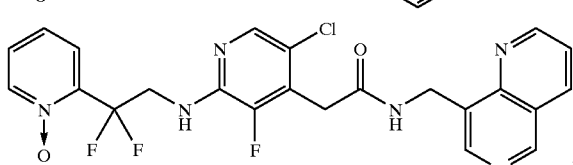
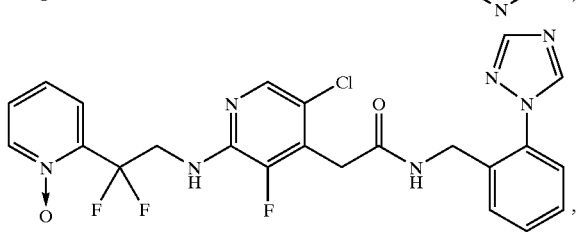
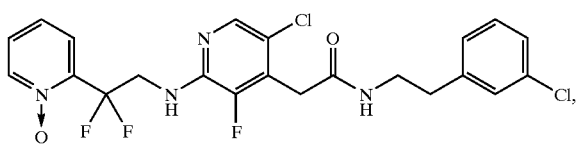
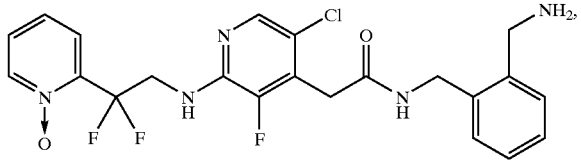
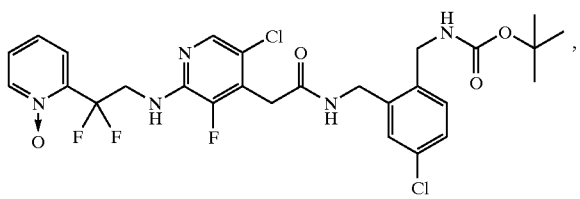
102
-continued
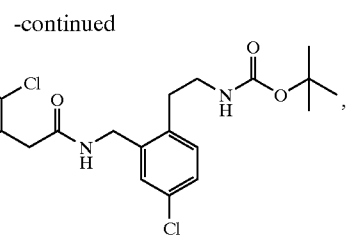
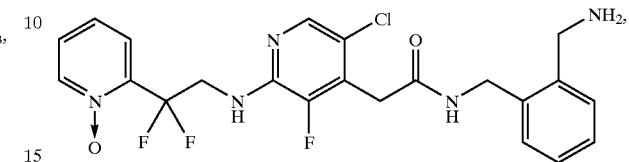
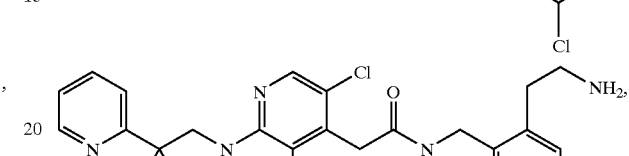
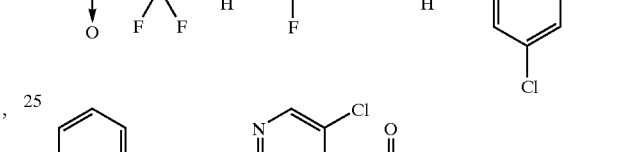
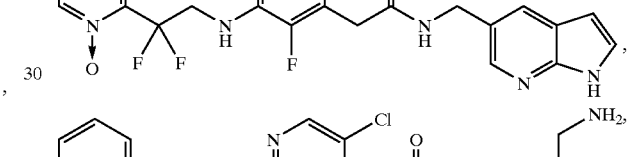
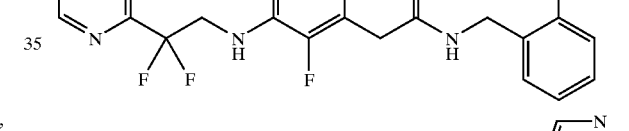
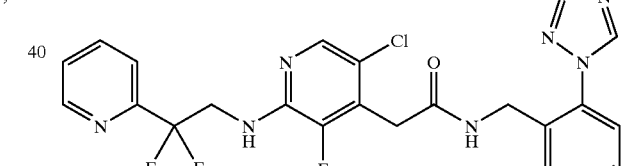
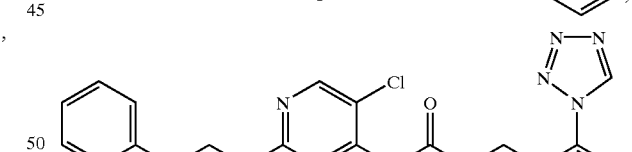
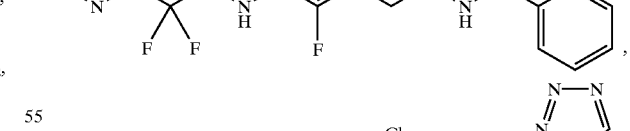
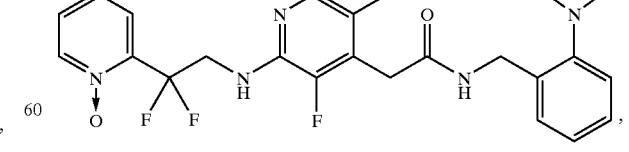
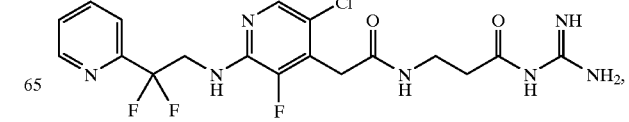

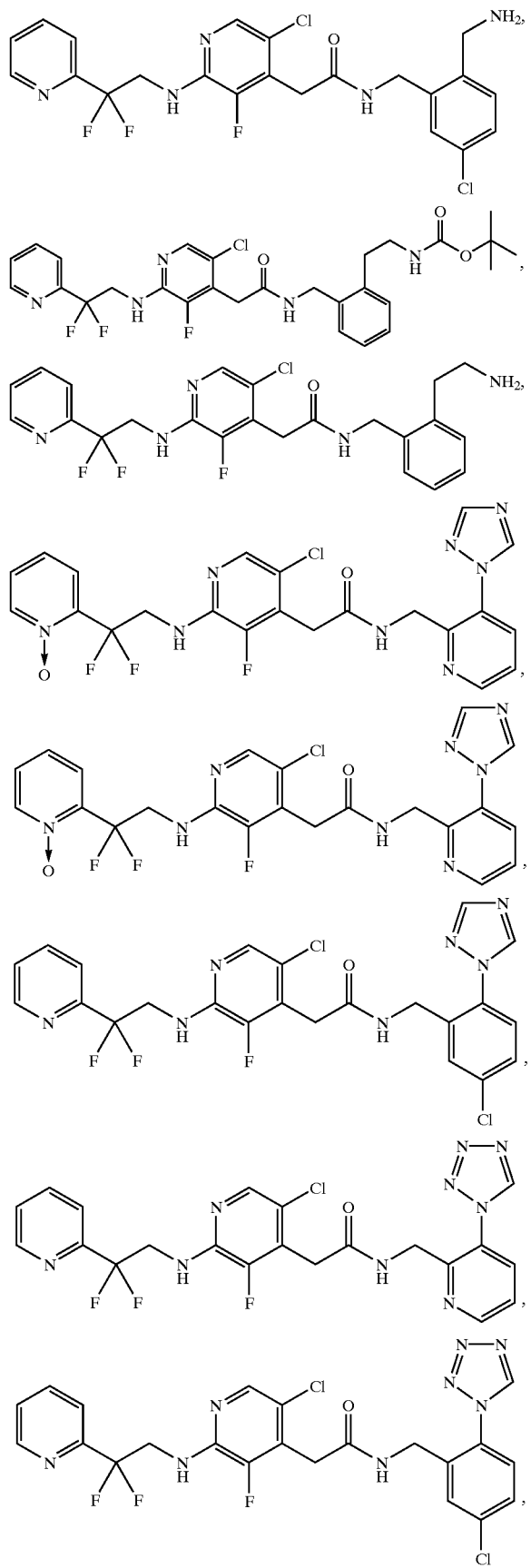
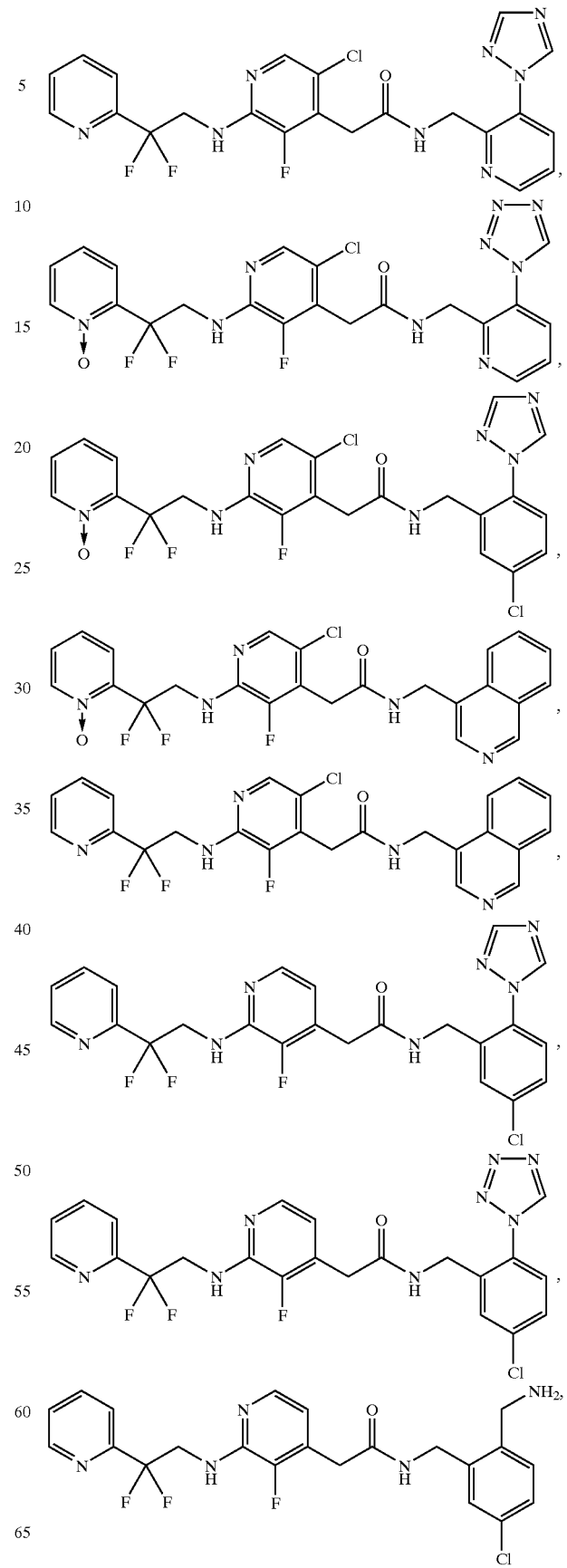

-continued

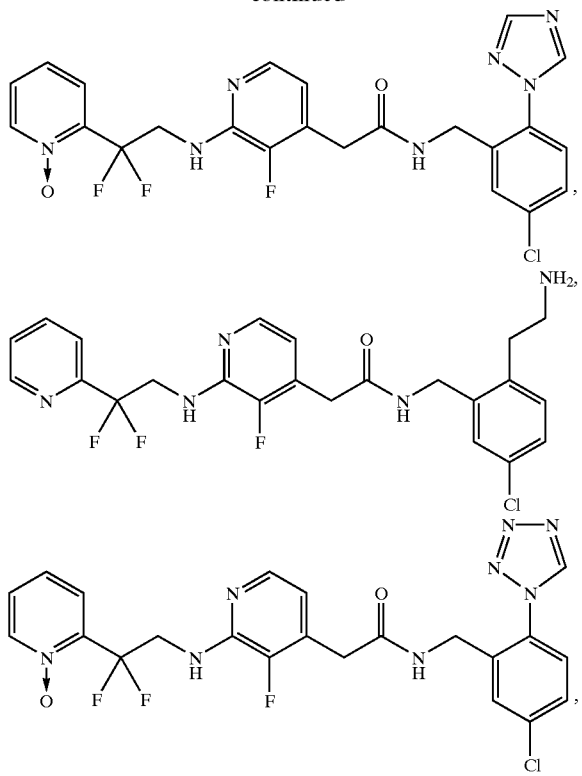

or a pharmaceutically acceptable salt thereof.

9. A composition comprising a compound of claim 1 and a pharmaceutically acceptable carrier.

10. A method for inhibiting thrombin in blood comprising adding to the blood a thrombin inhibiting amount of a composition of claim 9.

11. A method for inhibiting thrombus formation in blood comprising adding to the blood a thrombin inhibiting amount of a composition of claim 9.

12. A method for treating or preventing venous thromboembolism and pulmonary embolism in a mammal comprising administering to the mammal in need thereof a thrombin inhibiting amount of a composition of claim 9.

13. A method for treating or preventing deep vein thrombosis in a mammal comprising administering to the mammal in need thereof a thrombin inhibiting amount of a a composition of claim 9.

14. A method for treating or preventing thromboembolic stroke in a mammal comprising administering to the mammal in need thereof a thrombin inhibiting amount of a composition of claim 9.

15. A method for treating or preventing atherosclerosis in a mammal comprising administering to the mammal in need thereof a thrombin inhibiting amount of a composition of claim 9.

16. A method for treating or preventing thrombosis in a mammal with an inherited thrombophilic disease comprising administering to the mammal in need thereof a thrombin inhibiting amount of a composition of claim 9.

17. A method for treating or preventing thrombosis in a mammal with an acquired thrombophilic disorder comprising administering to the mammal in need thereof a thrombin inhibiting amount of a composition of claim 9.

18. A method for treating or preventing reocclusion in a mammal during or following percutaneous transluminal coronary angioplasty comprising administering to the mammal in need thereof a thrombin inhibiting amount of a composition of claim 9.

19. A method for treating or preventing occlusive cerebrovascular disease in a mammal comprising administering to the mammal in need thereof a thrombin inhibiting amount of a composition of claim 9.

* * * * *